US005712136A

United States Patent [19]
Wickham et al.

[11] Patent Number: 5,712,136
[45] Date of Patent: *Jan. 27, 1998

[54] ADENOVIRAL-MEDIATED CELL TARGETING COMMANDED BY THE ADENOVIRUS PENTON BASE PROTEIN

[75] Inventors: Thomas J. Wickham, Potomac; Imre Kovesdi, Rockville; Petrus W. Roelvink, Gaithersburg; Douglas E. Brough, Otney; Duncan L. McVey, Derwood; Joseph T. Bruder, Frederick, all of Md.

[73] Assignee: GenVec, Inc., Rockville, Md.

[*] Notice: The term of this patent shall not extend beyond the expiration date of Pat. No. 5,559,099.

[21] Appl. No.: 634,060

[22] Filed: Apr. 17, 1996

Related U.S. Application Data

[63] Continuation-in-part of Ser. No. 303,162, Sep. 8, 1994, Pat. No. 5,559,099.

[51] Int. Cl.$^6$ .......................... C12N 15/09; C12N 15/86; C12N 7/01; C07K 14/075
[52] U.S. Cl. ...................... 435/172.3; 435/235.1; 435/320.1; 530/350
[58] Field of Search ........................ 514/44; 435/69.7, 435/172.3, 320.1, 235.1; 536/24.2; 935/57; 530/350

[56] References Cited

U.S. PATENT DOCUMENTS

| | | | |
|---|---|---|---|
| 4,487,829 | 12/1984 | Sharp et al. | 435/5 |
| 4,593,002 | 6/1986 | Dulbecco | 435/172.3 |
| 5,223,409 | 6/1993 | Ladner et al. | 435/69.7 |
| 5,332,567 | 7/1994 | Goldenberg | 424/1.49 |
| 5,349,053 | 9/1994 | Landolfi | 530/351 |
| 5,403,484 | 4/1995 | Ladner et al. | 435/235.1 |
| 5,443,953 | 8/1995 | Hansen et al. | 424/1.49 |
| 5,521,291 | 5/1996 | Curiel et al. | 530/391.7 |
| 5,543,328 | 8/1996 | McClelland et al. | 435/320.1 |
| 5,547,932 | 8/1996 | Curiel et al. | 435/85 |
| 5,559,099 | 9/1996 | Wickham et al. | 514/44 |
| 5,571,698 | 11/1996 | Ladner et al. | 435/69.7 |

FOREIGN PATENT DOCUMENTS

| | | |
|---|---|---|
| WO 91/00360 | 1/1991 | WIPO . |
| WO 91/05805 | 5/1991 | WIPO . |
| WO 91/05871 | 5/1991 | WIPO . |
| WO 92/02553 | 2/1992 | WIPO . |
| WO 93/07282 | 4/1993 | WIPO . |
| WO 93/07283 | 4/1993 | WIPO . |
| WO 94/10323 | 5/1994 | WIPO . |
| WO 94/15644 | 7/1994 | WIPO . |
| WO 94/17832 | 8/1994 | WIPO . |
| WO 94/24299 | 10/1994 | WIPO . |
| WO 95/16037 | 6/1995 | WIPO . |
| WO 95/21259 | 8/1995 | WIPO . |
| WO 95/26412 | 10/1995 | WIPO . |
| WO 95/31566 | 11/1995 | WIPO . |

OTHER PUBLICATIONS

Karyan et al., *Virology*, 202, 782–785 (1994).
Bai et al., *J. Virol.*, 67, 5198–5205 (1993).
Batra et al., *Gene Therapy*, 1, 255–260 (1994).
Boursnell et al., *Gene*, 13, 311–317 (1981).
Chu et al., *Gene Therapy*, 1, 292–299 (1994).
Cotten et al., *Proc. Natl. Acad. Sci.*, 87, 4033–4037 (1990).
Cotten et al., *Proc. Natl. Acad. Sci.*, 89, 6094–6098 (1992).
Crystal, *Science*, 270, 404–410 (1995).
Curiel et al., *Human Gene Therapy*, 3, 147–154 (1992).
Curiel et al., *Proc. Natl. Acad. Sci.*, 88, 8850–8854 (1991).
Dupuit et al., *Human Gene Therapy*, 6, 1185–1193 (1995).
Falgout et al., *J. Virol.*, 62, 622–625 (1992).
Grubb et al., *Nature*, 371, 802–806 (1994).
Henry et al., *J. Virol.*, 68 (8), 5239–5246 (1994).
Horvath et al., *J. Virol.*, 62, 341–345 (1988).
Huang et al., *J. Virol.*, 69, 2257–2263 (1995).
Kass–Eisler et al., *Proc. Natl Acad. Sci.*, 90, 11498–11502 (1993).
Maraveyas et al., *Acta Oncologica*, 32, 741–746 (1993).
Mastrangeli et al., *Ped. Pulm.*, Suppl. 12, 230, Ab. No. 180 (1995).
Mastrangeli et al., *Human Gene Therapy*, 7, 79–87 (1996).
Mathias et al., *J. Virol.*, 68, 6811–6814 (1994).
Michael et al., *The Journal of Biological Chemistry*, 268, 6866–6869 (1993).
Michael et al., *Gene Therapy*, 2, 660–668 (1995).
Michael et al., "Addition of Short Peptide Ligand Sequences to the Adenovirus Fiber Protein," presented at *Adenovirus Workshop: St. Andrews University*, p. 52 (Jul. 13–15, 1995).
Miller et al., *FASEB J.*, 9, 190–199 (1995).
Nemerow et al., *In Biology of Vitronectins and their Receptors* (Preissner et al., eds.), 177–184 (Elsevier Science Publishers, 1993).
Nemerow et al., *Trends in Cell Biology*, 4, 52–55 (1994).
Novelli et al., *Virology*, 185, 365–376 (1991).
Russell et al., *Nucleic Acids Research*, 21, 1081–1085 (1993).
Signas et al., *J. Virol.*, 53, 672–678 (1985).
Silver et al., *Virology*, 165, 377–387 (1988).
Wagner et al., *Proc. Natl. Acad. Sci.*, 89, 6099–6103 (1992).
Watkins et al., "Targeting Adenovirus–Mediated Gene Delivery with Recombinant Antibodies", presented at *Keystone Symposium on Molecular and Cellular Biology*, Abst. No. 336 (Taos: NM, Feb. 22–28, 1996).
Wickham et al., *Cell*, 73, 309–319 (1993).
Wickham et al., *J. Cell. Biol.*, 127, 257–264 (1994).
Wickham et al., *Gene Therapy*, 2, 750–756 (1995).
Etienne–Julan et al., "The efficiency of cell targeting by recombinant retroviruses depends on the nature of the receptor and the composition of the artificial cell–virus linker", J. Gen. Virol. 73:3251–3255, 1992.
Orkin et al., "Report and recommendations of the panel to access the NIH investment in research on gene therapy", Dec. 1995.

*Primary Examiner*—George G. Elliott
*Assistant Examiner*—Robert Schwartzman
*Attorney, Agent, or Firm*—Leydig, Voit & Mayer, Ltd.

[57] ABSTRACT

A method of introducing an adenovirus into a cell that comprises a particular cell surface binding site, as well as a chimeric adenovirus penton base protein and recombinant adenoviral vector comprising the chimeric adenovirus penton base protein for use in the method, are provided.

52 Claims, 18 Drawing Sheets

Thrombin protease cleavage site

Thrombin protease cleavage site

SEQUENCE LISTING ( 1 ) GENERAL INFORMATION:

( i i i ) NUMBER OF SEQUENCES: 60

( 2 ) INFORMATION FOR SEQ ID NO:1:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

Arg  Gly  Asp
    1

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

Lys  Gln  Ala  Gly  Asp
    1                        5

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

Glu  Ile  Leu  Asp  Val
    1                        5

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

Asn  Pro  Xaa  Tyr
    1

( 2 ) INFORMATION FOR SEQ ID NO:5:

( i ) SEQUENCE CHARACTERISTICS:
        ( A ) LENGTH: 65 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
  ( A ) NAME/KEY: CDS
  ( B ) LOCATION: 51..65

( x i ) SEQUENCE DESCRIPTION: SEQ ID NO:5:

```
CTCACCAAGG CCATGGCACC GAGCGTTGGT TTTCTTGAAT TCCCCTTAGT ATG CGG         56
                                                       Met Arg
                                                        1

CGC GCG GCG                                                            65
Arg Ala Ala
         5
```

( 2 ) INFORMATION FOR SEQ ID NO:6:

( i ) SEQUENCE CHARACTERISTICS:
   ( A ) LENGTH: 5 amino acids
   ( B ) TYPE: amino acid
   ( D ) TOPOLOGY: linear ( i i ) MOLECULE TYPE: protein ( x i ) SEQUENCE DESCRIPTION: SEQ ID NO:6:

```
Met Arg Arg Ala Ala
 1               5
```

( 2 ) INFORMATION FOR SEQ ID NO:7:

( i ) SEQUENCE CHARACTERISTICS:
   ( A ) LENGTH: 65 base pairs
   ( B ) TYPE: nucleic acid
   ( C ) STRANDEDNESS: double
   ( D ) TOPOLOGY: unknown ( i i ) MOLECULE TYPE: DNA (genomic)

( i x ) FEATURE:
   ( A ) NAME/KEY: CDS
   ( B ) LOCATION: 51..65

( x i ) SEQUENCE DESCRIPTION: SEQ ID NO:7:

```
CTCACCAAGG CCATGGCACC GAGCGTTGGT TTTCTTGTAT TCCCCTTAGT ATG CGG         56
                                                       Met Arg
                                                        1

CGC GCG GCG                                                            65
Arg Ala Ala
         5
```

( 2 ) INFORMATION FOR SEQ ID NO:8:

( i ) SEQUENCE CHARACTERISTICS:
   ( A ) LENGTH: 5 amino acids
   ( B ) TYPE: amino acid
   ( D ) TOPOLOGY: linear ( i i ) MOLECULE TYPE: protein ( x i ) SEQUENCE DESCRIPTION: SEQ ID NO:8:

```
Val Pro Arg Gly Ser
 1               5
```

( 2 ) INFORMATION FOR SEQ ID NO:9:

( i ) SEQUENCE CHARACTERISTICS:
   ( A ) LENGTH: 30 base pairs
   ( B ) TYPE: nucleic acid
   ( C ) STRANDEDNESS: double
   ( D ) TOPOLOGY: unknown (ii) MOLECULE TYPE: DNA (genomic)

(ix) FEATURE:
                (A) NAME/KEY: CDS
                (B) LOCATION: 1..30

(xi) SEQUENCE DESCRIPTION: SEQ ID NO:9:

| GAC | ATG | AAC | GAT | ACT | AGT | GCC | ACA | CGG | GCT | 30 |
| Asp | Met | Asn | Asp | Thr | Ser | Ala | Thr | Arg | Ala | |
| 1 | | | | 5 | | | | | 10 | |

(2) INFORMATION FOR SEQ ID NO:10:

(i) SEQUENCE CHARACTERISTICS:
                (A) LENGTH: 10 amino acids
                (B) TYPE: amino acid
                (D) TOPOLOGY: linear (ii) MOLECULE TYPE: protein (xi) SEQUENCE DESCRIPTION: SEQ ID NO:10:

Asp Met Asn Asp Thr Ser Ala Thr Arg Ala
1               5                   10

(2) INFORMATION FOR SEQ ID NO:11:

(i) SEQUENCE CHARACTERISTICS:
                (A) LENGTH: 48 base pairs
                (B) TYPE: nucleic acid
                (C) STRANDEDNESS: double
                (D) TOPOLOGY: unknown (ii) MOLECULE TYPE: DNA (genomic)

(ix) FEATURE:
                (A) NAME/KEY: CDS
                (B) LOCATION: 1..48

(xi) SEQUENCE DESCRIPTION: SEQ ID NO:11:

| GAC | ATG | AAC | GAT | CAT | GCC | ATT | CGC | GGC | GAC | ACC | TTT | GCC | ACA | CGG | GCT | 48 |
| Asp | Met | Asn | Asp | His | Ala | Ile | Arg | Gly | Asp | Thr | Phe | Ala | Thr | Arg | Ala | |
| 1 | | | | 5 | | | | | 10 | | | | | 15 | | |

(2) INFORMATION FOR SEQ ID NO:12:

(i) SEQUENCE CHARACTERISTICS:
                (A) LENGTH: 16 amino acids
                (B) TYPE: amino acid
                (D) TOPOLOGY: linear (ii) MOLECULE TYPE: protein (xi) SEQUENCE DESCRIPTION: SEQ ID NO:12:

Asp Met Asn Asp His Ala Ile Arg Gly Asp Thr Phe Ala Thr Arg Ala
1               5                   10                  15

(2) INFORMATION FOR SEQ ID NO:13:

(i) SEQUENCE CHARACTERISTICS:
                (A) LENGTH: 52 bases
                (B) TYPE: nucleic acid
                (C) STRANDEDNESS: single
                (D) TOPOLOGY: unknown (ii) MOLECULE TYPE: DNA (other nucleic acid)

(xi) SEQUENCE DESCRIPTION: SEQ ID NO:13:

AAAACTCACC AAGGCCATGG CACCGAGCGT TGGTTTTCTT GAATTCCCCT TA            52

(2) INFORMATION FOR SEQ ID NO:14:

( i ) SEQUENCE CHARACTERISTICS:
  ( A ) LENGTH: 25 bases
  ( B ) TYPE: nucleic acid
  ( C ) STRANDEDNESS: single
  ( D ) TOPOLOGY: unknown ( i i ) MOLECULE TYPE: DNA (other nucleic acid)

( x i ) SEQUENCE DESCRIPTION: SEQ ID NO:14:

CTGGCGGGCG CGCCAAAATC TGGTT      25

( 2 ) INFORMATION FOR SEQ ID NO:15:

( i ) SEQUENCE CHARACTERISTICS:
  ( A ) LENGTH: 26 bases
  ( B ) TYPE: nucleic acid
  ( C ) STRANDEDNESS: single
  ( D ) TOPOLOGY: unknown ( i i ) MOLECULE TYPE: DNA (other nucleic acid)

( x i ) SEQUENCE DESCRIPTION: SEQ ID NO:15:

AAAACTAGTG CCACACGGGC TGAGGA      26

( 2 ) INFORMATION FOR SEQ ID NO:16:

( i ) SEQUENCE CHARACTERISTICS:
  ( A ) LENGTH: 26 bases
  ( B ) TYPE: nucleic acid
  ( C ) STRANDEDNESS: single
  ( D ) TOPOLOGY: unknown ( i i ) MOLECULE TYPE: DNA (other nucleic acid)

( x i ) SEQUENCE DESCRIPTION: SEQ ID NO:16:

AAAACTAGTA TCGTTCATGT CCTCCA      26

( 2 ) INFORMATION FOR SEQ ID NO:17:

( i ) SEQUENCE CHARACTERISTICS:
  ( A ) LENGTH: 68 base pairs
  ( B ) TYPE: nucleic acid
  ( C ) STRANDEDNESS: double
  ( D ) TOPOLOGY: unknown ( i i ) MOLECULE TYPE: DNA (genomic)

( i x ) FEATURE:
  ( A ) NAME/KEY: CDS
  ( B ) LOCATION: 3..68

( x i ) SEQUENCE DESCRIPTION: SEQ ID NO:17:

```
AA ACT AGT GGA GGA TGC TCT TTT GGC CGC GGC GAC ATT CGC AAC TGC      47
   Thr Ser Gly Gly Cys Ser Phe Gly Arg Gly Asp Ile Arg Asn Cys
    1           5                  10                  15

GGC GGC CTG CAG TCT AGA AAA                                          68
Gly Gly Leu Gln Ser Arg Lys
                20
```

( 2 ) INFORMATION FOR SEQ ID NO:18:

( i ) SEQUENCE CHARACTERISTICS:
  ( A ) LENGTH: 22 amino acids
  ( B ) TYPE: amino acid
  ( D ) TOPOLOGY: linear ( i i ) MOLECULE TYPE: protein ( x i ) SEQUENCE DESCRIPTION: SEQ ID NO:18:

```
Thr  Ser  Gly  Gly  Cys  Ser  Phe  Gly  Arg  Gly  Asp  Ile  Arg  Asn  Cys  Gly
 1              5                        10                       15

Gly  Leu  Gln  Ser  Arg  Lys
                20
```

(2) INFORMATION FOR SEQ ID NO:19:

(i) SEQUENCE CHARACTERISTICS:
        (A) LENGTH: 41 bases
        (B) TYPE: nucleic acid
        (C) STRANDEDNESS: single
        (D) TOPOLOGY: unknown (ii) MOLECULE TYPE: DNA (other nucleic acid)

(xi) SEQUENCE DESCRIPTION: SEQ ID NO:19:

AAACTAGTGG AGGATGCTCT TTTGGCCGCG GCGACATTCG C        41

(2) INFORMATION FOR SEQ ID NO:20:

(i) SEQUENCE CHARACTERISTICS:
        (A) LENGTH: 42 bases
        (B) TYPE: nucleic acid
        (C) STRANDEDNESS: single
        (D) TOPOLOGY: unknown (ii) MOLECULE TYPE: DNA (other nucleic acid)

(xi) SEQUENCE DESCRIPTION: SEQ ID NO:20:

TTTTCTAGAC TGCAGGCCGC CGCAGTTGCG AATGTCGCCG CG       42

(2) INFORMATION FOR SEQ ID NO:21:

(i) SEQUENCE CHARACTERISTICS:
        (A) LENGTH: 110 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 3..110

(xi) SEQUENCE DESCRIPTION: SEQ ID NO:21:

```
AA ACT AGT GGA GGA GAC GAG CTC CCA CAG CTC GTG ACT CTC CCA CAC        47
   Thr Ser Gly Gly Asp Glu Leu Pro Gln Leu Val Thr Leu Pro His
    1           5                   10                  15

CCA AAC CTC CAC GGT CCA GAG ATT CTC GAC GTG CCA TCT ACT GGC GGC       95
Pro Asn Leu His Gly Pro Glu Ile Leu Asp Val Pro Ser Thr Gly Gly
                20                  25                  30

CTG CAG TCT AGA AAA                                                   110
Leu Gln Ser Arg Lys
            35
```

(2) INFORMATION FOR SEQ ID NO:22:

(i) SEQUENCE CHARACTERISTICS:
        (A) LENGTH: 36 amino acids
        (B) TYPE: amino acid
        (D) TOPOLOGY: linear (ii) MOLECULE TYPE: protein (xi) SEQUENCE DESCRIPTION: SEQ ID NO:22:

```
Thr  Ser  Gly  Gly  Asp  Glu  Leu  Pro  Gln  Leu  Val  Thr  Leu  Pro  His  Pro
 1              5                        10                       15
```

Asn Leu His Gly Pro Glu Ile Leu Asp Val Pro Ser Thr Gly Gly Leu
            20                  25                      30

Gln Ser Arg Lys
            35

( 2 ) INFORMATION FOR SEQ ID NO:23:

( i ) SEQUENCE CHARACTERISTICS:
        ( A ) LENGTH: 65 bases
        ( B ) TYPE: nucleic acid
        ( C ) STRANDEDNESS: single
        ( D ) TOPOLOGY: unknown ( i i ) MOLECULE TYPE: DNA (other nucleic acid)

( x i ) SEQUENCE DESCRIPTION: SEQ ID NO:23:

AAACTAGTGG AGGAGACGAG CTCCCACAGC TCGTGACTCT CCCACACCCA AACCTCCACG    60

GTCCA    65

( 2 ) INFORMATION FOR SEQ ID NO:24:

( i ) SEQUENCE CHARACTERISTICS:
        ( A ) LENGTH: 60 bases
        ( B ) TYPE: nucleic acid
        ( C ) STRANDEDNESS: single
        ( D ) TOPOLOGY: unknown ( i i ) MOLECULE TYPE: DNA (other nucleic acid)

( x i ) SEQUENCE DESCRIPTION: SEQ ID NO:24:

TTTTCTAGAC TGCAGGCCGC CAGTAGATCG CACGTCGAGA ATCTCTGGAC CGTGGAGGTT    60

( 2 ) INFORMATION FOR SEQ ID NO:25:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

Asp Tyr Lys Asp Asp Asp Asp Lys
1                   5

( 2 ) INFORMATION FOR SEQ ID NO:26:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

Thr Ser Glu Ala Ala Ala His Ala Ile Arg Gly Asp Thr Tyr Ala Asp
1               5                       10                  15

Tyr Lys Asp Asp Asp Asp Lys Gly Ser Ser
            20                  25

( 2 ) INFORMATION FOR SEQ ID NO:27:

( i ) SEQUENCE CHARACTERISTICS:
        ( A ) LENGTH: 25 amino acids
        ( B ) TYPE: amino acid
        ( C ) STRANDEDNESS: single ( D ) TOPOLOGY: linear ( i i ) MOLECULE TYPE: peptide ( x i ) SEQUENCE DESCRIPTION: SEQ ID NO:27:

Thr Ser Glu Ala Ala Ala His Ala Ile Arg Gly Asp Thr Tyr Pro Tyr
1               5                       10                      15

Asp Val Pro Asp Tyr Ala Gly Ser Ser
            20                  25

( 2 ) INFORMATION FOR SEQ ID NO:28:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (other nucleic acid)

( x i ) SEQUENCE DESCRIPTION: SEQ ID NO:28:

GGACTAGTGA GGCGGCGGCC CACGCCATCC GCGGCGACAC CTAC    44

( 2 ) INFORMATION FOR SEQ ID NO:29:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (other nucleic acid)

( x i ) SEQUENCE DESCRIPTION: SEQ ID NO:29:

GCTCTAGACC CGGCGTAGTC GGGCACGTCG TAGGGGTAGG TGTCGCCGCG GAT    53

( 2 ) INFORMATION FOR SEQ ID NO:30:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (other nucleic acid)

( x i ) SEQUENCE DESCRIPTION: SEQ ID NO:30:

GCTCTAGACC CCTTGTCGTC GTCGTCCTTG TAGTCGGCGT AGGTGTCGCC GCGGAT    56

( 2 ) INFORMATION FOR SEQ ID NO:31:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:31:

Tyr Pro Tyr Asp Val Pro Asp Tyr Ala
1               5

( 2 ) INFORMATION FOR SEQ ID NO:32:

( i ) SEQUENCE CHARACTERISTICS:
        ( A ) LENGTH: 9 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:32:

Glu Asp Pro Gly Phe Phe Asn Val Glu
    1               5

(2) INFORMATION FOR SEQ ID NO:33:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Glu Pro Gly Lys Gln Leu Tyr Asn Val Glu
    1               5                   10

(2) INFORMATION FOR SEQ ID NO:34:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

Lys Lys Lys Lys Lys
    1               5

(2) INFORMATION FOR SEQ ID NO:35:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

Arg Arg Arg Arg Arg
    1               5

(2) INFORMATION FOR SEQ ID NO:36:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Leu Asp Val
    1

(2) INFORMATION FOR SEQ ID NO:37:

(i) SEQUENCE CHARACTERISTICS:
        (A) LENGTH: 12 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:37:

```
Asn Asp His Ala Ile Arg Gly Asp Thr Tyr Arg Ala
1               5                   10
```

(2) INFORMATION FOR SEQ ID NO:38:

(i) SEQUENCE CHARACTERISTICS:
      (A) LENGTH: 28 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:38:

```
Asn Asp Thr Ser Glu Ala Ala Ala His Ala Ile Arg Gly Asp Thr Tyr
1               5                   10                  15
Pro Tyr Val Pro Asp Tyr Ala Gly Ser Ser Arg Ala
                20                  25
```

(2) INFORMATION FOR SEQ ID NO:39:

(i) SEQUENCE CHARACTERISTICS:
      (A) LENGTH: 30 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:39:

```
Asn Asp Thr Ser Glu Ala Ala Ala His Ala Ile Arg Gly Asp Thr Tyr
1               5                   10                  15
Ala Asp Tyr Lys Asp Asp Asp Lys Gly Ser Ser Arg Ala
                20                  25              30
```

(2) INFORMATION FOR SEQ ID NO:40:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:40:

```
Gly Val Pro Arg Gly Ser Leu Gly
1               5
```

(2) INFORMATION FOR SEQ ID NO:41:

(i) SEQUENCE CHARACTERISTICS:
      (A) LENGTH: 57 base pairs
      (B) TYPE: nucleic acid
      (C) STRANDEDNESS: double
      (D) TOPOLOGY: unknown (ii) MOLECULE TYPE: DNA (other nucleic acid)

(xi) SEQUENCE DESCRIPTION: SEQ ID NO:41:

```
GGA AAG CTA GGC CGA GGA GTT CCC AGA GGG AGT CTT GGA AGG GGG AAG    48
Gly Lys Leu Gly Arg Gly Val Pro Arg Gly Ser Leu Gly Arg Gly Lys
1               5                   10                  15
```

```
CTA GCC CTG                                                                                        57
Leu Ala Leu
```

( 2 ) INFORMATION FOR SEQ ID NO:42:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:42:

```
Gly Lys Leu Gly Arg Gly Val Pro Arg Gly Ser Leu Gly Arg Gly Lys
 1               5                  10                  15

Leu Ala Leu
```

( 2 ) INFORMATION FOR SEQ ID NO:43:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (other nucleic acid)

( x i ) SEQUENCE DESCRIPTION: SEQ ID NO:43:

```
CTAGGCCGAG GAGTTCCCAG AGGGAGTCTT GGAAGGGGGA AG                                                     42
```

( 2 ) INFORMATION FOR SEQ ID NO:44:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (other nucleic acid)

( x i ) SEQUENCE DESCRIPTION: SEQ ID NO:44:

```
CTAGCTTCCC CCTTCCAAGA CTCCCTCTGG GAACTCCTCG GC                                                     42
```

( 2 ) INFORMATION FOR SEQ ID NO:45:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: unknown ( i i ) MOLECULE TYPE: DNA (other nucleic acid)

( x i ) SEQUENCE DESCRIPTION: SEQ ID NO:45:

```
CTA AAT CTA AGA CTA GGA CAG GGC CGA GGA GTT CCC AGA GGG AGT CTT                                    48
Leu Asn Leu Arg Leu Gly Gln Gly Arg Gly Val Pro Arg Gly Ser Leu
 1               5                  10                  15

GGA AGG GGC CCT CTT                                                                                63
Gly Arg Gly Pro Leu
                20
```

( 2 ) INFORMATION FOR SEQ ID NO:46:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:46:

Leu Asn Leu Arg Leu Gly Gln Gly Arg Gly Val Pro Arg Gly Ser Leu
1               5                   10                  15
Gly Arg Gly Pro Leu
            20

( 2 ) INFORMATION FOR SEQ ID NO:47:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (other nucleic acid)

( x i ) SEQUENCE DESCRIPTION: SEQ ID NO:47:

GAGGAGTTCC CAGAGGGAGT CTTGGAAGGG GCC                    33

( 2 ) INFORMATION FOR SEQ ID NO:48:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (other nucleic acid)

( x i ) SEQUENCE DESCRIPTION: SEQ ID NO:48:

CCTTCCAAGA CTCCCTCTGG GAACTCCTCG GCC                    33

( 2 ) INFORMATION FOR SEQ ID NO:49:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: unknown ( i i ) MOLECULE TYPE: DNA (other nucleic acid)

( x i ) SEQUENCE DESCRIPTION: SEQ ID NO:49:

ACC CAA GGA CGA GGA GTT CCC AGA GGG AGT CTT GGA AGA GGA CCC CTC    48
Thr Gln Gly Arg Gly Val Pro Arg Gly Ser Leu Gly Arg Gly Pro Leu
1               5                   10                  15

( 2 ) INFORMATION FOR SEQ ID NO:50:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:50:

Thr Gln Gly Arg Gly Val Pro Arg Gly Ser Leu Gly Arg Gly Pro Leu
1               5                   10                  15

( 2 ) INFORMATION FOR SEQ ID NO:51:

( i ) SEQUENCE CHARACTERISTICS:
        ( A ) LENGTH: 33 base pairs
        ( B ) TYPE: nucleic acid ( C ) STRANDEDNESS: single
( D ) TOPOLOGY: linear ( i i ) MOLECULE TYPE: DNA (other nucleic acid)

( x i ) SEQUENCE DESCRIPTION: SEQ ID NO:51:

GACGAGGAGT TCCCAGAGGG AGTCTTGGAA GAG     33

( 2 ) INFORMATION FOR SEQ ID NO:52:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (other nucleic acid)

( x i ) SEQUENCE DESCRIPTION: SEQ ID NO:52:

GTCCTCTTCC AAGACTCCCT CTGGGAACTC CTC     33

( 2 ) INFORMATION FOR SEQ ID NO:53:

( i ) SEQUENCE CHARACTERISTICS:
( A ) LENGTH: 54 base pairs
( B ) TYPE: nucleic acid
( C ) STRANDEDNESS: double
( D ) TOPOLOGY: unknown ( i i ) MOLECULE TYPE: DNA (other nucleic acid)

( x i ) SEQUENCE DESCRIPTION: SEQ ID NO:53:

```
ATT  GGC  CAT  GGC  CGA  GGA  GTT  CCC  AGA  GGG  AGT  CTT  GGA  AGG  GGA  CAT     48
Ile  Gly  His  Gly  Arg  Gly  Val  Pro  Arg  Gly  Ser  Leu  Gly  Arg  Gly  His
 1              5                        10                       15

GGC  CTA                                                                           54
Gly  Leu
```

( 2 ) INFORMATION FOR SEQ ID NO:54:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:54:

```
Ile  Gly  His  Gly  Arg  Gly  Val  Pro  Arg  Gly  Ser  Leu  Gly  Arg  Gly  His
 1              5                        10                       15

Gly  Leu
```

( 2 ) INFORMATION FOR SEQ ID NO:55:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (other nucleic acid)

( x i ) SEQUENCE DESCRIPTION: SEQ ID NO:55:

CATGGCCGAG GAGTTCCCAG AGGGAGTCTT GGAAGGGGA     39

( 2 ) INFORMATION FOR SEQ ID NO:56:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (other nucleic acid)

( x i ) SEQUENCE DESCRIPTION: SEQ ID NO:56:

CATGTCCCCT TCCAAGACTC CCTCTGGGAA CTCCTCGGC  39

( 2 ) INFORMATION FOR SEQ ID NO:57:

( i ) SEQUENCE CHARACTERISTICS:
    ( A ) LENGTH: 54 base pairs
    ( B ) TYPE: nucleic acid
    ( C ) STRANDEDNESS: double
    ( D ) TOPOLOGY: unknown ( i i ) MOLECULE TYPE: DNA (other nucleic acid)

( x i ) SEQUENCE DESCRIPTION: SEQ ID NO:57:

| GAA | GGA | AAG | CTA | GGC | AAA | AAG | AAA | AAG | GGT | AAG | AAA | AAG | AAA | GGG | AAG | 48 |
| Glu | Gly | Lys | Leu | Gly | Lys | Lys | Lys | Lys | Gly | Lys | Lys | Lys | Lys | Gly | Lys | |
| 1 | | | | 5 | | | | | 10 | | | | | 15 | | |

CTA GCC   54
Leu Ala ( 2 ) INFORMATION FOR SEQ ID NO:58:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:58:

| Glu | Gly | Lys | Leu | Gly | Lys | Lys | Lys | Lys | Gly | Lys | Lys | Lys | Lys | Gly | Lys |
| 1 | | | | 5 | | | | | 10 | | | | | 15 | |

Leu Ala ( 2 ) INFORMATION FOR SEQ ID NO:59:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (other nucleic acid)

( x i ) SEQUENCE DESCRIPTION: SEQ ID NO:59:

CTAGGCAAAA AGAAAAAGGG TAAGAAAAAG AAAGGGAAG  39

( 2 ) INFORMATION FOR SEQ ID NO:60:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (other nucleic acid)

( x i ) SEQUENCE DESCRIPTION: SEQ ID NO:60:

CTAGCTTCCC TTTCTTTTTC TTACCCTTTT TCTTTTTGC  39

ADENOVIRAL-MEDIATED CELL TARGETING COMMANDED BY THE ADENOVIRUS PENTON BASE PROTEIN

RELATED APPLICATION

This is a continuation-in-part application of U.S. patent application Ser. No. 08/303,162, U.S. Pat. No. 5,559,099 filed Sep. 8, 1994.

TECHNICAL FIELD OF THE INVENTION

The present invention pertains to a method of introducing an adenovirus into a cell that comprises a particular cell surface binding site, and a chimeric adenovirus penton base protein and recombinant adenoviral vector comprising the chimeric adenovirus penton base protein that can be employed in this method.

BACKGROUND OF THE INVENTION

Adenoviruses belong to the family Adenoviridae, which is divided into two genera, namely Mastadenovirus and Aviadenovirus (Horwitz, In Virology, 3rd ed., Fields et al., eds., 2149–2171 (Raven Press, New York, (1996)); Shenk, In Virology, 3rd ed., Fields et al., eds., 2111–2148 (Raven Press, New York, (1996)); Murphy, In Virology, 3rd ed., Fields et al., eds., 15–57 (Raven Press, New York, (1996)). Adenoviruses are nonenveloped, regular icosahedrons of about 65 to 80 nanometers (nm) in diameter. The adenoviral capsid is comprised of 252 capsomeres, of which 240 are hexons and 12 are pentons. The penton comprises a penton base, which provides a point of attachment to the capsid, and a trimeric fiber protein, which is noncovalently bound to and projects from the penton base. The penton base protein itself is a ring-shaped complex comprised of five identical protein subunits of polypeptide III (571 amino acids)(Boudin et al., Virology, 92, 125–138 (1979)).

An adenovirus such as Ad2 uses two of the coat proteins, fiber protein and penton base protein, to interact with distinct cellular receptors to attach to and efficiently infect a cell (Wickham et al., Cell, 73, 309–319 (1993)). First, the fiber protein attaches the virus to a cell by binding to an as yet unidentified receptor. Then, the penton base binds to specific members of a family of heterodimeric cell surface receptors termed integrins. The integrins not only provide a binding site for the adenoviral penton base protein, but also mediate cellular adhesion to the extracellular matrix (ECM) molecules fibronectin, vitronectin, laminin, and collagen, as well as other molecules.

The specificity with which an integrin binds to a particular ligand such as the adenovirus penton base protein is a function of the paired α and β subunits of the integrin. For instance, the penton base of the adenovirus serotype Ad2 binds to integrins $\alpha_v\beta_3$ and $\alpha_v\beta_5$ (Wickham et al. (1993), supra; Nemerow et al., In Biology of Vitronectins and their Receptors, Preissner et al. (eds.), 177–184 (Elsevier Science Publishers (1993)); Varga et al., J. Virol., 65, 6061–6070 (1991)). Whereas some integrins, such as the $\alpha_v$ integrins, are present on the surface of nearly all cells, except for unstimulated hematopoietic cells (Gladson et al., In Integrins, Y. Takada (ed.), 83–99 (CRC Press, Boca Raton, Fla. (1994))), other integrins have a narrower tissue distribution. In particular, $\beta_2$ integrins are present only on leukocytes, such as neutrophils and macrophages, $\alpha_4$ integrins are present only on lymphocytes and fibroblasts, and the $\alpha_{IIb}\beta_3$ integrin is present only on platelets and megakaryocytes. Based on this, the integrin subunit complement of a cell in some sense limits the infectability of that cell by different serotypes of adenovirus.

In binding to a specific ligand, most integrins recognize short linear stretches of amino acids. In particular, the tripeptide RGD (i.e., Arg Gly Asp [SEQ ID NO:1]) motif is found in the majority of ECM ligands. Other integrins, which do not utilize the RGD motif, have been found to bind similar short linear stretches of amino acids within their specific ligands. For instance, integrin $\alpha_{IIb}\beta_3$ binds via the amino acid sequence KQAGD (i.e., Lys Gln Ala Gly Asp [SEQ ID NO:2]) in fibrinogen (Kloczewiak et al., Biochemistry, 23, 1767–1774 (1984)), and $\alpha_4\beta_1$ binds via the core sequence EILDV (i.e., Glu Ile Leu Asp Val [SEQ ID NO:3]) in fibronectin (Komoriya et al., J. Biol. Chem., 266, 15075–15079 (1991)). Another structural motif, NPXY (i.e., Asn Pro Xaa Tyr [SEQ ID NO:4]), that is present in the β subunits of $\alpha_v$-containing integrins, similarly has been shown to be important for integrin-mediated internalization (Suzuki et al., Proc. Natl. Acad. Sci., 87, 5354 (1990)).

The RGD tripeptide similarly appears to control binding of adenovirus to $\alpha_v$ integrins since exogenously added RGD peptides can block penton base binding and adenoviral infection (Wickham et al. (1993), supra), and since adenoviruses that have point mutations in the RGD sequence of the penton base protein are restricted in their ability to infect cells (Bai et al., J. Virol., 67, 5198–5205 (1993)). The penton base sequence is conserved among the various serotypes of adenovirus that have been sequenced (Neumann et al., Gene, 69, 153–157 (1988)). In particular, Ad2 and Ad5 are identical in the hypervariable region that includes the RGD sequence motif, and contain a large insert of amino acids flanking either side of the RGD sequence. Secondary structural analysis of the hypervariable regions of the RGD-containing penton bases of Ad2, Ad5, and Ad12 predicts that, in each case, the RGD motif is flanked by α-helices, which are believed to form the spikes seen in cryo-electron micrographic (cryo-EM) images of the Ad2 penton base (Stewart et al., EMBO J., 12(7), 2589–2599 (1993)). The penton base protein of Ad2 appears to play no role in virus attachment (Wickham et al. (1993), supra).

Once an adenovirus attaches to a cell via its fiber protein it undergoes receptor-mediated internalization into clathrin-coated endocytic vesicles by means of penton base protein binding to integrins. Ultimately, the viral particles are then transported to the nuclear pore complex of the cell, where the viral genome enters the nucleus, thus initiating infection. This ability of adenovirus to efficiently enter cells has allowed the adenoviral-mediated targeted transfer of one or more recombinant genes to diseased cells or tissue in need of treatment. As reviewed by Crystal, Science, 270, 404–410 (1995), adenoviral vectors are preferred over other vectors commonly employed for gene therapy (e.g., retroviral vectors) since adenoviral vectors can be produced in high titers (i.e., up to about $10^{13}$ viral particles/ml), and they efficiently transfer genes to nonreplicating, as well as replicating, cells. Moreover, if the targeted tissue for somatic gene therapy is the lung, adenoviral vectors are additionally preferred based on their normal tropism for the respiratory epithelium.

Other advantages that accompany the use of adenoviruses as vectors for gene therapy include: (1) recombination is rarely observed with adenoviruses; (2) there is no ostensible correlation of any human malignancy with adenoviral infections despite common human infection with adenoviruses; (3) the adenoviral genome (which is comprised of linear, double-stranded DNA) can be manipulated to carry up to about 7.5 kb of exogenous DNA, and longer DNA sequences can potentially be carried into a cell, for instance, attached to the adenoviral capsid (Curiel et al., *Human Gene Therapy*, 3, 147–154 (1992)); (4) an adenovirus is unlikely to interfere with normal cell function since the vector commands expression of its encoded sequences in an epichromosomal fashion; and (5) live adenovirus has been safely used as a human vaccine for many years.

A drawback to the use of adenovirus in gene therapy is that all cells that comprise both of the aforementioned two binding sites used by the adenovirus to attach to and infect a cell (i.e., the fiber receptor and the binding site for the penton base protein) will internalize the gene(s) being administered, and not just the cells in need of therapeutic treatment. Also, cells that lack either one or both of the aforementioned binding sites will be impaired in adenoviral-mediated gene delivery. For instance, cells which lack a particular integrin receptor may not be easily amenable to adenovirus-mediated gene delivery (Silver et al., *Virology*, 165, 377–387 (1988); Horvath et al., *J. Virol.*, 62, 341–345 (1988); Huang et al., *J. Virol.*, 69, 2257–2263 (1995)). Similarly, other cells appear to lack an adenoviral fiber receptor and are transduced by adenovirus, if at all, with a very low efficiency (as described, for instance, in U.S. patent application Ser. No. 08/563,368, filed Nov. 28, 1995; Curiel et al., supra; Cotten et al., *Proc. Natl. Acad. Sci.*, 87, 4033–4037 (1990); Wattel et al., *Leukemia*, 10, 171–174 (1996)). Accordingly, limiting adenoviral entry to specific cells and/or expanding the repertoire of cells amenable to adenovirus-mediated gene therapy would constitute a substantial improvement over the current technology. Such truly 'targeted' adenoviral gene delivery also potentially could reduce the amount of adenoviral vector that is necessary to obtain gene expression in the targeted cells, and thus potentially reduce side effects and complications associated with an increased dose of adenovirus.

In efforts to achieve cell targeting, adenovirus has been employed essentially as an endosomolytic agent in the transfer into a cell of plasmid DNA containing a marker gene which is complexed and condensed with polylysine covalently linked to a cell-binding ligand, such as transferrin (Cotten et al., *Proc. Natl. Acad. Sci.*, 89, 6094–6098 (1992); Curiel et al., *Proc. Natl. Acad. Sci.*, 88, 8850–8854 (1991)). It has been demonstrated that coupling of the transferrin-polylysine/DNA complex and adenovirus (e.g., by means of an adenovirus-directed antibody, with transglutaminase, or via a biotin/streptavidin bridge) substantially enhances gene transfer (Wagner et al., *Proc. Natl. Acad. Sci.*, 89, 6099–6103 (1992)). However, these approaches are somewhat less than desirable in that they require the ligation of the ligand such as transferrin with polylysine, and the advance preparation of the transferrin-polylysine DNA complexes. Moreover, the complexes formed with adenovirus would appear to retain the capacity of being endocytosed by binding either to cellular adenovirus receptors or to transferrin receptors. Additionally, polylysine by itself is capable of binding to cells which may interfere with the specificity of this approach (U.S. patent application Ser. No. 08/563,368, filed Nov. 28, 1995).

To circumvent such non-specific binding of the adenovirus, the fiber protein of adenovirus has been modified either by incorporating sequences for a ligand to a cell surface receptor, or sequences that allow binding to a bispecific antibody (i.e., a molecule with one end having specificity for the fiber protein, and the other end having specificity for a cell surface receptor) (PCT International Patent Application WO 95/26412; Watkins et al., "Targeting Adenovirus-Mediated Gene Delivery with Recombinant Antibodies", presented at *Keystone Symposium on Molecular and Cellular Biology*, Abst. No. 336 (Taos: N.M., Feb. 22–28, 1996). In both cases, the typical fiber/cell surface receptor interactions are abrogated, and the adenovirus is redirected to a new cell surface receptor by means of its fiber protein. Some downfalls associated with the approach of the '412 Application, which calls for modification of the fiber protein, are that such fiber modifications can require the need for different cell lines (i.e., cell lines having the receptor for which the modified virus is now targeted) to propagate the virus, and/or a different means of cell delivery (e.g., liposome-mediated delivery) to introduce adenovirus intracellularly. Moreover, the approach of Watkins et al. and the '412 Application would appear to be limited to the use of the fiber protein of adenovirus for cell targeting.

Yet another approach to targeted gene delivery calls for administering a targeting element coupled to a first molecule of a high affinity binding pair, wherein the targeting element is capable of specifically binding to a selected cell type (PCT International Application WO 95/31566). Then, a gene delivery vehicle coupled to a second molecule of the high affinity binding pair is administered, wherein the second molecule is capable of specifically binding to the first molecule such that the gene delivery vehicle is targeted to the selected cell type. The sequential administration of the various components likely is done to prevent agglomeration of the vector particles, e.g., in cases where the targeting element is multivalent for the domain which recognizes the vector, which would reduce transduction efficiency. However, such sequential administration is disadvantageous since it allows for the possibility that the targeting element is internalized before it can complex with the vector. Internalization of the preadministered targeting element will clear the receptor from the cell surface, thus preventing efficient targeting of the complexed targeting element and vector, and also potentially leading to impairment of the cell processes controlled by the receptors. Moreover, such premature internalization also would necessitate the use of relatively high levels of the targeting element.

The present invention seeks to overcome the problems of the aforesaid approaches to recombinant adenoviral gene therapy. Accordingly, it is an object of the present invention to provide a method of selectively introducing an adenovirus into a cell that comprises a particular cell surface binding site such as a receptor, as well as vectors and other constituents for carrying out the method. These and other objects and advantages of the present invention, as well as additional inventive features, will be apparent from the following detailed description.

BRIEF SUMMARY OF THE INVENTION

The present invention provides a method of introducing an adenovirus into a cell that comprises a particular cell surface binding site (e.g., a receptor), which method comprises: (a) contacting the adenovirus with a bispecific molecule comprising (i) a first component that selectively binds a binding domain of the penton base protein of the adenovirus, and (ii) a second component that selectively binds the particular cell surface binding site, to form a complex of the adenovirus and the bispecific molecule, and (b) contacting the cell with the complex. The invention also provides a method of introducing an adenovirus into a cell that comprises a particular cell surface binding site, which method comprises: (a) abrogating the binding of the fiber protein of the adenovirus to any cell surface molecule to which the fiber protein of the adenovirus can bind to effect cell entry of the adenovirus, and (b) contacting the cell with the adenovirus such that the penton base protein of the adenovirus binds the particular cell surface binding site and cell entry of the adenovirus is effected. The invention further provides a chimeric adenovirus penton base protein, and a vector (particularly a recombinant adenoviral vector) comprising the chimeric adenovirus penton base protein which can be employed in the method. The method of the invention is commanded by the adenovirus penton base protein.

DETAILED DESCRIPTION OF THE INVENTION

Figure 1:
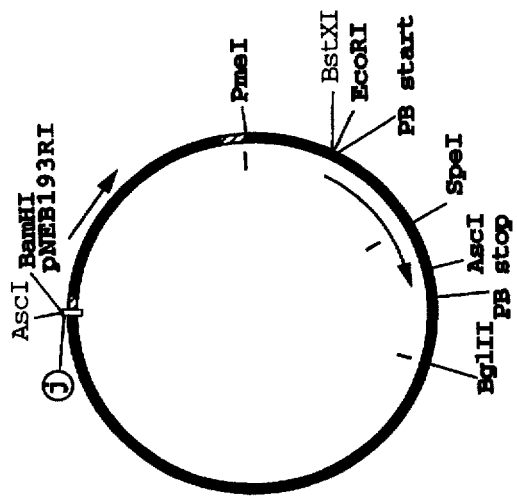
FIG. 1 is a partial restriction map of an adenoviral transfer vector (pAT).

The present invention provides, among other things, a method of selectively introducing an adenovirus into a cell. Preferably this method is carried out in order to effect transfer into a cell of an exogenous nucleic acid sequence, such as a passenger gene, in a method of gene transfer.

Method of Gene Transfer

According to the invention, an "adenovirus" is any virus of the family Adenoviridae, and desirably is of the genus Mastadenovirus (e.g., mammalian adenoviruses) or Aviadenovirus (e.g., arian adenoviruses). The adenovirus is of any serotype vector. Adenoviral stocks that can be employed as a source of adenovirus or adenovirus coat protein such as penton base and/or fiber protein can be amplified from the adenovirus serotypes from type 1 through 47 currently available from American Type Culture Collection (ATCC, Rockville, Md.), or from any other serotype of adenovirus available from any other source. For instance, an adenovirus can be of subgroup A (e.g., serotypes 12, 18, 31), subgroup B (e.g., serotypes 3, 7, 11, 14, 16, 21, 34, 35), subgroup C (e.g., serotypes 1, 2, 5, 6), subgroup D (e.g., serotypes 8, 9, 10, 13, 15, 17, 19, 20, 22–30, 32, 33, 36–39, 42–47), subgroup E (serotype 4), subgroup F (serotype 40, 41), or any other adenoviral serotype. Preferably, however, an adenovirus is of an Ad5 serotype. Desirably an adenovirus comprises coat proteins (e.g., penton base protein, hexon protein, and/or fiber protein) of the same serotype. However, also preferably, the coat protein can be chimeric (as further defined herein) in the sense that it is from another serotype, or comprises sequences from more than one serotype adenoviral vector.

Preferably the adenovirus is replication competent. Alternately, preferably the adenoviral vector comprises a genome with at least one modification therein, optimally which renders the virus replication deficient. The modification to the adenoviral genome includes, but is not limited to, addition of a DNA segment, rearrangement of a DNA segment, deletion of a DNA segment, replacement of a DNA segment, or introduction of a DNA lesion. A DNA segment is as small as one nucleotide and as large as 36 kilobase pairs (i.e., the approximate size of the adenoviral genome) or, alternately, can equal the maximum amount which is packaged into an adenoviral virion (i.e., about 38 kb). Preferred modifications to the adenoviral genome include modifications in the E1, E2, E3 and/or E4 regions. An adenovirus also preferably can be a cointegrate, i.e., a ligation of adenoviral genomic sequences with other sequences, such as other virus, phage, or plasmid sequences.

By "selective introduction" is meant introduction into a particular cell rather than into another cell. According to the invention, a cell can be any cell, and, preferably, is a eukaryotic cell. A eukaryotic cell is a cell which possesses a nucleus surrounded by a nuclear membrane. Preferably the eukaryotic cell is of a multicellular species (e.g., as opposed to a unicellular yeast cell), and, even more preferably, is a mammalian (optimally human) cell. However, the method also can be effectively carried out using a wide variety of different cell types such as arian cells, and mammalian cells including but not limited to rodent, primate (such as chimpanzee, monkey, ape, gorilla, orangutan, or gibbon), feline, canine, ungulate (such as ruminant or swine), as well as, in particular, human cells. Desirably such a eukaryotic cell is one in which an adenovirus can exist for a period of time (i.e., typically from anywhere up to, and potentially even after, about two months) after entry into the cell. Optimally, nascent RNA is transcribed from the adenovirus genome or passenger nucleic acid carried into the cell by the adenovirus, as further described herein.

A cell can be present as a single entity, or can be part of a larger collection of cells. Such a "larger collection of cells" can comprise, for instance, a cell culture (either mixed or pure), a tissue (e.g., epithelial or other tissue), an organ (e.g., heart, lung, liver, gallbladder, urinary bladder, eye, and other organs), an organ system (e.g., circulatory system, respiratory system, gastrointestinal system, urinary system, nervous system, integumentary system or other organ system), or an organism (e.g., a bird, mammal, or the like). Preferably, the organs/tissues/cells being targeted are of the circulatory system (e.g., including, but not limited to heart, blood vessels, and blood), respiratory system (e.g., nose, pharynx, larynx, trachea, bronchi, bronchioles, lungs, and the like), gastrointestinal system (e.g., including mouth, pharynx, esophagus, stomach, intestines, salivary glands, pancreas, liver, gallbladder, and others), urinary system (e.g., such as kidneys, ureters, urinary bladder, urethra, and the like), nervous system (e.g., including, but not limited to brain and spinal cord, and special sense organs such as the eye) and integumentary system (e.g., skin). Even more preferably, the cells being targeted are selected from the group consisting of heart, blood vessel, lung, liver, gallbladder, urinary bladder, and eye cells.

In particular, a cell into which selective introduction is accomplished according to the invention differs from another cell (in which introduction of the adenovirus is not accomplished) in that the cell so being targeted comprises a particular cell surface binding site. By "particular cell surface binding site" is meant any site (i.e., molecule or combination of molecules) present on the surface of a cell which provides a site with which adenovirus can interact to bind the cell as further described herein, and thereby promote cell entry. A particular cell surface binding site therefore encompasses a cell surface receptor, and preferably is a protein (including a modified protein), a carbohydrate, a glycoprotein, a proteoglycan, a lipid, a mucin molecule or mucoprotein, and the like. Examples of potential cell surface binding sites include, but are not limited to: heparin and chondroitin sulfate moieties found on glycosaminoglycans; sialic acid moieties found on mucins, glycoproteins, and gangliosides; major histocompatability complex I (MHC I) glycoproteins; common carbohydrate molecules found in membrane glycoproteins, including mannose, N-acetyl-galactosamine, N-acetyl-glucosamine, fucose, and galactose; glycoproteins such as ICAM-1, VCAM, E-selectin, P-selectin, L-selectin, and integrin molecules; and tumor-specific antigens present on cancerous cells, such as, for instance, MUC-1 tumor-specific epitopes. However, the present method of selectively introducing an adenovirus into a cell is not limited to any specific mechanism of cellular interaction (i.e., interaction with a given cell surface binding site), and is not to be so construed.

The method by which selective introduction of adenovirus into a cell is accomplished comprises: (a) contacting the adenovirus with a bispecific molecule to form a complex of the adenovirus and the bispecific molecule, and (b) contacting the cell with this complex, preferably so as to result in a cell having the adenovirus therein. To optimize the ability of the adenovirus to enter the cell by the method of the invention, preferably the method is carried out in the absence of neutralizing antibodies directed against the particular adenovirus being introduced intracellularly. In the absence of such antibodies, there is no possibility of the adenovirus being bound by the antibody, and thus impeded from binding and/or entering the cell. It is well within the ordinary skill of one in the art to test for the presence of such neutralizing antibodies. In the event the presence of such neutralizing antibodies are an obstacle to the intracellular delivery of an adenovirus, another adenoviral vector, e.g., another serotype adenoviral vector (Crompton et al., *J. Gen. Virol.*, 75, 133–139 (1994)), or another adenovirus vector lacking the epitope against which the antibody is directed, can be employed.

A "complex" of the adenovirus and the bispecific molecule is any interaction, e.g., covalent or noncovalent, between the adenovirus and the bispecific molecule, and, preferably, is a noncovalent interaction. Such "contacting" can be done by any means known to those skilled in the art, and described herein, by which the apparent touching or mutual tangency of the adenovirus and bispecific molecule, or of the cell and the complex of the adenovirus and bispecific molecule, can be effected. For instance, contacting of the adenovirus and the bispecific molecule can be done by mixing these elements in a small volume of the same solution. Optionally, the elements further can be covalently joined, e.g., by chemical means known to those skilled in the art, or other means, or preferably can be linked by means of noncovalent interactions (e.g., ionic bonds, hydrogen bonds, Van der Waals forces, and/or nonpolar interactions). In comparison, the cell and the complex need not necessarily be brought into contact in a small volume, as, for instance, in cases where the complex is administered to a host, and the complex travels by the bloodstream to the cell in which it selectively binds and enters. The contacting of the adenovirus with a bispecific molecule preferably is done before the cell is contacted with the complex of the adenovirus and bispecific molecule. By "before" is meant any amount of time prior to contacting the cell sufficient to ensure that a complex of the adenovirus and the bispecific molecule is formed prior to the complex contacting the cell, e.g., a period of time that ranges from about five minutes to about five years (or, to about as long as the maximum length of time a complex of an adenovirus and a bispecific molecule can be stably maintained in a useable form, for instance, lyophilized, or in the presence of cryoprotective agents at −80° C.).

A "bispecific molecule" according to the invention is a molecule with specificity for at least two (i.e., it can be more than two) molecules. A bispecific molecule can be any combination of an antibody and/or an attachment sequence, as further described herein. Such a bispecific molecule preferably comprises: (i) a first component that selectively binds a binding domain of the penton base protein of the adenovirus, and (ii) a second component that selectively binds the particular cell surface binding site present on the cell into which the adenovirus is introduced, as further described herein.

A "component" (i.e., a first or second component) is any molecule that can interact (e.g., covalently or noncovalently) with either a binding domain of a penton base protein or a particular cell surface binding site. Optimally the first and second component of the bispecific molecule are linked to each other in some fashion, e.g., for instance, by a covalent interaction (e.g., chemical linkage and/or fusion with two or more protein domains), or by a noncovalent interaction. A component preferably is an antibody (e.g., a polyclonal, monoclonal, bispecific, and/or single-chain antibody) and/or an attachment sequence (e.g., such as a ligand for a cell surface binding site).

A component that is an attachment sequence preferably is a ligand (e.g., for a cell surface binding site such as a receptor). The presence of a ligand for a cell surface binding site in the bispecific molecule (e.g., optimally in the second component) provides for targeting to cells having on their surface this specific binding site for the ligand. Examples of preferred binding sites and their respective ligands or attachment sequences for use in the method of the invention include, but are not limited to: CR2 receptor binding the amino acid residue attachment sequences EDPGFFNVE (i.e., Glu Asp Pro Gly Phe Phe Asn Val Glu [SEQ ID NO:32]) and EPGKQLYNVE (i.e., Glu Pro Gly Lys Gln Leu Tyr Asn Val Glu [SEQ ID NO:33]); CD4 receptor recognizing the V3 loop of HIV gp120; transferrin receptor and its ligand transferrin; low density lipoprotein receptor and its ligand; the ICAM-1 receptor on epithelial and endothelial cells in lung and its ligand; and asialoglycoproteins that recognize deglycosylated protein ligands. Moreover, additional ligands and their binding sites preferably include (but are not limited to) linear stretches of amino acids recognized by integrins, such as, the tripeptides RGD (i.e., Arg Gly Asp [SEQ ID NO:1]) and LDV (i.e., Leu Asp Val [SEQ ID NO:36]), the sequence KQAGD (i.e., Lys Gln Ala Gly Asp [SEQ ID NO:2]), and the sequence EILDV (i.e., Glu Ile Leu Asp Val [SEQ ID NO:3]), as well as polylysine (i.e., Lys Lys Lys Lys Lys [SEQ ID NO:34], wherein the sequence can be present one to ten times) and polyarginine sequences (i.e., Arg Arg Arg Arg Arg [SEQ ID NO:35], wherein the sequence can be present one to ten times). Inserting multiple lysines and/or arginines provides for recognition of heparin and DNA.

A component that is an antibody, e.g., directed against a particular cell surface binding site or an epitope present on a chimeric or wild-type penton base protein, can be incorporated into the bispecific molecule, preferably in the first component. Such an antibody includes, but is not limited to, immunoglobulin molecules and immunologically active portions of immunoglobulin molecules such as portions containing a paratope (i.e., an antigen binding site), such that the antibody comprises, for example, either intact immunoglobulin molecules or portions thereof, such as those known in the art as Fab, Fab', F(ab')$_2$ and F(v). The antibody can be, for example, a monoclonal antibody, a polyclonal antibody, a single-chain antibody (e.g.) that further can comprise a ligand or attachment sequence in addition to a paratope), and a bispecific antibody (e.g., that in and of itself can be a bispecific molecule having one paratope directed to an epitope of a wild-type or chimeric penton protein, and another paratope directed to an epitope of a cell surface binding site).

Preferred antibodies according to the invention are those that are directed against any cell surface binding site, particularly those previously mentioned, and those that are directed against any binding domain that constitutes an epitope present in wild-type (i.e., native) or chimeric penton base protein. Accordingly, optimally an antibody is directed against the CR2 receptor, the CD4 receptor, the transferrin receptor, the low density lipoprotein receptor, the ICAM-1 receptor, asialoglycoproteins, and any of the integrins. Also preferably, an antibody is directed against an exposed region of a penton base protein, e.g., one that projects outward from the capsid protein and is conformationally accessible for binding to a bispecific antibody. Accordingly, further preferred antibodies of either type (i.e., those directed against either a cell surface binding site or an epitope in wild-type or chimeric penton base protein) include, but are not limited to: the L230 monoclonal antibody directed against $\alpha_v$ integrins; the M2 monoclonal antibody directed against the FLAG octapeptide DYKDDDDK (i.e., Asp Tyr Lys Asp Asp Asp Asp Lys [SEQ ID NO:25]; the L230:FLAG bispecific antibody which incorporates the L230 and M2 monoclonal antibodies; the OKT7:FLAG bispecific antibody which incorporates a FLAG monoclonal antibody linked to an antibody directed against the CD3 T cell receptor; the mICAM:FLAG bispecific antibody which incorporates a FLAG monoclonal antibody linked to an antibody directed against the ICAM-1 receptor; the P1F6 antibody directed against the integrin $\alpha_v\beta_5$; the 1B1.3.2 monoclonal antibody directed against the $\alpha v$ subunit of $\alpha_v$ integrins; and the 12CA5 monoclonal antibody directed against the hemagluttinin peptide.

The antibody can be produced by any suitable technique, e.g., conventional techniques for preparing monoclonal, polyclonal, single-chain, and bispecific antibodies, as well as more current recombinant DNA techniques that are familiar to those skilled in the art. For instance, antibodies directed against adenovirus in particular can be made as described, for example, in U.S. Pat. No. 4,487,829. Chimeric molecules having a ligand component linked to an immunoglobulin constant region, and other immunoconjugates such as bispecific antibodies, can be made as described, for instance, in U.S. Pat. Nos. 4,816,567, 5,349, 053, 5,332,567, and 5,443,953, and PCT International Applications WO 90/14424, WO 91/05805, WO 91/05871, WO 92/02553, and WO 95/16037; Cook et al., *J. Immunol. Methods*, 171, 227–237 (1994); and Spooner et al., *Human Pathol.*, 25, 606–614 (1994). In particular, bispecific antibodies can be made by a variety of means, e.g., chemical techniques (see, e.g., Kranz et al., *Proc. Natl. Acad. Sci.*, 78, 5807 (1981)), for instance, disulfide cleavage reformation of whole IgG or, preferably, F(ab')$_2$ fragments; fusions of more than one clone to form polyomas that produce immunoglobulins having more than one specificity (see, e.g., U.S. Pat. No. 4,474,893; Segal et al., *In Current Protocols in Immunology*, Coligan et al. (eds.), vol. 1, 2.13.1–2.13.16 (John Wiley & Sons, Inc. (1995))); or by genetic engineering (see, e.g., U.S. Pat. No. 4,816,567 and PCT International Patent Application WO 90/14424).

A component such as an antibody and/or an attachment sequence comprising a bispecific molecule "selectively binds" a binding domain of an adenovirus penton base protein and/or a cell surface binding site when it interacts with that binding domain and/or cell surface binding site with a greater affinity, or is specific for or has specificity for that binding domain and/or cell surface binding site, as compared with other binding domains and/or cell surface binding sites. The terms "has specificity for" and "is specific for" refer to the degree of selectivity shown by a peptide or protein with respect to the number and types of reactants with which the protein interacts and the rates and extent of these reactions, the degree of selectivity shown by an antibody with respect to the number and types of antigens with which the antibody combines and the rates and the extent of these reactions, or refers to the type and the degree of permeability to substances transported across the membrane by a cell surface binding protein. The term "selectively binds" in the present context means binding sufficient to be useful in the method of the invention. As is known in the art, useful selective binding, for instance, to a receptor, depends on both the binding affinity and the concentration of ligand achievable in the vicinity of the receptor. Thus, binding affinities lower than that found for any naturally occurring competing ligands are useful, so long as the cell or tissue to be treated can tolerate concentrations of added ligand sufficient to compete, for instance, for binding to a cell surface receptor.

A "binding domain" is a region on either a chimeric penton base protein or a wild-type penton base protein with which a component interacts. Preferably this is either a covalent or noncovalent interaction. A binding domain can comprise an epitope (i.e., an antigenic determinant or the portion of an antigen that combines with an antibody in an antigen-antibody reaction). A binding domain also preferably is a peptide sequence or protein domain that is capable of recognizing a cell surface binding site and being internalized by receptor-mediated endocytosis upon binding at the cell surface. It also preferably is a "coupler" protein sequence that is used to couple other proteins to the chimeric penton protein. An example of this is sequences such as those described in the art that mediate biotin-avidin (streptavidin) binding (e.g., as described by Saggio et al., *Biochem. J.*, 293, 613–616 (1993); Alon, *Eur. J. Immunol.*, 23, 893–898 (1993); Miller et al., *Biochem. J.*, 278, 573–585 (1991)) and serve as attachment sites for avidin and biotin conjugated proteins.

Accordingly, preferably a binding domain on a chimeric or wild-type penton base protein comprises any of the aforementioned attachment sequences, e.g., EDPGFFNVE (i.e., Glu Asp Pro Gly Phe Phe Asn Val Glu [SEQ ID NO:32]) and EPGKQLYNVE (i.e., Glu Pro Gly Lys Gln Leu Tyr Asn Val Glu [SEQ ID NO:33]) recognized by the CR2 receptor; the V3 loop of HIV gp120 recognized by the CD4 receptor; the ligand transferrin recognized by the transferrin receptor; the ligand for the low density lipoprotein receptor; the ligand for the ICAM-1 receptor on epithelial and endothelial cells in lung; deglycosylated protein ligands recognized by asialoglycoprotein; linear stretches of amino acids recognized by integrins, such as, the tripeptides RGD (i.e., Arg Gly Asp [SEQ ID NO:1]) and LDV (i.e., Leu Asp Val [SEQ ID NO:36], the sequence KQAGD (i.e., Lys Gln Ala Gly Asp [SEQ ID NO:2]), and the sequence EILDV (i.e., Glu Ile Leu Asp Val [SEQ ID NO:3]), as well as polylysine (i.e., Lys Lys Lys Lys Lys [SEQ ID NO:34]), wherein the sequence can be present one to ten times) and polyarginine (i.e., Arg Arg Arg Arg Arg [SEQ ID NO:35], wherein the sequence can be present one to ten times) sequences, which provide for recognition of heparin and DNA.

Also, preferably a binding domain on wild-type or chimeric penton base protein comprises an epitope for: the M2 monoclonal antibody directed against the FLAG octapeptide DYKDDDDK (i.e., Asp Tyr Lys Asp Asp Asp Asp Lys [SEQ ID NO:25]); the L230:FLAG bispecific antibody which incorporates the L230 and M2 monoclonal antibodies; the OKT7:FLAG bispecific antibody which incorporates a FLAG monoclonal antibody linked to an antibody directed against the CD3 T cell receptor; the mICAM:FLAG bispecific antibody which incorporates a FLAG monoclonal antibody linked to an antibody directed against the ICAM-1 receptor; or the 12CA5 monoclonal antibody directed against the hemagluttinin peptide. With respect to a chimeric penton base protein, the binding domain can comprise a portion of the wild-type sequence in part, and a portion of the non-wild-type sequence in part. Similarly, the sequences (either native and/or nonnative) that comprise the binding domain in either the chimeric or wild-type penton base protein need not necessarily be contiguous in the chain of amino acids that comprise the protein. In other words, the binding domain can be generated by the particular conformation of the protein, e.g., through folding of the protein in such a way as to bring contiguous and/or noncontiguous sequences into mutual proximity.

A "penton base protein" (or a "fiber protein") according to the invention preferably is an adenovirus protein. A "chimeric" protein (e.g., either penton base or fiber) is one that preferably comprises amino acid residues, or a sequence of amino acids, that are not found in the protein as isolated from nature, and result from human intervention regarding the composition of the protein. A protein as isolated from nature, in the absence of any human intervention regarding the composition of the protein, is referred to herein as a "wild-type" or "native" protein. Correspondingly, when the protein is part of an adenovirus, a wild-type protein is obtained from a "wild-type adenovirus" (i.e., an adenovirus that is not the result of human manipulation of the penton base and/or fiber, e.g., of its nucleic or amino acid sequence, although the wild-type adenovirus can comprise mutations in its genome, such as, for instance, mutations that render the vector replication deficient), and a chimeric protein is obtained from a "recombinant adenovirus" (i.e., an adenovirus that is the result of human manipulation of the penton base and/or fiber, e.g., of the nucleic or amino acid sequence). A chimeric protein in a recombinant adenovirus also desirably is a substitution of a penton base and/or fiber protein of one adenoviral serotype for that of another adenoviral serotype, as further described herein.

There are multiple preferred embodiments of the method of the present invention. For instance, the method preferably is carried out wherein the adenovirus comprises a passenger gene, as described herein. Also, the method preferably is carried out wherein the cell that comprises a particular cell surface binding site is one that wild-type adenovirus typically does not bind (i.e., transduce or infect), or binds with an apparent low efficiency, (e.g., non-epithelial cells including monocyte/macrophages, fibroblasts, neuronal, smooth muscle, and endothelial cells, as described in U.S. patent application Ser. No. 08/563,368, filed Nov. 28, 1995). However, the method also preferably can be carried out to introduce adenovirus into any cell, even a cell that wild-type adenovirus binds and enters with relatively high efficiency (e.g., epithelial cells).

The method desirably is carried out wherein the bispecific molecule is a bispecific antibody comprising (a) a first antibody that selectively binds the binding domain of the adenovirus penton base protein, and (b) a second antibody that selectively binds the cell surface binding site present on the surface of the cell into which adenovirus is being selectively introduced. This method optionally is carried out using either an adenovirus that comprises a wild-type adenovirus penton base protein, or an adenovirus that comprises a chimeric adenovirus penton base protein, as further described herein. The chimeric adenovirus penton base protein preferably comprises a binding domain that effects binding to a particular molecule which wild-type adenovirus penton base protein does not bind. The binding domain of the chimeric adenovirus penton base protein (like the binding domain of the wild-type adenovirus penton base protein) preferably comprises an epitope for the first antibody. Preferably the epitope of the chimeric adenovirus penton base protein comprises a sequence selected from the group consisting of SEQ ID NO:25 (i.e., DYKDDDDK, or Asp Tyr Lys Asp Asp Asp Asp Lys), SEQ ID NO:26 (i.e., TSEAAA-HAIRGDTYADYKDDDDKGSS or Thr Ser Glu Ala Ala Ala His Ala Ile Arg Gly Asp Thr Tyr Ala Asp Tyr Lys Asp Asp Asp Asp Lys Gly Ser Ser), SEQ ID NO:27 (i.e., TSEAAAHAIRGDTYPYDVPDYAGSS or Thr Ser Glu Ala Ala Ala His Ala Ile Arg Gly Asp Thr Tyr Pro Tyr Asp Val Pro Asp Tyr Ala Gly Ser Ser), and SEQ ID NO:31 (i.e., YPYDVPDYA or Tyr Pro Tyr Asp Val Pro Asp Tyr Ala) or derivations of these sequences (i.e, comprising deletions and/or mutations) that are recognized by either the M2 or 12CA5 monoclonal antibodies, or other antibodies directed against either the FLAG or hemagglutinin peptides.

The method of the present invention also preferably is carried out wherein it further comprises abrogating (i.e., preventing) the binding of the fiber protein of the adenovirus being selectively introduced into a cell. In particular, preferably the binding of the adenoviral fiber protein to any cell surface binding site by which adenovirus can effect cell entry is abrogated. In this preferred embodiment, any interaction of the fiber protein with its cell surface receptor is eliminated, thus precluding any of these interactions from interfering with the ability of the penton base protein to target cell binding/cell entry to a particular cell surface receptor. In any embodiment according to the invention, however, desirably it is the penton base protein of adenovirus that commands cell binding/cell entry.

This method preferably is carried out wherein the adenovirus comprises either a chimeric or wild-type penton base protein, as described above, and as further described herein. For instance, desirably binding is abrogated by contacting the adenovirus with an antibody that selectively binds an epitope of the wild-type adenovirus fiber protein. Preferably this antibody (or other agent) binds in such a fashion so as to prevent interaction of the adenovirus fiber protein with its receptor. Even more preferably, the antibody is a function-blocking antibody.

Alternately, preferably the adenovirus employed in the method (comprising either a chimeric or wild-type penton base protein) further comprises a chimeric adenovirus fiber protein. Optionally the binding of the chimeric adenovirus fiber protein is abrogated by contacting the adenovirus with an antibody or other agent that selectively binds an epitope of the chimeric adenovirus fiber protein. Desirably this antibody (or other agent) binds in such a fashion so as to prevent interaction of the adenovirus fiber protein with its receptor. In another preferred variation of the method, the chimeric adenovirus fiber protein preferably comprises a protease cleavage site, and binding of the fiber protein is abrogated by cleaving the fiber protein at the cleavage site. For instance, insertion of a polylysine string anywhere within the sequence of the fiber protein will allow selective cleavage at that site by trypsin. In particular, introduction of a cleavage site into the fiber shaft will allow removal of the fiber protein, and introduction into the knob of the fiber will allow inactivation of the fiber protein.

The adenovirus also desirably can comprise a chimeric adenovirus fiber protein that is characterized by being naturally unable to bind to a cell to which wild-type adenovirus fiber protein can bind. For instance, the chimeric adenovirus fiber protein optionally comprises an adenovirus fiber protein that is of a different adenoviral serotype than the remainder of the recombinant adenovirus. Desirably the chimeric adenovirus fiber protein comprises an adenovirus fiber protein that is of shorter length than the wild-type adenovirus fiber protein. For instance, the fiber protein of the Ad9 serotype is shorter than the fiber protein of Ad5. The fiber protein of the Ad9 serotype recognizes the same receptor as Ad5, but Ad9, unlike serotypes Ad2 and Ad5, does not use its fiber protein to bind to cells (Roelvink et al., "Comparative Analysis of Adenovirus Fiber-Cell Interaction: Adenovirus Serotypes 2, 5 and 9 Compete for the Same Fiber Receptor", *J. Virol.*, submitted). Similarly, the fiber protein of most adenovirus serotypes is shorter than the fiber proteins of Ad2 and Ad5. The switching of fiber proteins to form an adenovirus having a chimeric fiber protein (i.e., a fiber protein that is chimeric in the sense of being of a different adenoviral serotype than the remainder of the vector) further is advantageous in that the shorter length of the chimeric fiber protein employed in the method preferably will allow bispecific antibodies complexed to the penton base protein to sterically inhibit the interaction of the chimeric fiber protein (e.g., the Ad9 fiber protein) with the adenoviral fiber receptor. Currently it appears that all the tested fiber proteins of different adenoviral serotypes will support viral propagation in 293 cells based on the fact that 293 cells are derived from HEK cells, and HEK cells will support the propagation of the majority of, if not all, adenovirus serotypes (ATCC, *Animal Viruses & Antisera; Chlamydiae & Rickettsiae,* 1, (1995)).

In yet another preferred embodiment of a method of introducing an adenovirus into a cell that comprises a particular cell surface binding site, the method comprises: (a) abrogating the binding of the fiber protein of the adenovirus to any cell surface molecule to which the fiber protein of the adenovirus can bind to effect cell entry of the adenovirus, and (b) contacting the cell with the adenovirus such that the penton base protein of the adenovirus binds the particular cell surface binding site and cell entry of the adenovirus is effected. This method ideally is carried out wherein the adenovirus comprises a passenger gene. Optimally, the penton base protein is a wild-type adenovirus penton base protein. However, the penton base protein also desirably is a chimeric adenovirus penton base protein that comprises a binding domain that differs from the binding domain of a wild-type adenovirus penton base protein and that binds the particular cell surface binding site present on the cell into which entry is being effected. In particular, preferably the cell surface binding site is one that wild-type adenovirus does not bind. Desirably the binding domain comprises a sequence selected from the group consisting of SEQ ID NO:3 (i.e., EILDV or Glu Ile Leu Asp Val, SEQ ID NO:32 (i.e., EDPGFFNVE or Glu Asp Pro Gly Phe Phe Asn Val Glu), SEQ ID NO:33 (i.e., EPGKQLYNVE or Glu Pro Gly Lys Gln Leu Tyr Asn Val Glu), SEQ ID NO:34 (i.e., Lys Lys Lys Lys Lys), SEQ ID NO:35 (i.e., Arg Arg Arg Arg Arg), and SEQ ID NO:36 (i.e., LDV or Leu Asp Val). Alternately, preferably the cell surface binding site is one that wild-type adenovirus does bind, and the binding domain desirably comprises the sequence of SEQ ID NO:18 (i.e., Thr Ser Gly Gly Cys Ser Phe Gly Arg Gly Asp Ile Arg Asn Cys Gly Gly Leu Gln Ser Arg Lys).

This preferred embodiment similarly can be carried out wherein the fiber protein is either a wild-type or chimeric adenovirus fiber protein, and binding of the fiber protein is abrogated by contacting the adenovirus with an antibody that selectively binds an epitope of the wild-type or chimeric adenovirus fiber protein. Alternately, the fiber protein preferably is a chimeric adenovirus fiber protein that comprises a protease cleavage site, and binding of the fiber protein is abrogated by cleaving the fiber protein at the cleavage site. Also, preferably the fiber protein is a chimeric adenovirus fiber protein that is unable to bind to a cell to which wild-type adenovirus fiber protein can bind. In particular, preferably the chimeric adenovirus fiber protein comprises an adenovirus fiber protein that is of a different adenoviral serotype than the remainder of the adenovirus, and/or desirably comprises an adenovirus fiber protein that is of shorter length than the wild-type adenovirus fiber protein.

In still other preferred embodiments of the present invention, the method of introducing an adenovirus into a cell that comprises a particular cell surface binding site are preferably carried out using the recombinant adenoviral vectors of the invention (i.e., comprising chimeric penton base and/or fiber proteins), as described herein.

Chimeric Adenovirus Proteins

The present invention thus provides, among other things, a chimeric adenovirus penton base protein, which, along with a wild-type adenovirus penton base protein, can be employed in the method of the invention. Desirably, the chimeric adenovirus penton base protein is derived from a wild-type adenovirus penton base protein (or its encoding nucleic acid sequence). Any serotype of adenovirus can be used as a source of penton protein (i.e., either as a source of DNA for generating the protein by recombinant means, or as a source of the protein itself). The ordinary skilled artisan is well versed in the means of protein production. Moreover, the chimeric penton proteins and methods of producing the proteins set out in PCT International Patent Application WO 94/17832 can be employed in the context of the present invention.

Preferably the chimeric penton base protein differs from the wild-type penton base protein in that it comprises an addition to the wild-type protein or replacement in the protein of an amino acid sequence. Such an addition or replacement is made such that the chimeric penton base protein comprises a binding domain (i.e., an attachment sequence or an epitope for an antibody, as previously described) that optimally differs from (i.e., comprises a different sequence than) the binding domain of a wild-type adenovirus penton base protein. It is possible, however, that a chimeric penton base protein comprises a binding domain that is the same as that found in wild-type penton base protein (e.g., comprises the LDV motif, Leu Asp Val [SEQ ID NO:36]), so long as the sequence of the chimeric penton base protein differs from that of the wild-type penton base protein, and in this case, optimally, the binding domain has been moved to a new position within the protein (e.g., so as to render it conformationally accessible to binding).

Desirably, a chimeric penton base protein comprising an attachment sequence binding domain constitutes an addition to the wild-type protein or replacement in the protein of an amino acid sequence of between about one and about two hundred fifty amino acids, more preferably between about one and about one hundred amino acids, and optimally, between about one and about fifty amino acids. Preferably the chimeric adenovirus penton base protein comprises a binding domain that effects binding to a particular molecule that wild-type adenovirus penton base protein does not bind, and desirably, comprises a sequence selected from the group consisting of SEQ ID NO:3 (i.e., EILDV or Glu Ile Leu Asp Val, SEQ ID NO:32 (i.e., EDPGFFNVE or Glu Asp Pro Gly Phe Phe Asn Val Glu), SEQ ID NO:33 (i.e., EPGKQLYNVE or Glu Pro Gly Lys Gln Leu Tyr Asn Val Glu), SEQ ID NO:34 (i.e., Lys Lys Lys Lys Lys), SEQ ID NO:35 (i.e., Arg Arg Arg Arg Arg), and SEQ ID NO:36 (i.e., LDV or Leu Asp Val). Alternately, preferably the chimeric adenovirus penton base protein comprises a binding domain that binds a molecule which wild-type penton base protein does bind. In particular, preferably the binding domain comprises the sequence of SEQ ID NO:18 (i.e., Thr Ser Gly Gly Cys Ser Phe Gly Arg Gly Asp Ile Arg Asn Cys Gly Gly Leu Gln Ser Arg Lys).

In another preferred embodiment, the binding domain of the chimeric adenovirus penton base protein preferably comprises an epitope for an antibody. Desirably, in this case, the addition to the wild-type protein or replacement in the protein comprises an amino acid sequence of between about one and about fifty amino acids, more preferably between about one and about thirty amino acids, and optimally between about one and about fifteen amino acids. Preferably, the epitope comprises the sequence of SEQ ID NO:25 (i.e., DYKDDDDK, or Asp Tyr Lys Asp Asp Asp Asp Lys), SEQ ID NO:26 (i.e., TSEAAAHAIRGDTYADYKDDDDKGSS or Thr Ser Glu Ala Ala Ala His Ala Ile Arg Gly Asp Thr Tyr Ala Asp Tyr Lys Asp Asp Asp Asp Lys Gly Ser Ser), SEQ ID NO:27 (i.e., TSEAAAHAIRGDTYPYDVPDYAGSS or Thr Ser Glu Ala Ala Ala His Ala Ile Arg Gly Asp Thr Tyr Pro Tyr Asp Val Pro Asp Tyr Ala Gly Ser Ser), or SEQ ID NO:31 (i.e., YPYDVPDYA or Tyr Pro Tyr Asp Val Pro Asp Tyr Ala). The epitope for the antibody preferably is one that is not present in wild-type penton base protein.

Similarly, a chimeric fiber protein preferably can be constructed for use in the method of the invention by inserting into the fiber gene a unique protease site, to allow targeting of an adenovirus through the penton base or penton base chimeric protein in the absence of the typical fiber/cell surface receptor interactions. The protease site preferably does not affect fiber trimerization or receptor specificity of the fiber protein. The chimeric fiber-containing particles preferably are produced in standard cell lines, e.g., those currently used for adenoviral vectors. Following production and purification, the particles are rendered fiberless through digestion of the particles with a sequence-specific protease, which cleaves the fiber proteins and releases them from the viral particles to generate fiberless particles. For example, thrombin recognizes and cleaves at the amino acid sequence Val Pro Arg Gly Ser (TRINS) [SEQ ID NO:8] (Stenflo et al., *J. Biol. Chem.*, 257, 12280–12290 (1982)) as well as the sequence GVPRGSLG (Gly Val Pro Arg Gly Ser Leu Gly [SEQ ID NO:40]). Other fiber deficient vectors can be constructed as described in the Examples which follow. Also, fiberless particles have been suggested to be stable and capable of binding and infecting cells (Falgout et al., *J. of Virology*, 62, 622–625 (1992)). These resultant particles (i.e., comprising inactive fiber) then can be targeted to specific tissues via the penton base or other coat protein.

Accordingly, the present invention also preferably provides a chimeric fiber protein that comprises a protease cleavage site comprised of the amino acid sequence of SEQ ID NO:8, SEQ ID NO:40, SEQ ID NO:42, SEQ ID NO:46, SEQ ID NO:50, SEQ ID NO:54, or SEQ ID NO:58, and is encoded by the nucleic acid sequence of SEQ ID NO:41, SEQ ID NO:43, SEQ ID NO:45, SEQ ID NO:49, SEQ ID NO:53, and SEQ ID NO:57. Thus, preferably the invention provides a vector comprising a sequence selected from the group consisting of SEQ ID NO:41, SEQ ID NO:43, SEQ ID NO:45, SEQ ID NO:49, SEQ ID NO:53, and SEQ ID NO:57, and/or a sequence selected from the group consisting of SEQ ID NO:8, SEQ ID NO:40, SEQ ID NO:42, SEQ ID NO:46, SEQ ID NO:50, SEQ ID NO:54, and SEQ ID NO:58 (Glu Gly Lys Leu Gly Lys Lys Lys Gly Lys Lys Lys Lys Gly Lys Leu Ala).

Alternately, recombinant adenoviruses comprising chimeric fiber protein preferably can be produced by the removal of the native knob region, which comprises receptor-binding and trimerization domains, of the fiber protein and its replacement with a nonnative trimerization domain and a protein-specific binding domain (Peteranderl et al., *Biochemistry*, 31, 12272–12276 (1992)). A chimeric fiber protein also preferably can be produced by introducing point mutations in the knob region and then isolating clones that are capable of trimerization but incapable of binding to the native receptor. In either case, new protein binding domains preferably can be added onto the C-terminus of the fiber protein or into exposed loops of the fiber protein by inserting the nucleic acid sequence encoding the binding domain into the fiber gene sequence at the appropriate position. Irrespective of which method is used to introduce a protein binding sequence into the fiber protein, the fiber protein preferably is able to trimerize.

The conventional abbreviations for amino acids comprising proteins and peptides are used herein as generally accepted in the peptide art and as recommended by the IUPAC-IUB Commission on Biochemical Nomenclature (*European J. Biochem.*, 138, 9–37 (1984)). Similarly, protein and peptide sequences are written according to the standard convention wherein the N-terminal amino acid is on the left and the C-terminal amino acid is on the right. The term "peptide" as used herein refers to any length molecular chain of amino acids linked by peptide bonds, so long as the length of the peptide is less than that of a full length protein. The term "peptide" encompasses the term "polypeptide", which refers more specifically to a linear polymer of more than 10 amino acids.

The proteins and peptides of the present invention preferably comprise an amino end and a carboxyl end. They can comprise D- or L- peptides, or a mixture of the D- and L-amino acid forms. Proteins and peptides comprising L-amino acids are preferred. However, the D-form of the amino acids are also desirable since proteins and peptides comprising D-amino acids are expected to have a greater retention of their biological activity in vivo given that the D-amino acids are not recognized by naturally occurring proteases. Of course, proteins comprising the D-form of amino acids, unlike those comprising the L-form of amino acids, cannot be synthesized in a living cell, and must be produced by chemical means.

Accordingly, the proteins (and peptides) according to the invention can be prepared by any of a number of conventional techniques. For instance, in the case of recombinant peptides, a DNA fragment encoding a desired peptide can be subcloned into an appropriate vector using well known molecular genetic techniques (see, e.g., Maniatis et al., *Molecular Cloning: A Laboratory Manual*, 2nd ed. (Cold Spring Harbor Laboratory, 1989)). The fragment can be transcribed and the peptide subsequently translated in vitro. Commercially available kits can also be employed (e.g., such as manufactured by Clontech, Palo Alto, Calif.; Amersham Life Sciences, Inc., Arlington Heights, Ill.; InVitrogen, San Diego, Calif., and the like). The polymerase chain reaction optionally can be employed in manipulation of nucleic acids.

Alterations of the native amino acid sequence to produce variant peptides (such as the chimeric penton base and fiber proteins) can be done by a variety of means known to those skilled in the art. A variant peptide is a peptide that is substantially homologous to another indicated peptide, but which has an amino acid sequence that differs from that peptide. The degree of homology (i.e., percent identity) can be determined, for instance, by comparing sequence information using a computer program optimized for such comparison (e.g., using the GAP computer program, version 6.0 or a higher version, described by Devereux et al. (*Nucleic Acids Res.*, 12, 387 (1984), and freely available from the University of Wisconsin Genetics Computer Group (UWGCG)). The activity of the variant proteins and/or peptides can be assessed, for instance, by examining transduction ability or cell binding ability imparted by a chimeric penton base or fiber protein, or using other methods known to those skilled in the art.

In terms of amino acid residues that are not identical between the variant protein (peptide) and the reference protein (peptide), the variant proteins (peptides) preferably comprise conservative amino acid substitutions, i.e., such that a given amino acid is substituted by another amino acid of similar size, charge density, hydrophobicity/hydrophilicity, and/or configuration (e.g., Val for Phe). The variant site-specific mutations can be introduced by ligating into an expression vector a synthesized oligonucleotide comprising the modified site. Alternately, oligonucleotide-directed site-specific mutagenesis procedures can be used such as disclosed in Walder et al., *Gene*, 42, 133 (1986); Bauer et al., *Gene*, 37, 73 (1985); Craik, *Biotechniques*, 12–19 (January 1995); and U.S. Pat. Nos. 4,518,584 and 4,737,462.

Any appropriate expression vector (e.g., as described in Pouwels et al., *Cloning Vectors: A Laboratory Manual* (Elsevier, N.Y.: 1985)) and corresponding suitable host can be employed for production of recombinant peptides. Expression hosts include, but are not limited to, bacterial species within the genera Escherichia, Bacillus, Pseudomonas, Salmonella, mammalian or insect host cell systems including baculovirus systems (e.g., as described by Luckow et al., *Bio/Technology*, 6, 47 (1988)), and established cell lines such as the COS-7, C127, 3T3, CHO, HeLa, BHK cell line, and the like. An especially preferred expression system for preparing chimeric proteins (peptides) according to the invention is the baculovirus expression system (e.g., as described in Wickham et al. (1995), supra), wherein *Trichoplusia ni*, Tn 5B1-4 insect cells, or other appropriate insect cells, are used to produce high levels of recombinant penton base and/or fiber proteins. The ordinary skilled artisan is, of course, aware that the choice of expression host has ramifications for the type of peptide produced. For instance the glycosylation of peptides produced in yeast or mammalian cells (e.g., COS-7 cells) will differ from that of peptides produced in bacterial cells such as *Escherichia coli*.

Alternately, the peptides of the invention (including the variant peptides) can be synthesized using standard peptide synthesizing techniques well known to those of skill in the art (e.g., as summarized in Bodanszky, *Principles of Peptide*

*Synthesis*, (Springer-Verlag, Heidelberg: 1984)). In particular, the peptides can be synthesized using the procedure of solid-phase synthesis (see, e.g., Merrifield, *J. Am. Chem. Soc.*, 85, 2149–54 (1963); Barany et al., *Int. J. Peptide Protein Res.*, 30, 705–739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the peptide from the resin can be accomplished by, for example, acid treatment at reduced temperature. The peptide-containing mixture can then be extracted, for instance, with dimethyl ether, to remove non-peptide organic compounds, and the synthesized peptides can be extracted from the resin powder (e.g., with about 25% w/v acetic acid). Following the synthesis of the peptide, further purification (e.g., using high performance liquid chromatography (HPLC)) optionally can be done in order to eliminate any incomplete peptides or free amino acids. Amino acid and/or HPLC analysis can be performed on the synthesized peptides to validate the identity of the peptide.

If desired, either the peptides or the proteins of the invention (including the variant peptides or proteins) can be modified, for instance, by glycosylation, amidation, carboxylation, or phosphorylation, or by the creation of acid addition salts, amides, esters, in particular C-terminal esters, and N-acyl derivatives of the peptides of the invention. The peptides also can be modified to create peptide derivatives by forming covalent or noncovalent complexes with other moieties. Covalently-bound complexes can be prepared by linking the chemical moieties to functional groups on the side chains of amino acids comprising the peptides, or at the N- or C-terminus. Such modifications can be particularly useful, for instance, in constructing bispecific molecules having a ligand to a cell surface receptor attached to an antibody. Further modifications will be apparent to those of ordinary skill in the art.

Vector Comprising Adenovirus Proteins

Accordingly, the invention also provides a vector comprising a penton base protein, which optimally is either a wild-type or chimeric adenovirus penton base protein according to the invention. A "vector" is a vehicle for gene transfer as that term is understood by those of skill in the art. Accordingly, preferably the vector further comprises a passenger gene. The vectors according to the invention include, but are not limited to, plasmids, phages, and viruses. Preferably, a vector according to the invention is an adenovirus or baculovirus vector, and optimally is an adenoviral vector. In particular, desirably the vector can comprise a wild-type or chimeric adenovirus penton base protein, and/or a wild-type or chimeric adenovirus fiber protein, and/or a passenger gene as described herein. Hence, the vectors according to the invention are not limited to those that can be employed in the method of the invention, but also include intermediary-type vectors (e.g., "transfer vectors") that can be employed in the construction of gene transfer vectors.

In terms of an adenoviral vector (particularly a replication deficient adenoviral vector), such a vector can comprise either complete capsids (i.e., including a viral genome such as an adenoviral genome) or empty capsids (i.e., in which a viral genome is lacking, or is degraded, e.g., by physical or chemical means). Preferably the viral vector comprises complete capsids, i.e., as a means of carrying one or more passenger genes. Alternately, preferably, a passenger gene is carried into a cell on the outside of the adenoviral capsid. Along the same lines, since methods are available for transferring viruses, plasmids, and phages in the form of their nucleic acid sequences (i.e., RNA or DNA), a vector similarly can comprise RNA or DNA, in the absence of any associated protein such as capsid protein, and in the absence of any envelope lipid. Similarly, since liposomes effect cell entry by fusing with cell membranes, a vector can comprise liposomes, with constitutive nucleic acids encoding the coat protein. Such liposomes are commercially available, for instance, from Life Technologies, Bethesda, Md., and can be used according to the recommendation of the manufacturer. Moreover, a liposome can be used to effect gene delivery wherein the liposome comprises the chimeric adenovirus penton base protein (and/or a chimeric adenovirus fiber protein) as described, for instance, in PCT International Application WO 94/17832. The soluble chimeric coat protein (as produced using methods described herein) can be added to the liposomes either after the liposomes are prepared according to the manufacturer's instructions, or during the preparation of the liposomes.

A vector according to the invention can comprise additional sequences and mutations, e.g., within the adenoviral fiber and/or penton base protein and/or passenger gene sequences. In particular, a vector according to the invention preferably further comprises a nucleic acid comprising a passenger gene. A "nucleic acid" is a polynucleotide (DNA or RNA). A "gene" is any nucleic acid sequence coding for a protein or a nascent RNA molecule. A "passenger gene" is any gene which is not typically present in and is subcloned into a vector (particularly an adenoviral vector) according to the present invention, and which upon introduction into a host cell is accompanied by a discernible change in the intracellular environment (e.g., by an increased level of deoxyribonucleic acid (DNA), ribonucleic acid (RNA), peptide or protein, or by an altered rate of production or degradation thereof). A "gene product" is either an as yet untranslated RNA molecule transcribed from a given gene or coding sequence (e.g., mRNA or antisense RNA) or the polypeptide chain (i.e., protein or peptide) translated from the mRNA molecule transcribed from the given gene or coding sequence. Whereas a gene comprises coding sequences plus any non-coding sequences, a "coding sequence" does not include any non-coding (e.g., regulatory) DNA. A gene or coding sequence is "recombinant" if the sequence of bases along the molecule has been altered from the sequence in which the gene or coding sequence is typically found in nature, or if the sequence of bases is not typically found in nature. According to this invention, a gene or coding sequence can be wholly or partially synthetically made, can comprise genomic or complementary DNA (cDNA) sequences, and can be provided in the form of either DNA or RNA.

Non-coding sequences or regulatory sequences include promoter sequences. A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription is also termed a "silencer". Enhancers differ from DNA-binding sites for sequence-specific DNA binding proteins found only in the promoter (which are also termed "promoter elements") in that enhancers can function in either orientation, and over distances of up to several kilobase pairs, even from a position downstream of a transcribed region. According to the invention, a coding sequence is "operably linked" to a promoter (e.g., when both the coding sequence and the promoter constitute a passenger gene) when the promoter is capable of directing transcription of that coding sequence.

Accordingly, a "passenger gene" can be any gene, and desirably is either a therapeutic gene or a reporter gene.

Preferably a passenger gene is capable of being expressed in a cell in which the vector has been internalized. For instance, the passenger gene can comprise a reporter gene, or a nucleic acid sequence which encodes a protein that can in some fashion be detected in a cell. The passenger gene also can comprise a therapeutic gene, for instance, a therapeutic gene which exerts its effect at the level of RNA or protein. For instance, a protein encoded by a transferred therapeutic gene can be employed in the treatment of an inherited disease, such as, e.g., the cystic fibrosis transmembrane conductance regulator cDNA for the treatment of cystic fibrosis. The protein encoded by the therapeutic gene can exert its therapeutic effect by resulting in cell killing. For instance, expression of the gene in itself can lead to cell killing, as with expression of the diphtheria toxin A gene, or the expression of the gene can render cells selectively sensitive to the killing action of certain drugs, e.g., expression of the HSV thymidine kinase gene renders cells sensitive to antiviral compounds including acyclovir, gancyclovir and FIAU (1-(2-deoxy-2-fluoro-β-D-arabinofuranosil)-5-iodouracil).

Moreover, the therapeutic gene can exert its effect at the level of RNA, for instance, by encoding an antisense message or ribozyme, a protein which affects splicing or 3' processing (e.g., polyadenylation), or can encode a protein which acts by affecting the level of expression of another gene within the cell (i.e., where gene expression is broadly considered to include all steps from initiation of transcription through production of a processed protein), perhaps, among other things, by mediating an altered rate of mRNA accumulation, an alteration of mRNA transport, and/or a change in post-transcriptional regulation. Thus, the use of the term "therapeutic gene" is intended to encompass these and any other embodiments of that which is more commonly referred to as gene therapy and is known to those of skill in the art. In particular, preferably a therapeutic gene is one having therapeutic utility.

The invention also preferably provides a recombinant adenovirus, wherein the adenovirus comprises either a wild-type or chimeric penton base protein, and the adenovirus further comprises a chimeric adenovirus fiber protein, as described herein. Preferably the chimeric fiber protein comprises a protease cleavage site. Alternately, preferably the adenovirus comprises a chimeric adenovirus fiber protein that is unable to bind to a cell to which wild-type adenovirus fiber protein can bind. For instance, the chimeric adenovirus fiber protein present in the adenovirus can comprise an adenovirus fiber protein that is of a different adenoviral serotype than the remainder of the recombinant adenovirus. Similarly, the chimeric adenovirus fiber protein present in the adenovirus can comprise an adenovirus fiber protein that is of shorter length than the wild-type adenovirus fiber protein. These wild-type and chimeric coat proteins are all as previously discussed. Thus, preferably the invention provides a vector selected from the group consisting of p193 (F5*)Nhe, pGBS 59-100(F5*)Nhe, p193(F5*)Apa, pGBS 59-100(F5*)Apa, p193(F5*) Ppu, PGBS 59-100(F5*)Ppu, p193(F5*)Nco, PGBS 59-100(F5*)Nco, p193(F5*)Try, and pGBS 59-100(F5*)Try.

The means of making the recombinant adenoviral vectors according to the invention are known to those skilled in the art. For instance, recombinant adenovirus comprising a chimeric coat protein such as a penton base and/or fiber protein and the recombinant adenovirus that additionally comprises a passenger gene or genes capable of being expressed in a particular cell can be generated by use of a transfer vector, preferably a viral or plasmid transfer vector, in accordance with the present invention. Such a transfer vector preferably comprises a chimeric adenoviral coat protein gene sequence (i.e., particularly a penton base and/or fiber sequence) as previously described. The chimeric coat protein gene sequence comprises a nonnative (i.e., non-wild-type) sequence in place of the native sequence, which has been deleted, or in addition to the native sequence.

A recombinant chimeric coat protein gene sequence (such as a fiber gene sequence) can be moved to or from an adenoviral vector from or into baculovirus or a suitable prokaryotic or eukaryotic expression vector for expression of mRNA and production of protein, and for evaluation of receptor or protein specificity and avidity, trimerization potential, penton base binding, and other biochemical characteristics. In particular, the method of protein production in baculovirus as set forth in the Examples which follow, and as described in Wickham et al. (1995), supra, can be employed.

Accordingly, the present invention also provides recombinant baculoviral and prokaryotic and eukaryotic expression vectors comprising a chimeric adenoviral coat protein gene sequence (preferably a penton base and/or fiber gene sequence), which also are "transfer vectors" as defined herein. The chimeric coat protein gene sequence (e.g., the penton base and/or fiber gene sequence) includes a nonnative sequence in addition to or in place of a native amino acid sequence, and which enables the resultant chimeric coat protein (e.g., penton base protein) to bind to a binding site other than a binding site bound by the native sequence. By moving the chimeric gene from an adenoviral vector, PCR product or the cloning vector to baculovirus or a prokaryotic or eukaryotic expression vector, high protein expression is achievable (approximately 5–50% of the total protein being the chimeric fiber).

A vector according to the invention further can comprise, either within, in place of, or outside of the coding sequence of a coat protein, additional sequences that impact upon the ability of a coat protein such as fiber protein to trimerize, or comprise a protease recognition sequence. A sequence that impacts upon the ability to trimerize is a sequence that enables trimerization of a chimeric coat protein that is a fiber protein. A sequence that comprises a protease recognition sequence is a sequence that can be cleaved by a protease, thereby effecting removal of the chimeric coat protein (or a portion thereof) and attachment of the recombinant adenovirus to a cell by means of another coat protein. When employed with a coat protein that is a fiber protein, the protease recognition site preferably does not affect fiber trimerization or receptor specificity of the fiber protein. For instance, in one embodiment of the present invention, preferably the fiber protein, or a portion thereof, is deleted by means of a protease recognition sequence, and then the penton base protein is modified to allow binding (either through direct or indirect means) to a cell surface binding site.

In terms of the production of vectors according to the invention (including recombinant adenovirus vectors and transfer vectors), transfer vectors are constructed using standard molecular and genetic techniques such as are known to those skilled in the art. Vectors comprising virions or virus particles (e.g., recombinant adenovirus vectors) are produced using viral vectors in the appropriate cell lines. Similarly, the fiber chimera-containing particles are produced in standard cell lines, e.g., those currently used for adenoviral vectors. Following production and purification, the particles in which fiber is to be deleted or inactivated are rendered fiberless or inactive through digestion of the particles with a sequence-specific protease, which cleaves the fiber proteins and releases them from the viral particles to generate fiberless particles. These resultant particles then can be targeted to specific tissues via the penton base or other coat protein, preferably such other coat protein that comprises one or more nonnative amino acid sequences according to the invention.

Illustrative Uses

A vector of the present invention, particularly one complexed with a bispecific molecule, has utility in vitro. Such a vector can be used as a research tool in the study of adenoviral attachment and infection of cells and in a method of assaying binding site-ligand interaction. Similarly, an adenoviral vector, particularly one complexed with a bispecific molecule, can be employed in vivo.

In particular, recombinant adenoviruses of the present invention can be used to treat any one of a number of diseases by delivering to targeted cells corrective DNA, i.e., DNA encoding a function that is either absent or impaired, or a discrete killing agent, e.g., DNA encoding a cytotoxin that, for example, is active only intracellularly, or DNA encoding ribozymes or antisense molecules, for example. Accordingly, use of the term "passenger gene" (e.g., as encoding a "therapeutic agent") is intended to encompass these and other embodiments of that which is more commonly referred to as gene therapy and is known to those of skill in the art. Diseases that are candidates for such treatment include, for example, cancer, e.g., melanoma or glioma, cystic fibrosis, genetic disorders, and pathogenic infections, including HIV infection.

For instance, a recombinant adenovirus having a penton base molecule recognized by $\alpha_v\beta_3$ receptors can be used to treat melanoma or glioma, and a recombinant adenovirus recognized by $\alpha_3\beta_1$ receptors and expressing the cystic fibrosis transmembrane regulator (CFTR) gene can be used to treat cystic fibrosis by delivery to the epithelial cells of the lungs. Furthermore, various blood-related diseases can be treated by using a recombinant adenovirus recognized by $\alpha_m\beta_2$ receptors to target neutrophils and macrophages, a recombinant adenovirus recognized by $\alpha_4\beta_1$ receptors to target lymphocytes, a recombinant adenovirus recognized by $\alpha_{IIb}\beta_3$ receptors to target platelets and megakaryocytes, and a recombinant adenovirus recognized by $\alpha_v\beta_3$ integrins to target endothelial cells undergoing angiogenesis.

The $\alpha_v$ integrins are promising tissue-specific receptors for targeted gene therapy. $\alpha_v$ integrin expression is activated in a majority of melanomas (Albelda et al., *Cancer Res.*, 50, 6757–6764 (1990)) and gliomablastomas (Gladson et al., *J. Clin. Invest.*, 88, 1924 (1991)). Targeting therapeutic adenovirus to the $\alpha_v$ integrins on these cells allows delivery of a toxic gene, for example, while avoiding gene delivery to healthy, surrounding tissue. Furthermore, the integrin $\alpha_v\beta_3$ is expressed on proliferating endothelial cells (Brooks et al., *Science*, 264, 569–571 (1994); Brooks et al., *Cell*, 79, 1157–1165 (1994)). Targeting the $\alpha_v\beta_3$ receptor on these cells can be useful in preventing their proliferation, such as in reduction of tumor growth or treatment of retinal disease, or to promote further vascularization, such as the promotion of revascularization of ischemic tissue.

Moreover, other cells (particularly cells which adenovirus typically does not infect) can be targeted using the method of the invention, for instance, by increasing the efficiency of entry into these cells. In particular, adenovirus can be targeted to peripheral blood T lymphocytes. This can be accomplished by a variety of means, preferably by using a bispecific molecule that attaches an adenovirus to a molecule (e.g., an antibody) that selectively binds the CD3 receptor.

Other applications of the method and constituents of the present invention will be apparent to one skilled in the art.

Means of Administration

The vectors of the present invention can be employed to contact cells either in vitro or in vivo. According to the invention "contacting" comprises any means by which a vector is introduced intracellularly; the method is not dependent on any particular means of introduction and is not to be so construed. Means of introduction are well known to those skilled in the art, and also are exemplified herein.

Accordingly, introduction can be effected, for instance, either in vitro (e.g., in an ex vivo type method of gene therapy or in tissue culture studies) or in vivo by electroporation, transformation, transduction, conjugation or triparental mating, (co-)transfection, (co-)infection, membrane fusion with cationic lipids, high velocity bombardment with DNA-coated microprojectiles, incubation with calcium phosphate-DNA precipitate, direct microinjection into single cells, and the like. Similarly, the vectors can be introduced by means of cationic lipids, e.g., liposomes. Such liposomes are commercially available (e.g., Lipofectin®, Lipofectamine™, and the like, supplied by Life Technologies, Gibco BRL, Gaithersburg, Md.). Moreover, liposomes having increased transfer capacity and/or reduced toxicity in vivo (see, e.g., PCT International Patent Application WO 95/21259) can be employed in the present invention. Other methods also are available and are known to those skilled in the art.

One skilled in the art will appreciate that suitable methods of administering a vector (particularly an adenoviral vector) of the present invention to an animal for purposes of gene therapy (see, for example, Rosenfeld et al., *Science*, 252, 431–434 (1991); Jaffe et al., *Clin. Res.*, 39(2), 302A (1991); Rosenfeld et al., *Clin. Res.*, 39(2), 311A (1991); Berkner, *BioTechniques*, 6, 616–629 (1988)), chemotherapy, and vaccination are available, and, although more than one route can be used for administration, a particular route can provide a more immediate and more effective reaction than another route. Pharmaceutically acceptable excipients also are well-known to those who are skilled in the art, and are readily available. The choice of excipient will be determined in part by the particular method used to administer the vector. Accordingly, there is a wide variety of suitable formulations for use in the context of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, emulsions, gels, and the like containing, in addition to the active ingredient, such excipients as are known in the art.

A vector of the present invention, alone or in combination with other suitable ingredients, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, a vector of the present invention can be made into suppositories by mixing with a variety of bases such as emulsifying bases or water-soluble bases.

Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the gene of interest, the composition employed, the method of administration, and the particular site and organism being treated. However, preferably a dose corresponding to an effective amount of a vector (e.g., an adenoviral vector according to the invention) is employed. An "effective amount" is one that is sufficient to produce the desired effect in a host, which can be monitored using several end-points known to those skilled in the art. For instance, one desired effect is nucleic acid transfer to a host cell. Such transfer can be monitored by a variety of means, including, but not limited to, a therapeutic effect (e.g., alleviation of some symptom associated with the disease, condition, disorder or syndrome being treated), or by further evidence of the transferred gene or coding sequence or its expression within the host (e.g., using the polymerase chain reaction, Northern or Southern hybridizations, or transcription assays to detect the nucleic acid in host cells, or using immunoblot analysis, antibody-mediated detection, or particularized assays to detect protein or polypeptide encoded by the transferred nucleic acid, or impacted in level or function due to such transfer). One such particularized assay described in the Examples which follow includes an assay for expression of the β-glucuronidase gene. These methods described are by no means all-inclusive, and further methods to suit the specific application will be apparent to the ordinary skilled artisan.

Generally, to ensure effective transfer of the vectors of the present invention, it is preferable that about 1 to about 5,000 copies of the adenoviral vector according to the invention be employed per cell to be contacted, based on an approximate number of cells to be contacted in view of the given route of administration, and even more preferable that about 3 to about 300 pfu enter each cell. However, this is just a general guideline which by no means precludes use of a higher or lower amount, as might be warranted in a particular application, either in vitro or in vivo. For example, the actual dose and schedule can vary depending on whether the composition is administered in combination with other pharmaceutical compositions, or depending on interindividual differences in pharmacokinetics, drug disposition, and metabolism. Similarly, amounts can vary in in vitro applications depending on the particular cell type utilized or the means by which the vector is transferred. One skilled in the art easily can make any necessary adjustments in accordance with the necessities of the particular situation.

EXAMPLES

The following examples further illustrate the present invention, and, of course, should not be construed as in any way limiting its scope.

Example 1

This example describes the construction of the adenoviral transfer vector (pAT) for making chimeric penton base molecules.

pAT, a partial restriction map of which is shown in FIG. 1, was created by cloning the unique Bam HI/Pme I fragment (13259–21561) from the Ad5 genome into pNEB 193 R1-, a minor derivative of pNEB 193 (New England Biolabs, Beverly, Mass.), from which the unique Eco RI restriction site was removed [SEQ ID NO:7]. The resulting vector was called pNEB 193 R1- [Ad5 (Bam HI/Pme I)].

Two pairs of PCR primers were synthesized and used to amplify a region upstream (left side) and a region downstream (right side) from the RGD sequence. A unique Spe I site Was inserted into the antisense primer (A5a(15147)S [SEQ ID NO:16]) used to amplify the upstream region between the RGD sequence and a Bst XI site (15017). The Bst XI site is 35 bp upstream from the penton base start codon (15052). A unique Spe I site was also inserted into the sense primer (A5a(15204)S [SEQ ID NO:15]) to amplify the right side of the gene between the RGD amino acid sequence and an Asc I site (15671). The antisense primer (A5a (15659)) used to amplify the right side of the gene is shown as SEQ ID NO:14. The sense primer (A5s(14153)E [SEQ ID NO:13]) for the left side of the gene includes the naturally occurring Bst XI site (15017) and also contains a unique Eco RI site 13 bp upstream from the penton base start codon, which is not in the original sequence. Using these primers, the left and right sides of the penton base gene were amplified and then cloned into pNEB 193 R1' [Ad5 (Bam HI/Pme I)] to create the pAT vector.

The net results of this cloning were the generation of a unique Eco RI site just upstream of the penton base start codon (i.e., [SEQ ID NO:5], which codes for the amino acid sequence of [SEQ ID NO:6]) to facilitate subcloning into a baculovirus transfer vector and to facilitate the generation of a recombinant adenovirus using the pAT vector; the deletion of an 8 amino acid region within the wild-type penton base containing the $\alpha_v$ integrin binding domain comprising from the first His residue to the first Phe residue in the sequence of [SEQ ID NO:11], which itself codes for the amino acid sequence of [SEQ ID NO:12]); and the incorporation of a unique I site encoding the amino acids threonine and serine in place of the deleted region [SEQ ID NO:9], which encodes the amino acid sequence of [SEQ ID NO:10]), so that alternative DNA sequences encoding receptor-binding amino acid motifs or other sequences of amino acids can be inserted at that site.

Example 2

Figure 2:
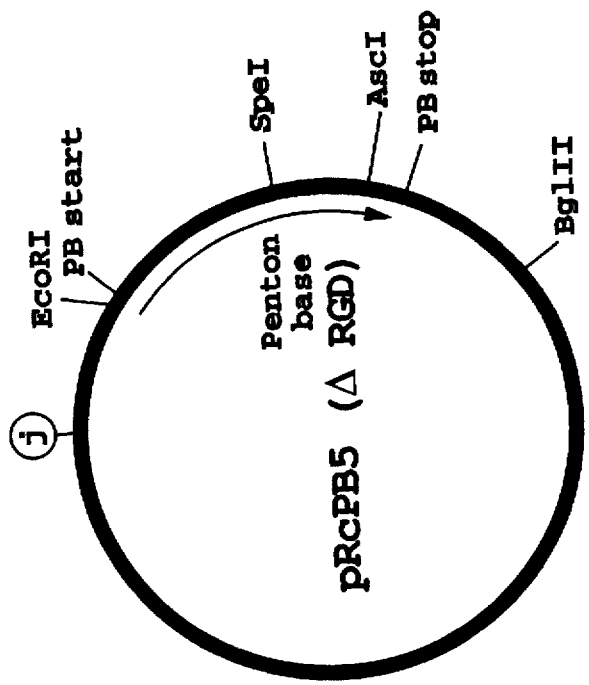
FIG. 2 is a partial restriction map of the vector pRcPB5 (ΔRGD).

This example describes the construction of the base vector pRcPB5 (ΔRGD) for all cloning used to make a recombinant baculovirus for the expression of a recombinant chimeric Ad5 penton base protein (rcPB5 protein) and for making rcPB5 genes for incorporation into pAT and other related vectors.

pRcPB5 (ΔRGD) (Wickham et al., Gene Therapy, 2, 750–756 (1995)), a partial restriction map of which is shown in FIG. 2, was created by cloning the Eco RI/Bgl II fragment from pAT into the baculovirus transfer vector pAcSG2 (Pharmingen, San Diego, Calif.). The resulting plasmid comprises a mutated penton base encoding an eight amino acid deletion of the RGD $\alpha_v$ integrin binding domain which is replaced by a unique Spe I restriction site. A new sequence encoding a receptor binding domain is inserted into the unique Spe I site within the penton base gene in pRcPB5 (ΔRGD). The resulting vector is then used to generate recombinant baculovirus constructs so that rcPB5 protein can be generated in large quantities and evaluated. Based on evaluation of the recombinant protein, the Eco RI/Bgl II fragment from the pRcPB5 derivative is then cloned into pAT to make the recombinant adenovirus (Ad5 rcPB).

Example 3

This example describes the cloning of integrin-specific sequences into the Spe I site of the pRcPB5 (ΔRGD) vector of Example 2.

A sequence recognized by a specific integrin receptor is cloned into the penton base cassette as follows. Overlapping sense and antisense oligonucleotides encoding a desired integrin-specific sequence are synthesized. For example, the overlapping sense (Beta 3RGDs [SEQ ID NO:19]) and antisense (Beta 3RGDa [SEQ ID NO:20]) oligonucleotides that encode sequences that are specific for the integrin $\alpha_v\beta_3$ (i.e., [SEQ ID NO:17], which codes for the amino acid sequence of [SEQ ID NO:18]) and the overlapping sense (CS-1s [SEQ ID NO:23]) and antisense (CS-1a [SEQ ID NO:24]) oligonucleotides that encode nucleic and amino acid sequences that are specific for the integrin $\alpha_4\beta_1$ (i.e., [SEQ ID NO:21] and [SEQ ID NO:22], respectively) are synthesized. The sense and antisense sequences for each are mixed and converted to full-length double-stranded sequences by filling in the unpaired nucleotides with Klenow fragment. The resulting double-stranded sequence is then inserted into the Spe I site of the pRcPB5 (ΔRGD) vector following digestion with the endonucleases Xba I and Spe I. The resulting vectors, pRcPB5 ($\alpha_v\beta_3$) and pRCPB5 ($\alpha_4\beta_1$), are used to create the recombinant baculovirus vectors, AcNPV rcPB5($\alpha_v\beta_3$) and AcNPV rcPB5($\alpha_4\beta_1$). The rcPB5 protein produced in insect cells using the aforementioned baculovirus vectors is evaluated as described above. Based on the analyses in the baculovirus expression system, the Eco RI/Bgl II fragment from each of the vectors then is cloned into a pAT vector to produce the adenoviral vectors, pAT rcPB5 ($\alpha_v\beta_3$) and pAT rcPB5 ($\alpha_4\beta_1$).

Example 4

This example describes the creation of recombinant adenovirus particles containing a wild-type fiber protein and a chimeric penton base specific for $\alpha_4$ integrins (Ad5 rcPB5 ($\alpha_4$):wtFiber).

A chimeric penton base specific for $\alpha_4$ integrin (Ad5 rcPB5 ($\alpha_4$):wtFiber) can be constructed through ligation of plasmid DNA with viral DNA, which chimeric construct then can be transfected into cells using standard methods. The pAT vector containing the desired chimeric form of penton base is digested with Xmn I to generate a 1 kb piece of DNA containing the receptor-specific coding sequence. Ad5 DNA is digested with the restriction endonuclease Xmn I, which cuts wild-type Ad5 at positions 14561 and 15710 within the Ad5 genome. The two larger fragments are purified away from the smaller 1 kb piece containing the sequence encoding RGD and then ligated with the Xmn I fragment from the pAT vector. The ligated fragments are then transfected into the appropriate cell line to produce recombinant virus. The virus produced from the cells can be plaque purified and verified to contain the chimeric penton base gene using PCR. The penton base produced in the Ad5-infected cells can be also purified, and its receptor-specificity verified.

Example 5

This example describes the creation of recombinant adenovirus particles containing wild-type fiber protein and chimeric penton base specific for $\alpha_4$ integrins (Ad5 rcPB5 ($\alpha_4$):wtFiber). Analogous adenovirus particles can be constructed which comprise the wild-type fiber protein and chimeric penton base using a modification of this approach.

Adenovirus particles having a chimeric penton base specific for $\alpha_4$ integrins (Ad5 rcPB5 ($\alpha_4$):wtFiber) can be constructed through transfection of plasmid DNA and viral DNA into cells and generation of recombinants through homologous recombination. The pAT vector containing the desired chimeric form of penton base is linearized by digestion with Bam HI. Ad5 DNA is digested with the restriction endonuclease Xmn I which cuts wild-type Ad5 at positions 14561 and 15710 within the Ad5 genome. These two unique sites within the Ad5 genome flank the Spe I site in the pAT vector. The linearized pAT vector and the Xmn I-digested Ad5 DNA are then transfected into the appropriate cell line, such as 293 cells, to produce a recombinant virus by homologous recombination. The virus produced from such cells can be plaque purified and verified to contain the chimeric penton base gene using PCR. The penton base produced in Ad5-infected cells also can be purified, and its receptor-specificity verified.

Example 6

This example describes the creation of recombinant adenovirus particles that contain chimeric penton base specific for $\alpha_4$ integrins (Ad5 rcPB5 ($\alpha_4$):-Fiber), and that contain shortened fiber protein or chimeric fiber protein with a protease cleavage site. Analogous adenovirus particles can be constructed which comprise the wild-type fiber protein and chimeric penton base using a modification of this approach.

The Ad5 rcPB5 ($\alpha_4$):wtFiber viral DNA can be digested with Bam HI and the 0–59 map unit (m.u.) fragment purified. The fiber gene can be deleted from plasmid containing the Ad5 Bam HI/Sal I fragment (genome map units 59–100). The resultant plasmid is then digested with Bam HI and Sal I, ligated to the 0–59 m.u. piece of Ad5 rcPB5 ($\alpha_4$):wtFiber DNA, and transfected into cells expressing $\alpha_4$ integrins. The $\alpha_4$ integrins can serve as both the attachment and internalization receptors for the Ad5 rcPB5 ($\alpha_4$):-Fiber virus.

Example 7

This example describes the creation of recombinant adenovirus particles containing chimeric fiber protein specific for sialyl Lewis X antigen and chimeric penton base specific for $\alpha_4$ integrins Ad5 rcPB5 (a$_4$):rcFiber (sLX)]. Analogous adenovirus particles can be constructed which comprise the wild-type fiber protein and chimeric penton base using a modification of this approach.

The protein P-selectin binds to sialyl Lewis X antigen present on lymphocytes. The binding domain from P-selectin is present on the rcFiber (sLX) protein to mediate virus binding. The left arm (0–59 m.u.) of the Ad5 rcPB5 ($\alpha_4$):wtFiber virus can be prepared by Bam HI digestion and then purified.

The rcFiber (sLX) gene can be cloned into the plasmid containing the 59–100 m.u. fragment of the Ad5 genome. The rcFiber (sLX) gene then can replace the wtFiber gene. The 59–100 m.u. Ad5 fragment containing rcFiber (sLX) then can be ligated to the 0–59 m.u. Ad5 fragment containing rcPB5 ($\alpha_4$). The ligated fragment then can be transfected into cells expressing the receptors for attachment (sialyl Lewis X) and internalization ($\alpha_4$ integrins) for the chimeric virus Ad5 rcPB5 ($\alpha_4$):rcFiber (sLX).

Example 8

This example describes the creation of recombinant adenovirus particles containing chimeric hexon protein specific for sialyl Lewis X antigen, chimeric penton base specific for $\alpha_4$ integrins, and shortened fiber protein [Ad5 rcPB5 ($\alpha_4$):-Fiber:rcHexon (sLX)] or fiber protein containing a protease cleavage site. Analogous adenovirus particles can be constructed which comprise any of the wild-type (i.e., native) versions of these proteins, and any combination of the wild-type and chimeric proteins using a modification of this approach.

The protein P-selectin binds to sialyl Lewis X antigen present on lymphocytes. The binding domain from P-selection is present within an exposed loop on wtHexon, and the resultant rcHexon (sLX) protein can mediate virus binding. Genes encoding rcPB5 ($\alpha_4$) and rcHexon (sLX) can be cloned into the pAT vector that contains the penton base gene and the region encoding the exposed loop of hexon protein. A ligation of three fragments can be performed to generate the recombinant virus. Ad5 rcPB5 ($\alpha_4$):-Fiber virus can be digested with Eco RI and Bam HI. The left end of the genome up to the Eco RI site and the right end of the genome down to the Bam HI site can be purified and ligated with the Eco RI/Bam HI fragment from the pAT vector containing rcPB5 ($\alpha_4$) and rcHexon (sLX). The ligated fragment then can be transfected into cells expressing the receptors for attachment (sialyl Lewis X) and internalization ($\alpha_4$ integrins) for the chimeric virus Ad5 rcPB5 ($\alpha_4$):rcFiber (sLX).

Example 9

This example describes the production of wild-type Ad5 and mutant rcPB5 ($\Delta$RGD) penton base proteins in baculovirus.

Using PCR, the wild-type Ad5 penton base sequence was amplified with an Eco RI site inserted at the 5' end of the gene. This gene was then cloned into the pAT vector and then subcloned into the pAcSG2 baculoviral transfer vector, using methods known in the art. Recombinant baculovirus encoding the Ad5 penton base gene (AcNPV wtPB5) produced levels of penton base protein in insect cells that constituted approximately 50% of the total cellular protein. The purified wtPB5 protein migrated consistently with respect to its known molecular weight on sodium dodecyl sulfate (SDS)-polyacrylamide gel electrophoresis (PAGE) and can mediate cell adhesion like Ad2 penton base (Wickham et al. (1993), supra).

The core baculoviral transfer vector, pRcPB5 ($\Delta$RDG), for expression of rcPB5 protein in the baculoviral expression system, has been used to make recombinant baculovirus, which expresses rcPB5 protein. This rcPB5 protein, rcPB5 ($\Delta$RGD), contains an 8 amino acid deletion in the RGD region as shown in FIG. 2, which is a partial restriction map of the vector pRcPB5 ($\Delta$RGD). This protein migrates consistently with respect to its known molecular weight on SDS-PAGE and, in contrast to the wild-type protein (wtPB5), does not mediate cell adhesion, which is consistent with its lack of the RGD cell adhesion motif. Chimeric recombinant penton base molecules rcPB5 ($\alpha_v\beta_3$) and rcPB5 ($\alpha_4$), each containing inserts specific for $\alpha_v\beta_3$ and $\beta_4$ integrins, respectively, also have been produced via the core baculoviral transfer vector, pRcPB5 ($\Delta$RGD). The rcPB5 ($\alpha_v\beta_3$) protein mediates epithelial cell ($\alpha_v$+, $\alpha_4$–), but not lymphocyte ($\alpha_v$–, $\alpha_4$+), adhesion; in contrast, RcPB5 ($\alpha_4$) supports lymphocyte, but not epithelial cell, adhesion.

Example 10

This example describes the targeting of adenovirus to lymphocytes.

The transfer vectors pAT ($\alpha_v\beta_3$) and pAT ($\alpha_4$) were constructed by cloning the Eco RI/Bgl II fragments from their respective pRcPB5 vectors into the pAT ($\Delta$RGD) vector. These pAT vectors were then linearized by Bam HI digestion and transfected with Xmn I-digested viral DNA from an Ad5 variant, which lacks the E1 and E3 regions and contains a $\beta$-galactosidase reporter gene under the control of a cytomegalovirus (CMV) promoter, to obtain recombinant Ad5 virus, namely Ad5 rcPB ($\Delta$RGD), Ad5 rcPB ($\alpha_v\beta_3$), and Ad5 rcPB ($\alpha_4$), through homologous recombination. The Xmn I endonuclease cuts the wild-type Ad5 at positions 14561 and 15710 within the genome, while the Bam HI/Pme I fragment contained in the pAT vector spans the Ad5 region of 13258 to 21562. Thus, the regions of homologous overlap between the left and right viral sequences with the Bam HI/Pme I fragment are 1303 bp and 5851 bp, respectively. The presence of the chimeric inserts in the Ad5 rcPB ($\alpha_v\beta_3$) and Ad5 rcPB ($\alpha_4$) viruses are verified through PCR.

The recombinant adenovirus Ad5 rcPB ($\alpha_4$) is analyzed for its targeting potential in relation to wild-type Ad5 and recombinant Ad5 rcPB ($\Delta$RGD) by measuring levels of the reporter gene expression in cells exposed to each of the viruses. Delivery of B-galactosidase to the B-lymphocyte cell line, Ramos, is significantly higher using the Ad5 rcPB ($\alpha_4$) virus than the Ad5 rcPB ($\Delta$RGD) and wild-type Ad5 viruses. Conversely, delivery of $\beta$-galactosidase to an epithelial-derived cell line is significantly higher than the wild-type Ad5 virus in comparison to the Ad5 rcPB ($\alpha_4$) and Ad5 rcPB ($\Delta$RGD) viruses.

These results confirm that changes in penton base protein that redirect the protein to interact with a new receptor can be utilized to target the virus to new cells and tissues while generally avoiding delivery to other cells and tissues.

Example 11

This example describes the binding of adenovirus to various cells.

Many tissues have been reported to be transducible by adenovirus. However, the relative transduction efficiencies of different tissues compared to host epithelial cells is not generally known. Smooth muscle cells and endothelial cells are clinically relevant targets for gene therapy in order to prevent restenosis of angioplastied arteries, and to promote or to prevent angiogenesis (Mazur et al., *Tex. Heart Inst. J.*, 21, 104–111 (1994)). These cell types have previously been reported to be transducible by adenovirus (Lemarchand et al., *Proc. Natl. Acad. Sci.*, 89, 6482–6486 (1992); Schulick et al., *Circ. Res.*, 77, 475–485 (1995)). However, experiments have revealed smooth muscle and endothelial cells to be much less efficiently transduced than many epithelia-derived cells. Accordingly, the binding of adenovirus to various cells of different cell lines was investigated.

In these studies, and those of the Examples which follow, various viruses and cell lines were employed. The A549 human alveolar carcinoma cells, 293 human embryonic kidney cells (293 cells), primary human venule endothelial cells (HuVEC), and primary human intestinal smooth muscle cells (HISMC) were obtained from American Tissue Culture Collection (ATCC; Rockville, Md.). Primary aortic smooth muscle cells (HASMC) were obtained from Cell Systems (Kirkland, Wash.). The A549 and 293 cells were maintained in Dulbecco's modified Eagles medium (DMEM) supplemented with 5% calf serum (GIBCO, BRL, Grand Island, N.Y.). The primary cells, i.e., HuVEC, HISMC, and HASMC cells, were maintained in MCDB medium (GIBCO, BRL) supplemented with 10% fetal bovine serum and bovine pituitary extract (BPE) (GIBCO, BRL).

The relative transduction efficiencies of primary human intestinal smooth muscle cells (HISMC) and primary human venule endothelial cells (HuVEC) were compared to the transduction efficiency of A549 alveolar carcinoma cells using the recombinant adenovirus vector Ad5CMVGlu. Ad5CMVGlu contains deletions of the E1 and E3 regions of the genome, and contains the β-glucuronidase gene present in the deleted E1 region under the control of the CMV promoter.

The cells were transduced for these experiments essentially as in other examples. Briefly, confluent monolayers of A549 cells, HuVEC cells, or HISMC cells in 35-mm wells were preincubated for about 1 hour in the absence or presence of 5 μg/ml of soluble adenovirus fiber protein. Soluble fiber protein was produced as previously described (Wickham et al., *Cell*, 73, 309–319 (1993)). About 20,000 counts per minute (cpm) of [$^3$H]-thymidine-labeled adenovirus was added to each well, and the mixtures were incubated for one hour at 4° C. in a total volume of about 0.3 ml of culture medium. Cells transduced with radiolabeled adenovirus were washed three times, and the total cell-associated counts were measured in duplicate in a scintillation counter.

Adenovirus was radiolabeled by adding 50 μCi/ml [$^3$H]-methyl thymidine (Amersham Corp., Arlington Heights, Ill.) to the medium of infected cells at about 20 hours following their infection at a multiplicity of infection (MOI) of 5. The infected cells were then harvested at about 48 to 60 hours post-infection, and the virus was purified by three freeze-thaw cycles followed by two successive bandings on CsCl gradients. Purified virus was then dialyzed with 10 mM Tris-buffered saline, pH 7.8, containing 10 mM MgCl$_2$ and 2% sucrose, and was frozen at about −80° C. Scintillation counting was used to determine cpm. The activity of the labeled viruses was approximately 10$^4$ virus particles/cpm.

Figure 3A:
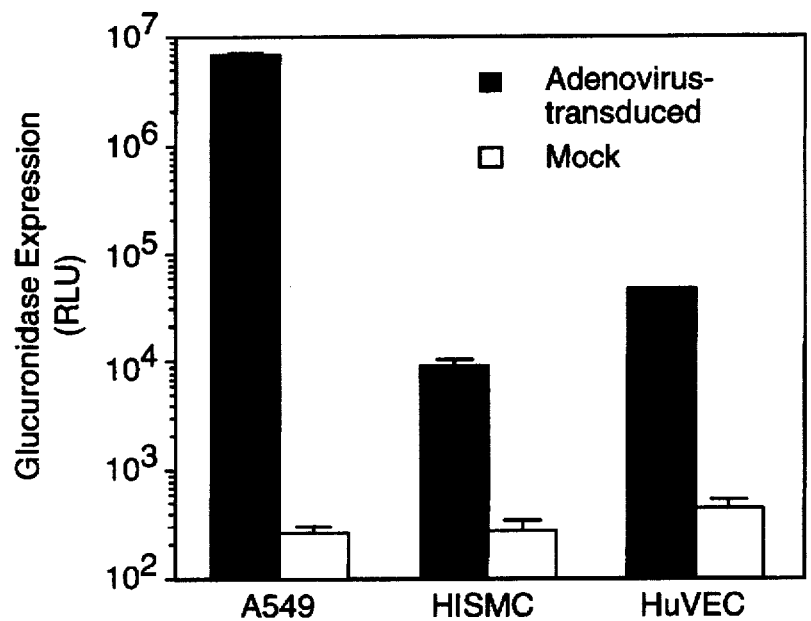
FIGS. 3A–3B are bar charts that depict β-glucuronidase expression (relative light units; RLU) (FIG. 3A) in epithelial (A549), endothelial (HuVEC), and smooth muscle (HISMC) cells either transduced (solid bars) or mock-transduced (open bars) with Ad5CMVGLu, and virus binding (FIG. 3B) to the same cells in either the presence (solid bars) or absence (open bars) of 5 µg/ml of soluble adenovirus fiber protein.
Figure 3B:
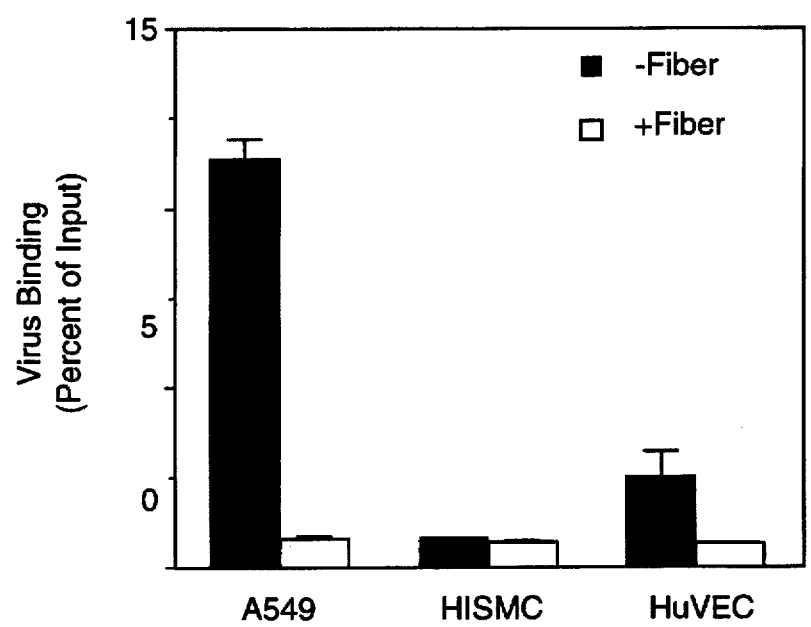

The results of these transduction experiments are depicted in FIGS. 3A–B. As can be seen in FIG. 3A, although gene delivery to smooth muscle and endothelial cells did occur, the relative levels of expression of a transferred reporter gene in these cells were 690- and 130-fold lower, respectively, than the expression levels observed in A549 cells. This reflects a much lower transduction efficiency of smooth muscle and endothelial cells—cells which are prime targets for gene therapy—using adenovirus.

The ability of adenovirus to bind to the three different cell lines in the presence or absence of added soluble adenovirus fiber protein was investigated to assess the role of the fiber receptor in the transduction efficiency of the cells. As depicted in FIG. 3B (solid bars), the A549 cells bound 30- and 10-fold higher amounts of labeled Ad5 compared to smooth muscle and endothelial cells, respectively. Whereas over 95% of the A549 binding was inhibited by recombinant adenovirus fiber protein, the binding of Ad5 to HISMC and HuVEC was relatively unaffected by competing fiber protein (open bars). This confirms that the poor transduction efficiency of smooth muscle and endothelial cells is due to a lack of fiber-specific binding of Ad5 to these cells. Moreover, the results indicate that other cells that lack fiber receptor (or high levels of fiber receptor) similarly may present poor targets for adenoviral-mediated gene therapy.

Example 12

This example describes the general scheme and underlying rationale employed for targeting of adenovirus binding to a specific cell surface binding site using a bispecific molecule. The method described herein can be modified for use with a bispecific molecule other than a bispecific antibody.

Figure 4:
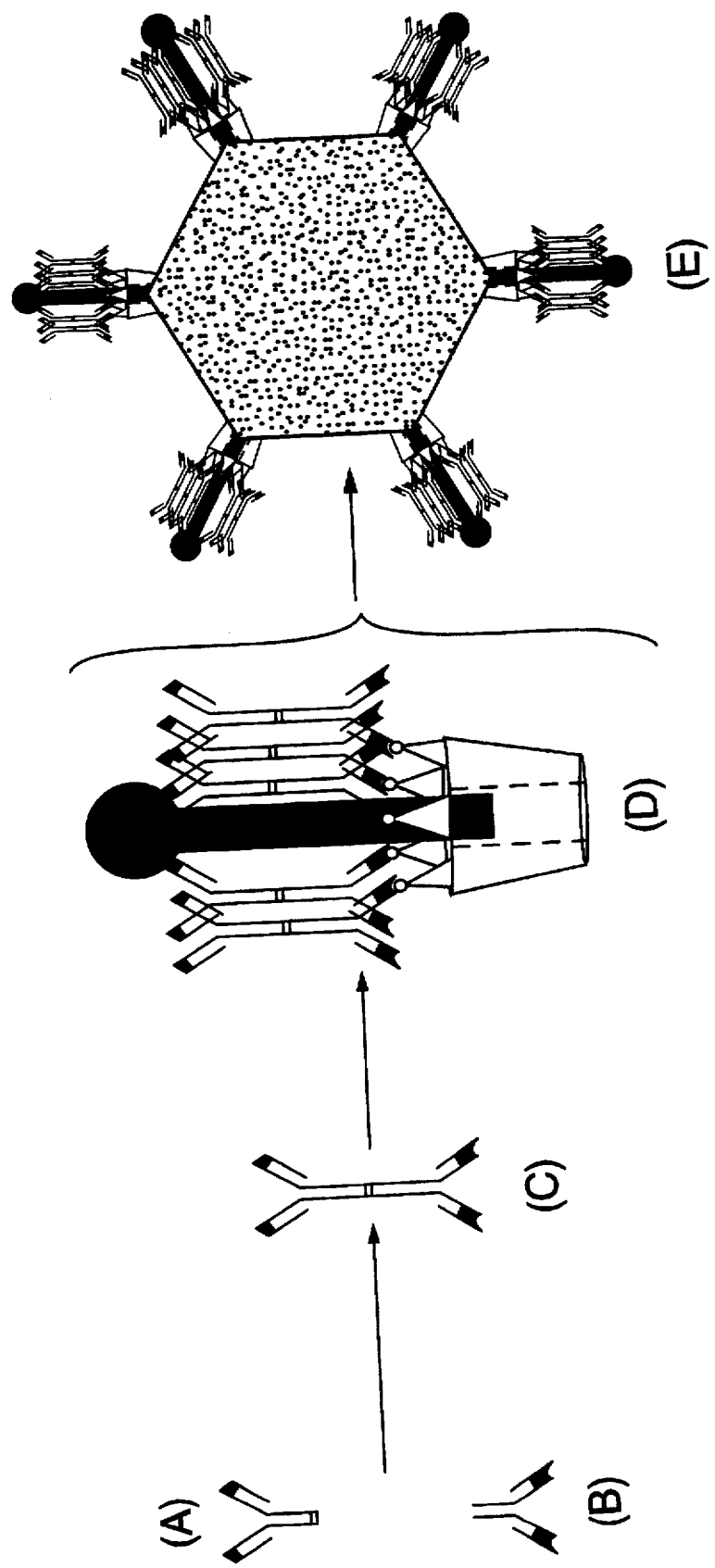
FIG. 4 depicts one embodiment of the method of the invention wherein an antibody directed against a cell surface binding site (A) and an antibody directed against an epitope in penton base protein (B) are chemically linked to comprise a bispecific antibody (C), which is added to an adenovirus comprising the penton base epitope to allow interaction of the penton base and the bispecific antibody (D), and targeting of the adenoviral particle to which the bispecific antibodies are complexed (E) to cells having the cell surface binding site against which the bispecific antibody also is directed.

The possibility of increasing transduction efficiency by increasing adenovirus binding to HISMC and HuVEC cells was investigated in this example. In particular, the possibility of increasing adenovirus binding through the use of a bispecific antibody (bsAb) was explored. Bispecific antibodies (bsAbs) are molecules comprised of two antibodies (monoclonal, polyclonal and/or single-chain) with two different specificities. A bispecific antibody was constructed by David Segal (National Institutes of Health, NIH) that contains one antibody (in this case, a monoclonal antibody (mAb)) having specificity for an epitope incorporated into adenovirus, and another antibody (again, a mAb) having specificity for a receptor present on smooth muscle and endothelial cells (Segal et al., supra). The experiments were done to determine whether by adding the bsAb to the adenovirus vector to create an Ad5/bsAb complex as illustrated in FIG. 4, the binding deficit of those cells which lack high levels of fiber receptor could be overcome.

The bispecific antibody employed in these experiments was constructed by chemically linking the M2 mAb with a L230 mAb. The M2 mAb, directed against the FLAG octapeptide, DYKDDDDK, (i.e., Asp Tyr Lys Asp Asp Asp Asp Lys [SEQ ID NO:25]), was obtained from Kodak (New Haven, Conn.). The L230 mAb, which binds $\alpha_v$ integrins, was obtained from the supernatant of hybridoma cells obtained from the ATCC (Wickham et al., *Gene Therapy*, 2, 750–756 (1995); Weinacker et al., *J. Biol. Chem.*, 269, 6940–6948 (1994)). The L230 mAb was chosen for these studies since smooth muscle and endothelial cells comprise $\alpha_v$ integrins on their cell surface, and adenovirus normally uses $\alpha_v$ integrins to enter cells (Cheresh, *Proc. Natl. Acad. Sci.*, 84, 6471–6475 (1987); Damjanovich et al., *Am. J. Respir. Cell Mol. Biol.*, 6, 197–206 (1992); Wickham et al. (1993), supra). Incorporation of the FLAG peptide into the penton base protein would thereby potentially allow recognition of the adenovirus vector by the L230:FLAG bispecific antibody.

The penton base protein, unlike the fiber protein, normally does not play a role in adenovirus attachment. This presumably is due to steric inhibition by the fiber protein and/or its lower affinity of the Ad5 penton base for $\alpha_v$ integrins compared to the affinity of the fiber protein for its receptor (Wickham et al. (1993), supra). However, any possible steric or affinity restraints imposed on penton base-mediated attachment could potentially be overcome through complexing the L230:FLAG bispecific antibody to an epitope on penton. IgG antibodies typically have high affinity for their epitopes, and the extra length provided by the bispecific antibody potentially could prevent steric inhibition due to the longer length of the fiber protein. The penton was chosen for incorporating an antibody epitope since the RGD binding domain readily can be manipulated at either the DNA or the protein level (Wickham et al. (1995), supra) without impairing the ability to make viable adenovirus vectors (Bai et al., *J. Virol.*, 67, 5198–5205 (1993)). Along these lines, the penton base protein was investigated as a means of commanding cell attachment/cell entry, particularly in the absence of cell binding mediated by adenovirus fiber protein.

Example 13

This example describes the generation of recombinant genes encoding chimeric penton base proteins.

Viruses and plasmids employed in this and subsequent examples were constructed using standard molecular and genetic techniques such as are known to those skilled in the art (e.g., Maniatis et al., *Molecular Cloning: A Laboratory Manual*, 2nd ed. (Cold Spring Harbor, N.Y., 1992); Ausubel et al., *Current Protocols in Molecular Biology*, (1987)), and using commercially available reagents and enzymes according to the recommendations of the manufacturer (e.g., Boehringer Mannheim, Inc., Indianapolis, Ind.; New England Biolabs, Beverly, Mass.; Bethesda Research Laboratories, Bethesda, Md.; etc.). The base baculovirus transfer plasmid, pRcPB5 (ΔRGD), as described in Example 2, was employed to construct vectors comprising chimeric penton base genes. This plasmid contains an adenovirus penton base gene comprising an eight amino acid deletion of the RGD integrin-binding domain and, inserted in the region of the RGD deletion, an Spe I restriction site.

Two types of chimeric penton base genes were constructed: a penton base/FLAG chimera gene (i.e., PB:FLAG), and a control penton base chimeric gene incorporating coding sequence for hemagglutinin peptide (HA) (i.e., PB:HA). The sequence of these genes as compared to the sequence of the wild-type RGD motif-containing penton gene is depicted in Table 1.

TABLE 1

PB:HA and PB:FLAG sequences as compared to the wild-type penton base sequence

Wild-type penton base RGD-containing sequence:
N D H A I R G D T Y R A
(i.e., Asn Asp His Ala Ile Arg Gly Asp Thr Tyr Arg Ala) [SEQ ID NO:37]

PB:HA RGD-containing sequence:
N D T S E A A A H A I R G D <u>T Y P Y D V P D Y A G S S</u> <u>R A</u>
(i.e., Asn Asp Thr Ser Glu Ala Ala Ala His Ala Ile Arg Gly Asp Thr Tyr Pro Tyr Val Pro Asp Tyr Ala Gly Ser Ser Arg Ala) [SEQ ID NO:38]

PB:FLAG RGD-containing sequence:
N D T S E A A A H A I R G D T Y A <u>D Y K D D D D K G S S</u> <u>R A</u>
(i.e., Asn Asp Thr Ser Glu Ala Ala Ala His Ala Ile Arg Gly Asp Thr Tyr Ala Asp Tyr Lys Asp Asp Asp Asp Lys Gly Ser Ser Arg Ala) [SEQ ID NO:39]

As indicated in Table 1, the singly underlined sequences comprised shared wild-type sequences, the RGD motif is bolded, and the double underlined sequences comprise the HA and FLAG epitopes.

The PB:FLAG chimeric gene was constructed by cloning into the penton plasmid pRcPB5 (ΔRGD) an insert containing the original RGD coding sequence juxtaposed to the FLAG peptide coding sequence (Wickham et al. (1995), supra). Additional spacer amino acids were also incorporated into the penton insert to assure availability of the FLAG epitope to the FLAG mAb. In particular, the chimeric FLAG and HA penton genes were created by making use of overlapping sense and antisense DNA oligomers. The synthesized oligomers code for the amino acid sequence TSEAAAHAIRGDTYADYKDDDDKGSS (i.e., Thr Ser Glu Ala Ala Ala His Ala Ile Arg Gly Asp Thr Tyr Ala Asp Tyr Lys Asp Asp Asp Asp Lys Gly Ser Ser [SEQ ID NO:26]) for FLAG, and TSEAAAHAIRGDTYPYDVPDYAGSS (i.e., Thr Ser Glu Ala Ala Ala His Ala Ile Arg Gly Asp Thr Tyr Pro Tyr Asp Val Pro Asp Tyr Ala Gly Ser Ser [SEQ ID NO:27]) for HA. The sense primers contain a 5' Spe I site, and the antisense primers contain a 5' Xba I site. The sense primer employed to create the FLAG and HA chimeric pentons comprised GGACTAGTGAGGCGGCGGC- CCACGCCAT CCGCGGCGACACCTAC [SEQ ID NO:28]. The antisense primer employed to create the HA construct comprised GCTCTAGACCCGGCG- TAGTCGGGCACGTCGTAGGGGTAGGT- GTCGCCGCGGAT [SEQ ID NO:29], and the antisense primer employed to create the FLAG construct comprised GCTCTAGAC CCCTTGTCGTCGTCGTCCTTG- TAGTCGGCGTAGGTGTCGCCGCGGAT [SEQ ID NO:30]. The sense and antisense primers for each insert were mixed and filled in with Klenow fragment. The complete double-stranded inserts were then purified and digested with Xba I and Spe I for cloning into the Spe I site of pRcPB5 (ΔRGD). The orientation of each insert was assessed by Spe I/Asc I digests of the clones. Clones having the correct orientation of the subcloned fragment were then sequenced in the region of the insert.

Example 14

This example describes the production and characterization of the size of the chimeric penton base proteins encoded by the recombinant penton base genes.

Recombinant penton base proteins were produced using a baculovirus expression system as discussed in Example 9. Briefly, recombinant baculovirus employed to express the penton base genes were produced by using standard protocols to transfect Tn5 insect cells with linearized baculovirus DNA along with the baculovirus transfer plasmids described above. The resultant recombinant baculoviruses were used to infect Tn5 cells to produce recombinant protein. The cells were harvested at three days post-infection, and the penton base protein was purified using a POROS HQ anion exchange high performance liquid chromatography (HPLC) column as previously described (Wickham et al. (1995), supra).

The purified recombinant penton base protein PB:FLAG was first immunoprecipitated to determine whether it was recognized by the FLAG mAb and was the correct size. For immunoprecipitation, about $10^6$ Tn5 cells for each sample were infected with the baculovirus vectors producing either the wild-type penton base (i.e., PB:WT) or chimeric FLAG penton base (i.e., PB:FLAG). The cells were harvested and pelleted at three days post-infection. Cells were then resuspended in 0.5 ml of PBS containing 10 μg/ml leupeptin, 10 μg/ml aprotinin, and 1 mM phenylmethylsulfonyl fluoride (PMSF), followed by three freeze-thaw cycles and a final clearing by centrifugation at 15,000×g for 15 minutes. A portion of the lysate was rocked for about two hours at 4° C. with agarose-coupled protein A beads (Sigma, St. Louis, Mo.) that contained either prebound FLAG mAb or control L230 mAb. The agarose complexes were then washed three times with PBS, and were resuspended in about 40 µl of 1 X nonreducing running buffer (i.e., Laemmli buffer). The samples were boiled for three minutes and loaded onto a 10% SDS polyacrylamide gel. The resulting gel was stained with Coomassie blue, destained, and photographed.

The FLAG mAb immunoprecipitated a chimeric PB:FLAG protein that was slightly larger than the purified wild-type penton base protein. This size difference is due to the 18 additional amino acids present in the PB:FLAG chimeric protein as compared to the wild-type protein. The FLAG mAb did not precipitate PB:WT, and the control L230 mAb did not precipitate either PB:FLAG or PB:WT. These results confirm that the chimeric PB:FLAG protein is of the appropriate size, and appropriately combines with the FLAG mAb.

Example 15

This example describes the characterization of the functionality of the RGD domain present in the chimeric penton base proteins encoded by the recombinant penton base genes.

The functionality of the RGD domain in the chimeric proteins was confirmed by assaying cell adhesion to immobilized recombinant penton base using a modification of a previously described method (Wickham et al (1993), supra). Specifically, A549 cells were labeled overnight with [$^3$H]-methyl thymidine. The cells were washed and released from the tissue culture surface using 10 mM EDTA. The cells were then pelleted, washed again, and resuspended in adhesion buffer consisting of DMEM containing 0.5% bovine serum albumin (BSA) and 20 mM N-2-hydroxyethylpiperazine-N'-2-ethanesulfonic acid (HEPES). The labeled cells were added to culture plates comprised of 48-well untreated polystyrene (Costar, Cambridge, Mass.), which had been coated overnight with about 200 µl/well of 1 µg/ml recombinant wild-type penton base or chimeric FLAG penton base in phosphate buffered saline (PBS). The wells were blocked for two hours prior to the addition of labeled cells using a 5% BSA solution in PBS. The cells were allowed to adhere to the coated wells for about 30 minutes at 37° C., followed by washing the wells two times with PBS. Adherent cells were then solubilized in a 1% SDS solution in PBS and counted in a scintillation counter to determine the level of cell adherence. The reported cpm are the average of duplicate samples.

The cell adhesion experiments also were carried out in the presence of antibodies that block integrins. For these experiments, the labeled cells were first incubated at 22° C. with about 50 µg/ml of one of the following antibodies: mAb L230, a function blocking antibody directed against all $\alpha_v$ integrins; mAb P1F6, a function-blocking antibody directed against the integrin $\alpha_v\beta_5$; and mAb 1B1.3.2, a non-function blocking antibody directed against the $\alpha_v$ subunit of $\alpha_v$ integrins. The P1F6 mAb was provided by Dean Sheppard (University of California, San Francisco), and the 1B1.3.2 mAb was provided by Sarah Bodary (Genentech, San Francisco). Following incubation with antibody, the cells were allowed to adhere to the coated wells, and adherent cells were quantified as described above.

Figure 5:
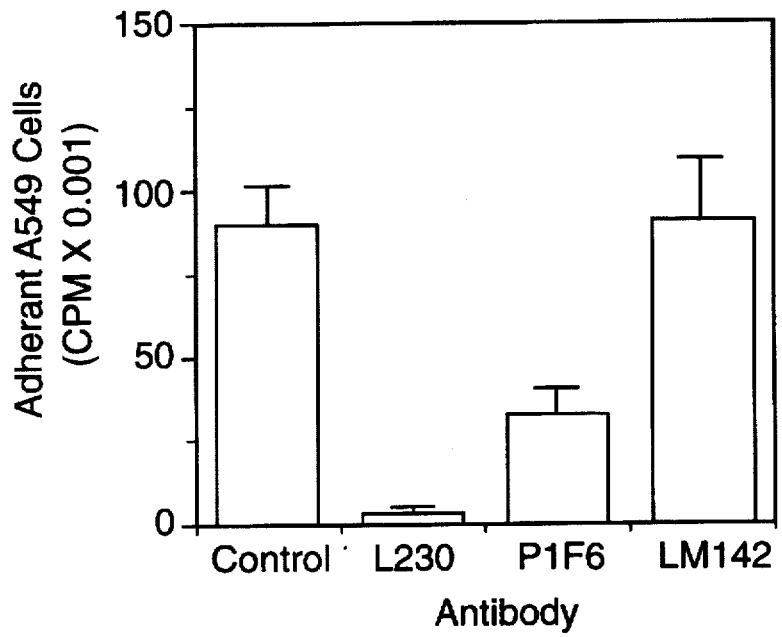
FIG. 5 is a bar chart that depicts inhibition of adhesion of A549 cells to PB:FLAG as measured by adherent cells (CPM×0.001) in the absence (control condition) or presence of the anti-αv antibodies, P1F6 (directed against the integrins $\alpha_v\beta_5$), L230 (directed against all αv integrins), and LM142 (directed against the αv subunit of αv integrins).

As illustrated in FIG. 5, the recombinant penton base protein PB:FLAG coated onto plastic wells mediated the attachment and spreading of A549 cells (control bar). In comparison, pretreatment of the A549 cells with the antibody P1F6 directed against the integrin $\alpha_v\beta_5$ partially blocked adhesion of the cells to the recombinant FLAG penton base protein (P1F6 bar). Pretreatment with the non-function blocking antibody LM142 directed against $\alpha_v$ integrins had no effect on A549 adhesion (LM142 bar). The function-blocking antibody, mAb L230, directed against all $\alpha_v$ integrins including $\alpha_v\beta_3$, $\alpha_v\beta_5$, and $\alpha_v\beta_6$ blocked all adhesion of A549 cells to the FLAG penton base protein (L230 bar). Similar results were obtained using the chimeric penton base protein, PB:HA, which contains the HA epitope. These results thus confirm the functionality of the RGD site in both the PB:FLAG and PB:HA penton base proteins, and the ability of the L230 mAb to recognize $\alpha_v$ integrins.

Example 16

This example describes the characterization of the recombinant FLAG penton base protein to determine whether the FLAG mAb could block recognition of PB:FLAG by $\alpha_v$ integrins.

The close proximity of the FLAG epitope to the RGD domain created a possibility that the RGD site would be sterically blocked upon binding of the FLAG mAb to the recombinant chimeric penton base protein. Accordingly, adhesion assays were performed to determine whether the FLAG mAb would block A549 cell adhesion to plastic wells coated with recombinant FLAG penton base protein. As in the prior example, wells were coated with recombinant FLAG or wild-type penton base proteins. The coated wells were then further incubated with 50 µg/ml of either FLAG mAb or the mAb, 12CA5, directed against the hemagglutinin peptide epitope, for one hour at room temperature followed by washing. The 12CA5 mAb was obtained from Joseph Bruder (GenVec, Inc., Rockville, Md.). Approximately 5×10$^4$ labeled A549 cells in 300 µl of adhesion buffer were added to each of the wells. The cells were allowed to adhere for about 30 minutes at about 37° C., and were then washed two times with adhesion buffer. The remaining adherent cells were then solubilized in about 200 µl of 1% SDS, and radioactivity was quantified by measuring cpm.

Figure 6:
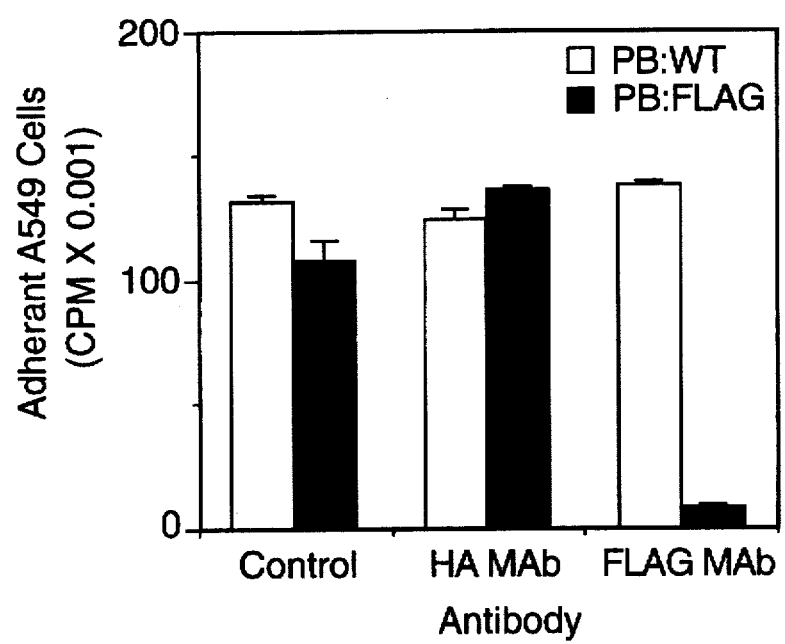
FIG. 6 is a bar chart that depicts inhibition of adhesion of A549 cells as measured by adherent cells (CPM×0.001) to either PB:FLAG (solid bars) or PB:WT (open bars) in the absence (control condition) or presence of either the FLAG mAb (directed against the FLAG epitope) or the HA mAb (12CA5 mAb, directed against the hemagluttinin peptide epitope).

As depicted in FIG. 6, the FLAG mAb completely blocked adhesion of A549 cells to the recombinant FLAG penton base protein (solid bars), but not to the wild-type penton base protein (open bars). The control HA mAb had no effect on A549 adhesion to either penton base protein. These results confirm that the FLAG mAb specifically recognizes the recombinant FLAG penton base protein, and thereby blocks the RGD domain from interacting with $\alpha_v$ integrins.

Example 17

This example describes the construction of recombinant adenovirus containing the chimeric penton base proteins PB:FLAG and PB:HA.

The recombinant penton base genes from the baculovirus transfer vectors pAcSG2 PB:FLAG and pAcSG2 PB:HA were transferred into the adenovirus transfer vector, pAd 37–59, to make the adenovirus transfer vectors pAd 37–59 PB:FLAG and pAd 37–59 PB:HA. In each of these cases, the Eco RI-Bgl II fragment comprising the chimeric gene was subcloned into pAd 37–59. The plasmid pAd 37–59 was constructed by cloning the Pme I-Bam HI fragment (comprising m.u. 37–59) of Ad5 into the cloning vector, pNEB193 (New England Biolabs, Beverly, Mass.).

The recombinant adenovirus vectors were made by first isolating viral DNA from the adenovirus vector Ad5CMVGlu. Purified vector DNA was isolated by digesting the purified virus overnight in a solution comprising about 0.5% SDS, 10 mM EDTA, 10 mM Tris-buffered saline, pH 7.8, containing 1 mg/ml proteinase K. The solution was then phenol/chloroform extracted three times and ethanol precipitated. A portion of the purified DNA was then cut overnight with the restriction enzyme Xmn I, which cleaves wild-type Ad5 at nucleotides 14561 and 15710 within the Ad5 genome. The DNA was then purified and calcium phosphate transfected into 293 cells along with either the linearized pAd 37–59 PB:FLAG or pAd 37–59 PB:HA DNA. The resultant recombinant vectors, AdFLAG and AdHA, were plaque-purified three times before propagating high-titer viral stocks. The presence of the proper antibody epitope in each vector was confirmed using PCR, and through Spe I restriction analyses of the vectors.

To verify that the AdFLAG virus contained the functional FLAG epitope, immunofluorescent detection of AdFLAG, AdHA, or wild-type Ad-infected 293 cells was performed. For these experiments, adenovirus-infected cells producing penton base proteins were detected using a standard fluorescent focus assay with minor modifications (Thiel et al., Proc. Soc. Exp. Biol. Med., 125, 892–895 (1967)). Briefly, 293 cells were plated at 50% confluency in 6-well polystyrene plates one day prior to infection with AdWT, AdFLAG, or AdHA at an MOI of about 0.015. The cells were then incubated at 37° C. for about two days, after which the cells were washed and fixed with methanol. The cells were then preblocked with PBS containing 5% BSA, and were incubated with a 1:500 dilution of a rabbit polyclonal antibody directed against penton base, the mouse FLAG mAb directed against the FLAG-containing chimeric penton base protein, or the mouse 12CA5 mAb directed against the hemagglutinin (HA) peptide. The cells were then washed three times and incubated with a 1:200 dilution of either an anti-mouse or anti-rabbit polyclonal FITC-labeled antibody (SIGMA, St. Louis, Mo.). Following incubation, the cells were washed three times and then visualized and photographed using a Nikon Diaphot 200 inverted microscope (Tokyo, Japan).

Only cells infected with AdFLAG were detected with use of the FLAG mAb. In comparison, cells infected with either the AdFLAG or the base Ad vector lacking the FLAG epitope (i.e., AdWT) were both detected by immunofluorescence using a polyclonal antibody directed against penton base protein (data not shown). The similar virus, AdHA, which incorporates the HA epitope into penton base, was specifically recognized by the HA mAb, but not the FLAG mAb. These results confirm that the FLAG mAb specifically recognizes the chimeric FLAG-containing penton base protein. Moreover, the antibody can be employed to detect AdFLAG, which incorporates this chimeric penton base protein, in transduced cells.

Example 18

This example describes an investigation of the transduction of fiber receptor-blocked 293 cells using AdFLAG complexed with the L230:FLAG bsAb.

These studies were performed to determine whether the L230:FLAG bispecific antibody complexed to the AdFLAG vector could mediate transduction of cells via $\alpha_v$ integrins to fiber receptor-containing cells. Cell transduction using the L230:FLAG bispecific antibody complexed to the AdFLAG vector also was investigated wherein the native fiber/fiber receptor interaction was blocked by blocking the fiber receptor with competing soluble fiber protein.

For these experiments, confluent monolayers of 293 cells in 24-multiwell plates were preincubated in the absence or presence of 300 µl of 5 µg/ml of Ad5 fiber protein for one hour at room temperature. About $10^8$ pfu/ml of the AdFLAG vector, or the control vector, AdHA, containing the HA epitope YPYDVPDYA (i.e., Tyr Pro Tyr Asp Val Pro Asp Tyr Ala [SEQ ID NO:31]), in place of the FLAG epitope were incubated with increasing concentrations of L230:FLAG bsAb. Both vectors are otherwise identical, and each contains the CMV β-glucuronidase gene, which is useful as a reporter gene to monitor entry of the recombinant adenoviruses into cells. The incubation of the adenovirus vectors with the L230:FLAG bispecific antibody was carried out for 45 minutes at room temperature in DMEM containing 20 mM HEPES. About 20 µl of each vector sample was then added to the fiber-blocked or unblocked 293 cells, and incubated for 1 hour at room temperature. The cells were then washed twice with DMEM and incubated for about 18 hours at 37° C. in DMEM containing 5% calf serum. The medium was then aspirated off, and the cells were lysed in 300 µl of 1X lysis buffer containing 10 mM EDTA (Promega, Madison, Wis.). About 3 µl of each sample was then assayed using a β-glucuronidase (GUS) fluorometric assay kit (Tropix, Bedford, Mass.), and using a luminometer. Results were reported as the average of duplicate samples.

Figure 7A:
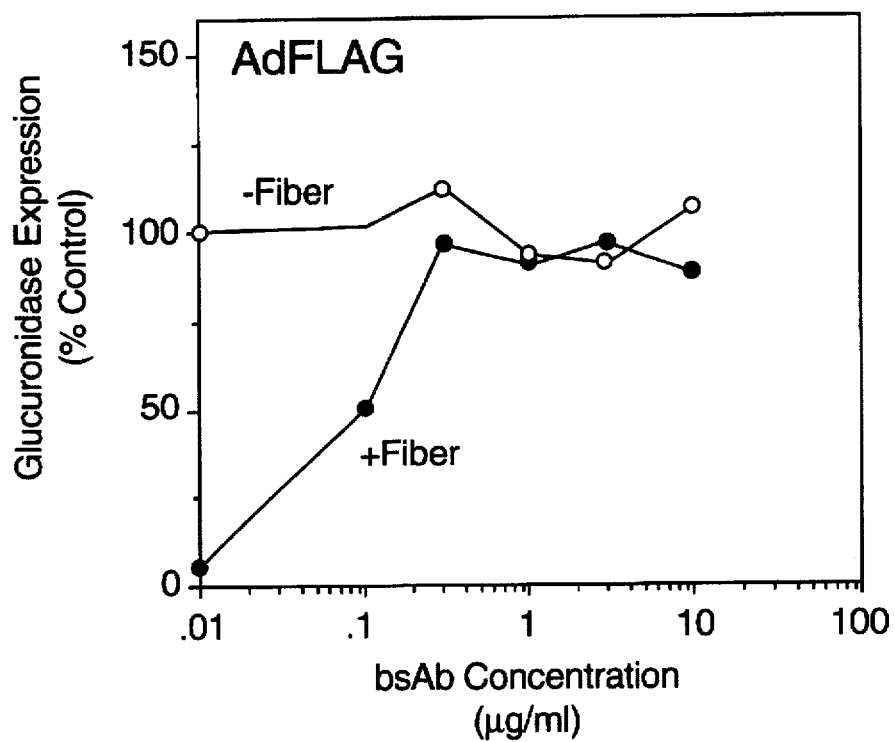
FIGS. 7A–B depict β-glucuronidase expression (% control) in cells transduced with AdFLAG (FIG. 7A) or AdHA (FIG. 7B) recombinant adenovirus vectors preincubated with the indicated concentration of the L230:FLAG bispecific antibody in the presence (closed circles) or absence (open circles) of soluble adenovirus fiber protein.
Figure 7B:
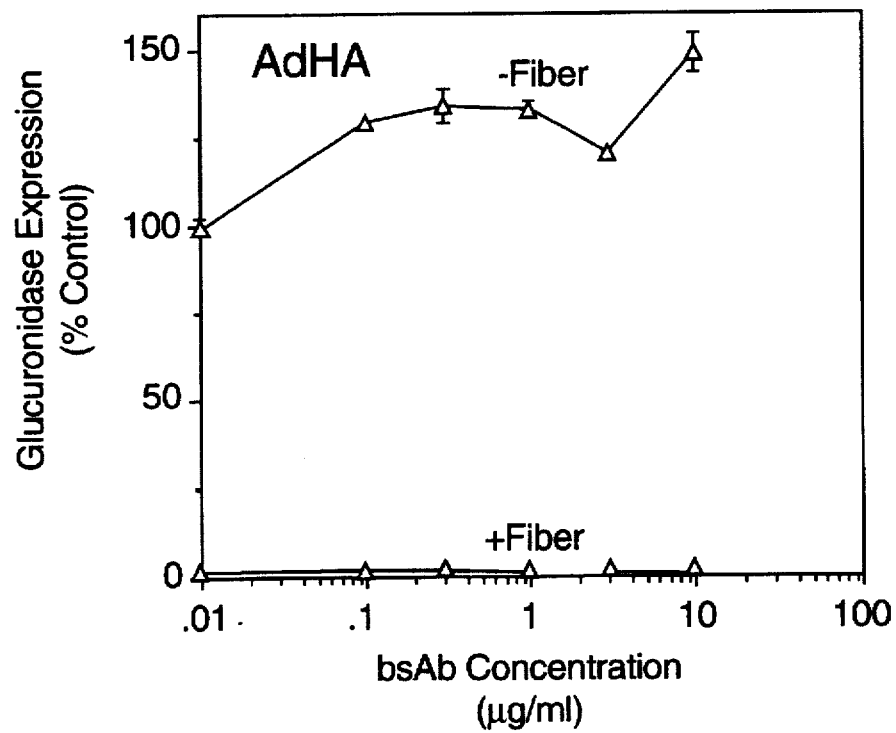

As can be seen in FIGS. 7A–B, with very low levels of bispecific antibody (e.g., about 0.01 µg/ml bsAb), the soluble fiber protein (closed circles) blocked over 95% of the transduction of both the AdHA (FIG. 7A) and AdFLAG (FIG. 7B) vectors. In the presence of fiber, increasing concentrations of L230:FLAG did not overcome the block in AdHA-mediated β-glucuronidase transduction imposed by the fiber protein (FIG. 7B). However, in comparison, increasing concentrations of L230:FLAG added to AdFLAG prior to transduction overcame the block in β-glucuronidase transduction effected by soluble competing fiber (FIG. 7A). Furthermore, L230:FLAG added to AdFLAG was able to completely restore transduction to the same levels as observed in the absence of competing fiber (open circles).

These results confirm that the AdFLAG vector, when complexed with the L230:FLAG bispecific antibody, can mediate transduction of cells via $\alpha_v$ integrins. The efficiency of L230:FLAG-mediated transduction is about equivalent to the efficiency of purely fiber-mediated adenovirus transduction of cells.

Example 19

This example describes an investigation of the binding of fiber receptor-blocked 293 cells using AdFLAG complexed with the L230:FLAG bsAb.

To confirm that the increased transduction efficiency by the AdFLAG/bsAb complex is due to increased binding of the complex to cells, the binding of radiolabeled vector to HISMC and HuVEC cells in the presence or absence of the L230:FLAG bsAb was measured. For these experiments, radiolabeled AdFLAG or the control vector AdWT were preincubated with either the L230:FLAG bsAb, the control FLAG mAb, or the control L230 mAb. Confluent monolayers of 293 cells in 24-multiwell plates were preincubated in the presence or absence of about 300 µl of 5 µg/ml soluble adenovirus fiber protein for about one hour at 4° C. About 24,000 cpm of [$^3$H]-methyl thymidine-labeled AdFLAG or AdWT vector were preincubated with about 3 µg/ml of either the L230 mAb, the L230:FLAG bsAb, the FLAG mAb, or the L230 mAb, for about 45 minutes at about 4° C. in a total volume of about 20 µl. Each sample was then added to the fiber-blocked or unblocked 293 cells, and incubated for about one hour at 4° C. The cells were then washed three times with PBS and solubilized in about 200 µl of a 1% SDS solution. Cpm were measured by scintillation counting and reported as the average of duplicate samples.

Figure 8A:
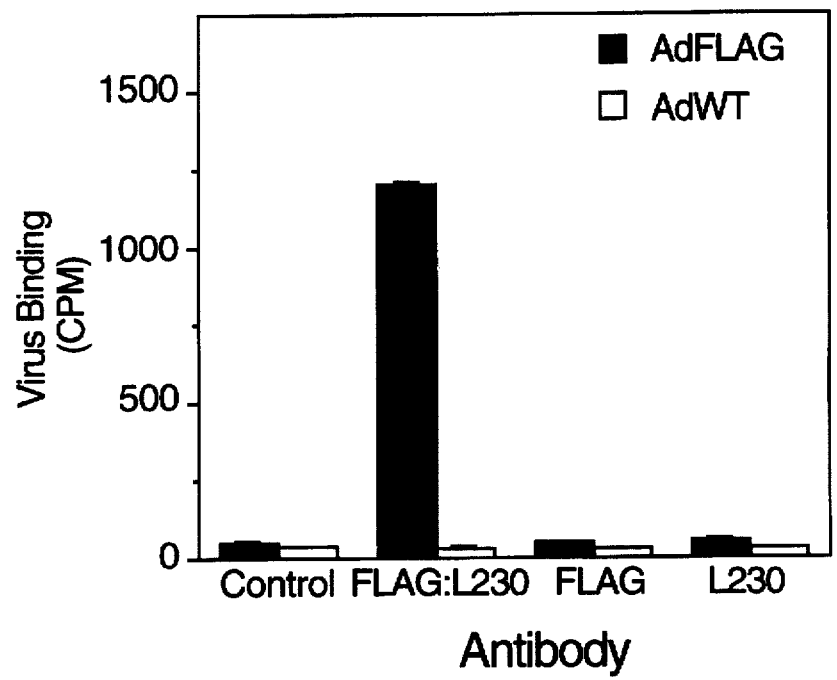
FIGS. 8A–B depict virus binding (CPM) to 293 cells in either the presence (FIG. 8A) or absence (FIG. 8B) of soluble adenovirus fiber protein, of AdWT (open bars) or AdFLAG (closed bars) complexed with either no antibody (control condition), the L230: FLAG bispecific antibody, the FLAG mAb, or the L230 mAb.
Figure 8B:
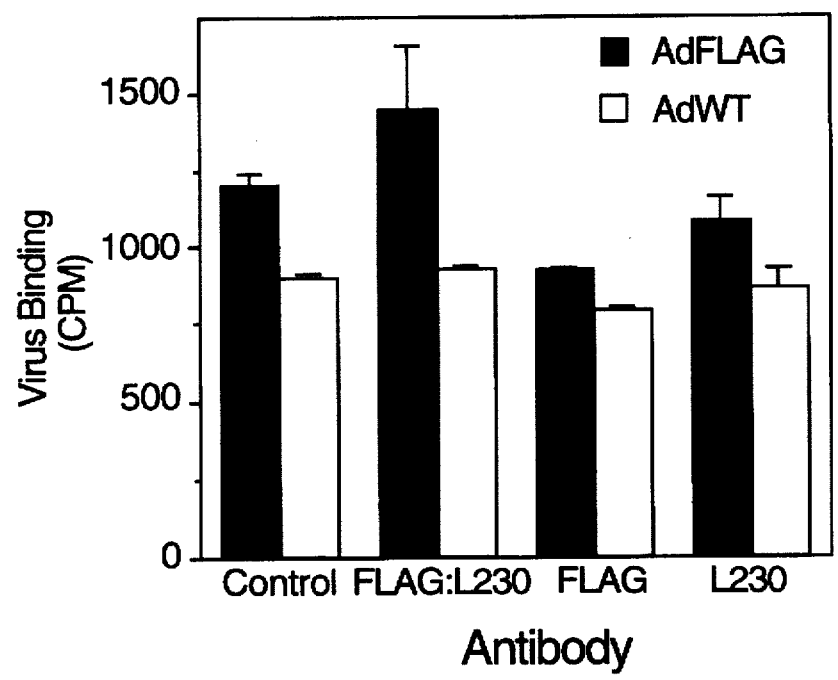

As can be seen in FIG. 8A, the presence of soluble competing fiber blocked all AdWT binding regardless of the antibody employed. In comparison, the ability of fiber protein to block adenovirus attachment to cells was overcome when the AdFLAG vector was preincubated with the L230:FLAG bsAb. Neither the FLAG mAb nor the L230 mAb alone were similarly able to overcome the fiber-mediated block of adenovirus binding. Moreover, the level of binding achieved by the AdFLAG/bsAb complex was the same as the binding level achieved in the absence of competing fiber protein (FIG. 8B).

These results confirm that the increase in transduction efficiency of the AdFLAG/bsAb complex is a result of increased vector binding. In addition, the results validate that the AdFLAG/bsAb complex is just as efficient in binding to fiber-blocked cells as is the vector alone in binding via the fiber. Furthermore, the results establish that the AdFLAG/bsAb complex can be employed to effect gene delivery to cells in the absence of any contribution to cell attachment and/or cell entry by the adenoviral fiber protein. The results thus confirm that adenoviral base protein can command both cell attachment and cell entry, even in the absence of adenoviral fiber protein.

Example 20

This example describes an investigation of whether the L230:FLAG bsAb complexed to the AdFLAG vector can increase transduction of endothelial and smooth muscle cells which lack high levels of fiber-mediated virus binding.

For these experiments, cell transduction by either the AdFLAG or AdHA vectors complexed to the L230:FLAG bsAb was measured: (1) in the absence of any blocking; (2) following the preincubation of vector with the FLAG mAb; and (3) following the preincubation of cells with the L230 mAb, or with no antibody. The HISMC, HuVEC, A549, or 293 cells were inoculated into 24-well plates about one to two days prior to experiments. In assays evaluating the bispecific antibody (bsAb) dose-response in cells producing fiber receptor, 293 cells were first incubated in the presence or absence of about 5 µg/ml of recombinant soluble fiber protein. About $10^8$ PFU/ml of either the AdFLAG or AdHA vectors were preincubated in the presence or absence of 50 µg/ml FLAG mAb prior to the addition of 3 µg/ml of the L230:FLAG bsAb for 45 minutes at room temperature. 293 cells were additionally incubated for 45 minutes at room temperature in the presence or absence of 50 µg/ml L230 mAb in a total volume of 300 µl DMEM. Following the incubations of vector and cells, 20 µl of each vector sample was added to the fiber-blocked or unblocked 293 cells and incubated for 1 hour at room temperature. The cells were then washed twice with DMEM, and further incubated in DMEM containing 5% calf serum for 18 hours at 37° C. The medium was aspirated off, and β-glucuronidase activity was measured in each sample as previously described. Duplicate measurements were made. The data were reported as relative light units (RLU)×1000 +/standard error. The results of these experiments are depicted in Table 2.

TABLE 2

Increased transduction of HuVEC and HISMC by the AdFLAG/bsAb complex blocked by L230 mAb or FLAG mAb.

| Condition | Smooth muscle cells | |
|---|---|---|
|  | AdFLAG | AdHA |
| Complex added to unblocked cells | 148.1 +/ 0.3 | 7.8 +/− 0.1 |
| FLAG mAb added to VECTOR | 8.4 +/− 0.1 | 9.2 +/− 0.1 |
| L230 mAb added to CELLS | 5.3 +/− 0.1 | 15.5 +/− 0.1 |

| Condition | Endothelial cells | |
|---|---|---|
|  | AdFLAG | AdHA |
| Complex added to unblocked cells | 378.2 +/− 1.6 | 31.5 +/− 1.5 |
| Flag mAb added to VECTOR | 27.5 +/− 0.7 | 35.5 +/− 0.7 |
| L230 mAb added to CELLS | 14.6 +/− 0.5 | 24.2 +/− 2.1 |

As can be seen from the data in Table 2, use of the L230:FLAG bsAb did not result in an increase in transduction by the AdHA vector. The same result was also observed using the FLAG or L230 antibody instead of the L230:FLAG bsAb. In comparison, the L230:FLAG bsAb, but not either the FLAG mAb or the L230 mAb alone, substantially increased the transduction of smooth muscle and endothelial cells by the AdFLAG vector. Transduction of the endothelial and smooth muscle cells by the AdFLAG/bsAb complex was increased 9- and 7-fold, respectively, compared to the AdFLAG vector alone.

The data of Table 2 also reveal whether the increased transduction by the AdFLAG/bsAb complex can be blocked through preincubation of cells with the L230 mAb, or by virus preincubation with the FLAG mAb. Any apparent block in transduction under these conditions would indicate that the increased transduction by the AdFLAG/bsAb complex is specific to the dual interaction of the L230:FLAG bsAb with the FLAG epitope on the virus, and with $\alpha_v$ integrins on the cells. As can be seen in Table 2, preincubation of the control vector, AdHA, with FLAG mAb prior to its incubation with the L230:FLAG bsAb resulted in no substantial decrease in transduction by AdHA of either HISMC or HuVEC cells. However, preincubation of AdFLAG with the FLAG mAb prior to incubation with the L230:FLAG bsAb blocked the increased transduction of both the endothelial and smooth muscle cells that is observed with use of the AdFLAG/bsAb complex alone. Similarly, preincubation of the cells with the L230 mAb blocked transduction of the cells by the AdFLAG/bsAb complex, and had no substantial effect on the transduction by AdHA preincubated with the L230:FLAG bsAb.

While data using HISMC and HUVEC cells is reported here, undetectable levels of fiber receptor similarly were observed as measured by fiber-specific adenovirus binding in primary human aorta smooth muscle cells (HASMC). These cells also are more efficiently transduced using the L230:FLAG bsAb complex with AdFLAG. In other experiments, from 7- to 40- fold increases in transduction of HASMC and HISMC by the L230:FLAG bsAb complex with AdFLAG have been observed.

These results thus confirm that the dual interactions of the L230:FLAG bsAb with AdFLAG and with $\alpha_v$ integrin cell receptors is necessary to achieve the increase in transduction of HISMC and HuVEC. Moreover, the substantial increases shown here in binding and transduction of cells lacking high levels of fiber receptor validate that penton-commanded cell targeting using bispecific molecules such as bispecific antibodies can be used to expand the range of tissues amenable to efficient adenovirus-mediated gene therapy.

Example 21

This example describes an investigation of whether penton-mediated cell targeting can be employed to introduce adenovirus into cells which it typically does not infect.

Adenovirus exhibits a reduced ability to infect human lymphocytes. A number of potential blocks to the entry of the virus into these cells have been identified (Hotta et al., *J. Virol.*, 68, 7284–7291 (1994); Horvath et al., *J. Virol.*, 62, 341–345 (1988); Silver et al., *Virology*, 165, 377–387 (1988); Huang et al., supra). In particular, whereas a subpopulation of unstimulated peripheral blood lymphocytes (PBL) express the adenovirus fiber receptor, this population comprises only 27–33% of the total PBL cell population (Horvath et al., supra). The activation of PBL with phytohemagglutinin (PHA) does not substantially alter the percentage of T cells comprising the fiber receptor.

In addition to many T cells lacking substantial levels of fiber receptor, most T cells also lack a second adenovirus receptor, $\alpha_v$ integrins. Adenovirus has been found to efficiently bind to the T cell line, Molt-3, whereas uptake of adenovirus into these cells has been found to be impaired (Silver et al., supra). The reduced infectivity of T cells by adenovirus as compared to other cells has been correlated to a lack of $\alpha_v$ integrins (Huang et al., supra). Stimulation of PBL with PHA or phorbol 12-myristate 13-acetate (PMA) does not significantly upregulate $\alpha_v$ integrin expression. Only after stimulation of PBL with both PHA and PMA are $\alpha_v$ integrins produced by these cells. Furthermore, despite a majority of stimulated T cells having on their cell surface $\alpha_v$ integrins, the maximum percentage of these cells which were transduced by adenovirus was found to be only 16%, even though very high concentrations of vector (i.e., 1000 active particles per cell) were employed (Huang et al., supra).

The T cell receptor, CD3, is present on the surface of all T cells. Targeting this receptor using bispecific antibodies should allow the majority of the T cell population to bind adenovirus as compared to only the 27–33% which can bind a nontargeted adenovirus. Similarly, T cells targeted via CD3 should be efficiently transduced by a CD3-targeted adenovirus compared with a maximum of only 16% of the T cells achievable with untargeted adenovirus at high multiplicities of infection. Furthermore, for T cells that do comprise an adenoviral fiber receptor, CD3-targeted adenovirus potentially can increase uptake of the vector into cells.

These possibilities were investigated by preincubating about 2×10⁶ Jurkat cells per sample in about 0.25 ml of RPMI cell culture medium in the presence or absence of 5 µg/ml of soluble recombinant Ad5 fiber protein. [³H]-thymidine-labeled AdFLAG vector (containing the β-glucuronidase gene under the control of the CMV promoter) was preincubated with or without 1 µg/ml of the L230:FLAG bsAb, the OKT7:FLAG bsAb, or the mICAM-:FLAG bsAb. The OKT7:FLAG bsAb (provided by David Segal, NIH) comprises a FLAG mAb linked to a mAb directed against the human CD3 T cell receptor. The mICAM:FLAG bsAb comprises a FLAG mAb linked to a mAb against the mouse ICAM (intracellular adhesion molecule) receptor (Pharmingen, San Diego, Calif.). About 20,000 cpm of the complexed vector was then incubated for 2 hours with the fiber-blocked or unblocked Jurkat cells at about 4° C. The samples were washed 3 times with PBS. A portion of these cells was further cultured for 3 days in RPMI culture medium plus 10% FBS. The cells were then lysed in reporter buffer, and assayed for β-glucuronidase activity as described above. The remaining cells were resuspended in PBS and the cell associated cpm was measured in a scintillation counter.

Figure 9:
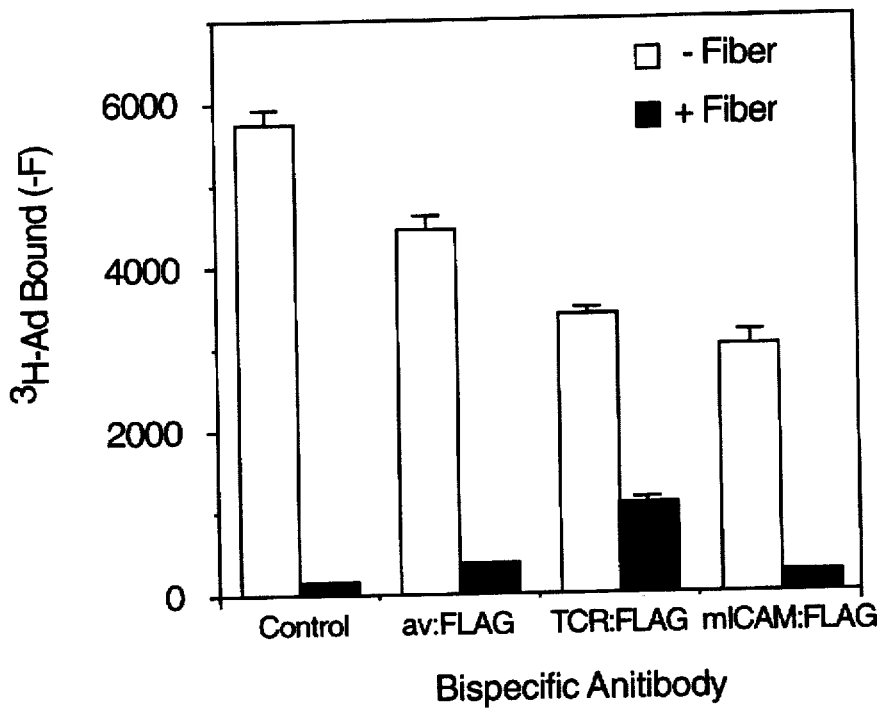
FIG. 9 depicts virus binding (CPM) to Jurkat cells in either the presence (dark bars) or absence (open bars) of soluble adenovirus fiber protein, of AdFLAG complexed with either no antibody (control condition), the L230: FLAG bispecific antibody (av:FLAG), the OKT7:FLAG bsAb (TCR:FLAG), or a mICAM:FLAG bispecific antibody.

The results of these experiments are presented in FIG. 9. As can be seen in FIG. 9, in the absence of soluble fiber protein, the uncomplexed adenoviral vector bound better to Jurkat cells than vector complexed with either the L230:FLAG bsAb, the OKT7:FLAG bsAb, or the mICAM-:FLAG bsAb. In comparison, the uncomplexed adenoviral vector bound the least well in the presence of added fiber.

Figure 10:
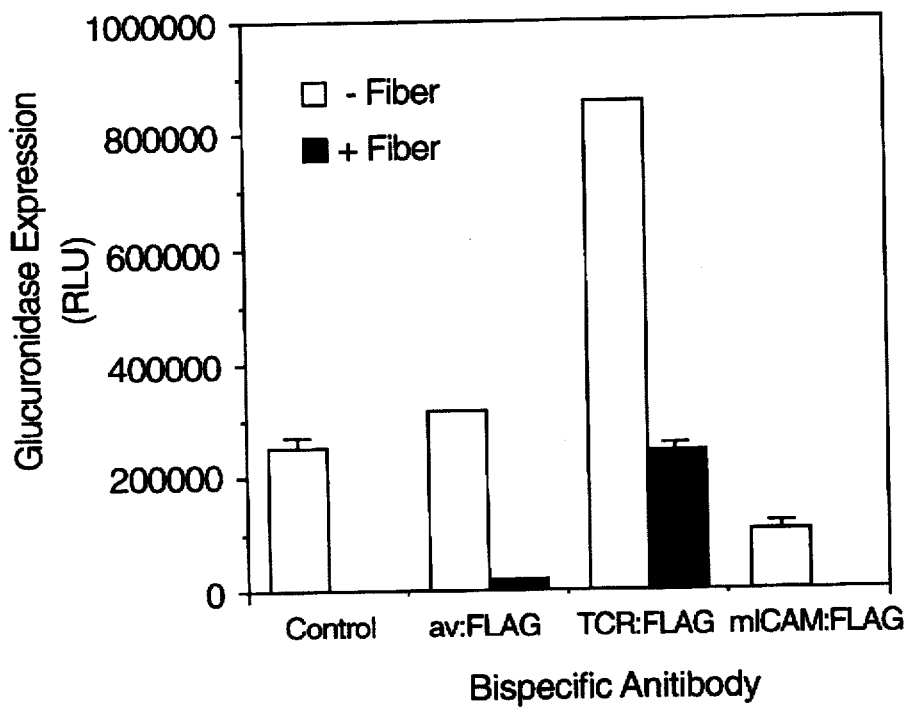
FIG. 10 depicts β-glucuronidase expression (RLU) in Jurkat cells transduced with either no antibody (control condition), the L230:FLAG bispecific antibody (av:FLAG), the OKT7:FLAG bsAb (TCR:FLAG), or a mICAM:FLAG bsAb in either the presence (dark bars) or absence (open bars) of soluble adenovirus fiber protein.

The effect of the various bispecific antibodies on gene transfer as measured by β-glucuronidase gene expression is presented in FIG. 10. For the Jurkat T cell line, which comprises high levels of fiber receptor, the TCR:FLAG:AdFLAG complex increased β-glucuronidase expression 5-fold. This increase in gene delivery occurred despite the decreased binding levels of the complexed vector compared to the uncomplexed vector. When the fiber receptor was blocked on Jurkat cells, the complexed vector efficiently transduced cells at the same level as unblocked cells transduced with uncomplexed vector. The efficient transduction of blocked Jurkat cells by the complexed vector indicates that peripheral blood T cells which lack the fiber receptor will be efficiently transduced by the complexed vector.

Figure 11:
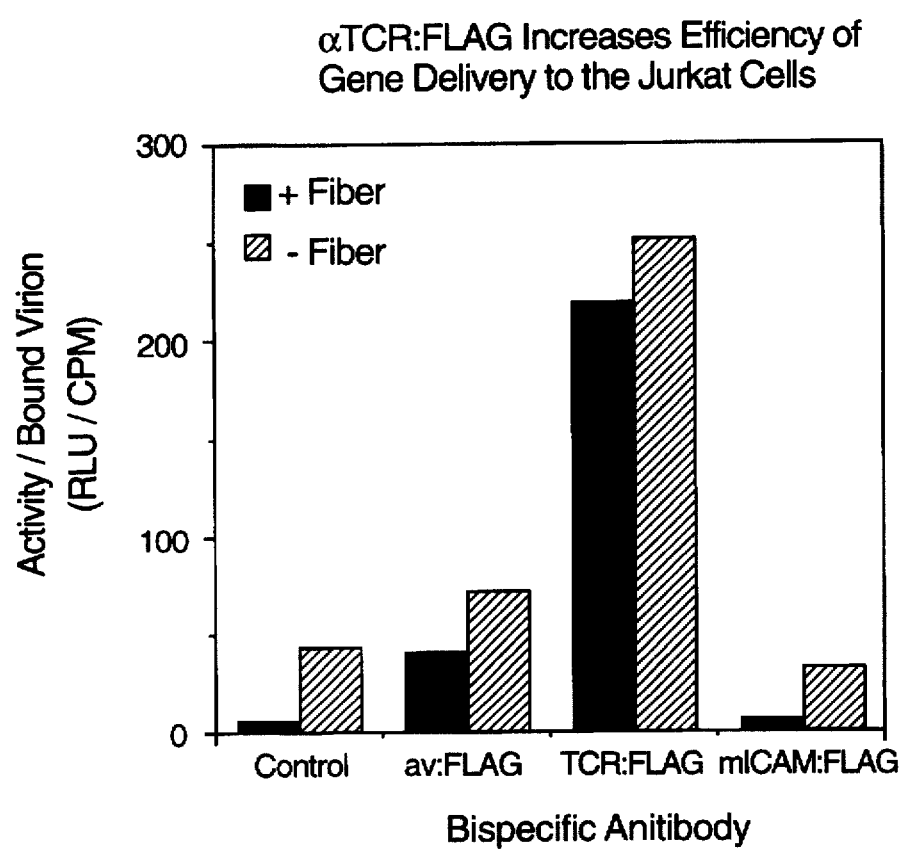
FIG. 11 depicts activity/bound virions (RLU/CPM) in Jurkat cells transduced with either no antibody (control condition), the L230:FLAG bispecific antibody (av:FLAG), the OKT7:FLAG bsAb (TCR:FLAG), or a mICAM:FLAG bsAb in either the presence (dark bars) or absence (stippled bars). of soluble adenovirus fiber protein.

The activity (i.e., gene expression) per adenovirus binding is depicted in FIG. 11. As can be seen from this figure, the TCR:FLAG:AdFLAG complex substantially increases the efficiency of gene delivery to T cells. These results confirm that the method can be used to selectively target adenovirus to T lymphocytes, in particular, by increasing the efficiency of gene delivery to these cells. The results further confirm that the method can be employed to transfer adenovirus to other cells that it typically does not infect and/or to increase the efficiency of adenoviral entry into any cell type.

Example 22

This example describes recombinant adenoviral vectors having chimeric fiber proteins that can be employed in the method of the present invention. Similar vectors having other chimeric fiber proteins can be constructed by a modification of the method herein.

Figure 12:
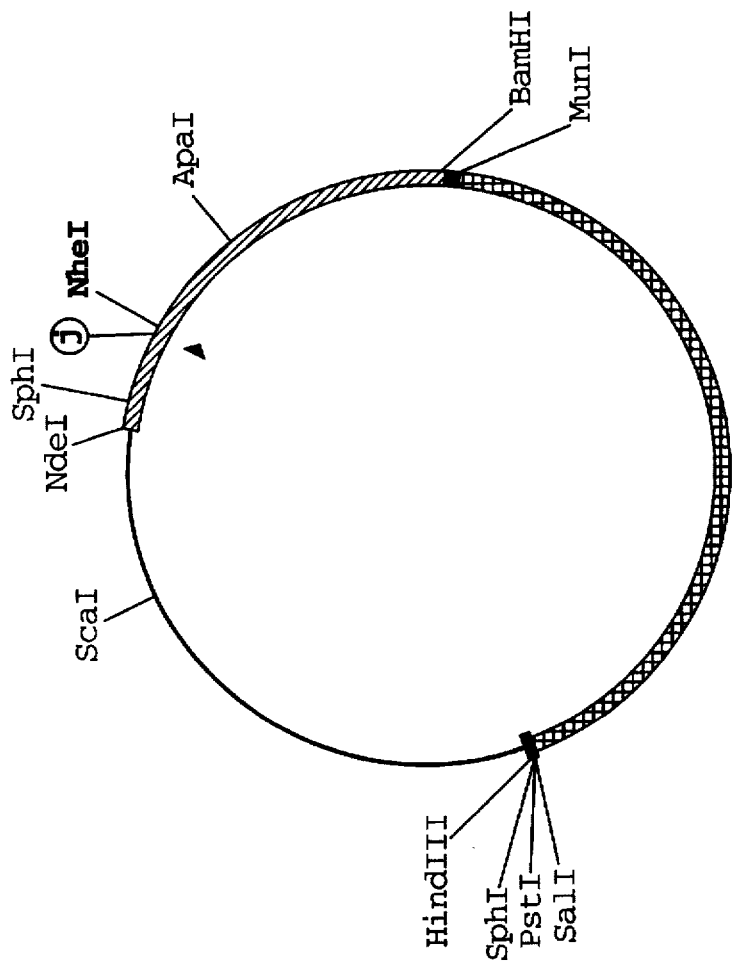
FIG. 12 is a partial restriction map of the adenoviral transfer vector p193(F5*)Nhe.
Figure 13:
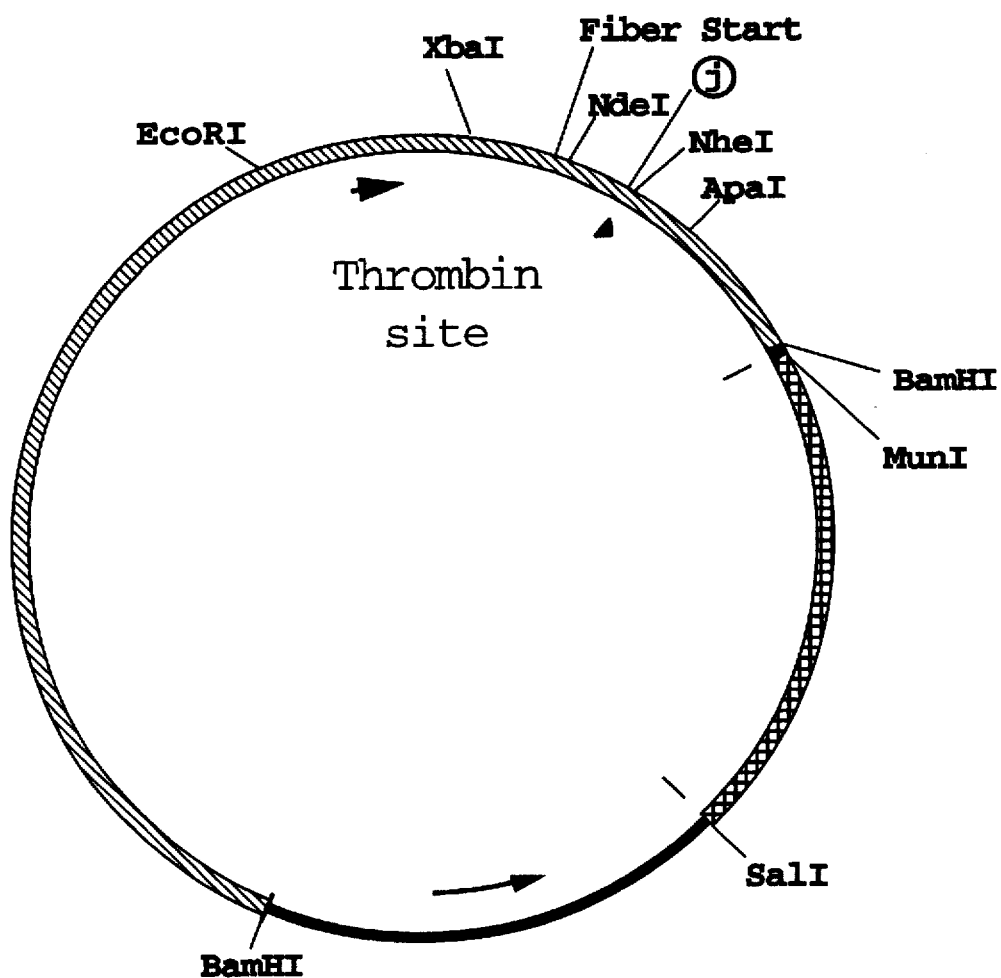
FIG. 13 is a partial restriction map of the adenoviral transfer vector pGBS 59–100(F5*)Nhe.

The fiber protein of adenovirus can be truncated by incorporating a cleavage site into the vector. In particular, a vector having the thrombin protease cleavage site GVPRGSLG (Gly Val Pro Arg Gly Ser Leu Gly [SEQ ID NO:40]) can be constructed. The 7326 base pair vector p193(F5*)Nhe depicted in FIG. 12 comprises this site. This vector was constructed by manipulating a p193(F5*) vector comprising the adenovirus fiber sequence. The vector was linearized at NheI, and an insert constructed by annealing 5' and 3' oligonucleotides was inserted to construct a vector comprising the nucleic acid sequence GGAAA GCTAGGCCGAGGAGTTCCCAGAGGGAGTCTTGGAA GGGGGAAGCTAGCCCTG [SEQ ID NO:41] (wherein the single underlined sequence comprises a Nhe I site, and the double underlined sequence comprises a modified Nhe I site). The modified vector thus codes for the amino acid sequence Gly Lys Leu Gly Arg Gly Val Pro Arg Gly Ser Leu Gly Arg Gly Lys Leu Ala Leu [SEQ ID NO:42], and encompasses SEQ ID NO:40. The 5' oligonucleotide used to construct this sequence comprises CTAGGCCGAGGAGT-TCCCAGAGGGAGTCTTGGAAGGGGGAAG [SEQ ID NO:43] The 3' oligonucleotide used to construct this sequence comprises CTAGCTTCCCCCTTCCAAGACTC-CCTCTGGGAACTCCTCGGC [SEQ ID NO:44]. To facilitate construction of recombinant adenovirus, the mutated fiber sequence then can be moved into a pGBS 59–100 vector (i.e., a pGEM vector containing adenovirus sequences that span the 59–100 map unit region of the Ad5 genome), by subcloning the NdeI-SalI fragment of p193 (F5*)Nhe to generate the 15,421 base pair vector pGBS 59–100(F5*)Nhe depicted in FIG. 13.

Figure 14:
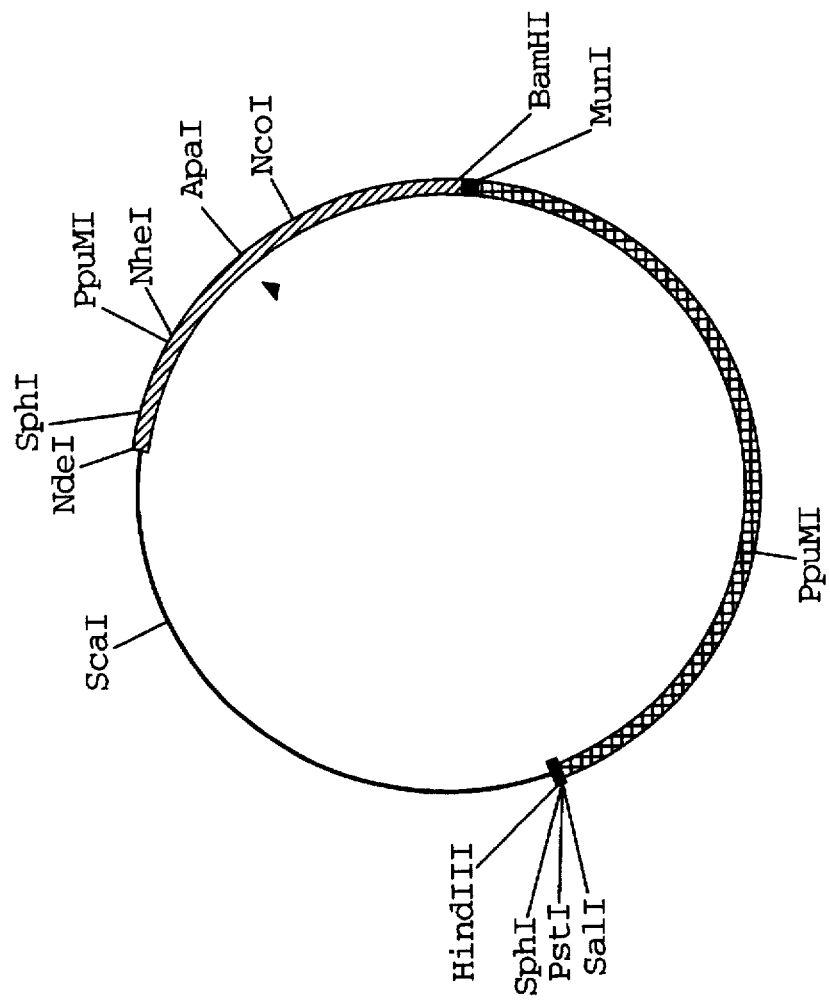
FIG. 14 is a partial restriction map of the adenoviral transfer vector p193(F5*)Apa.
Figure 15:
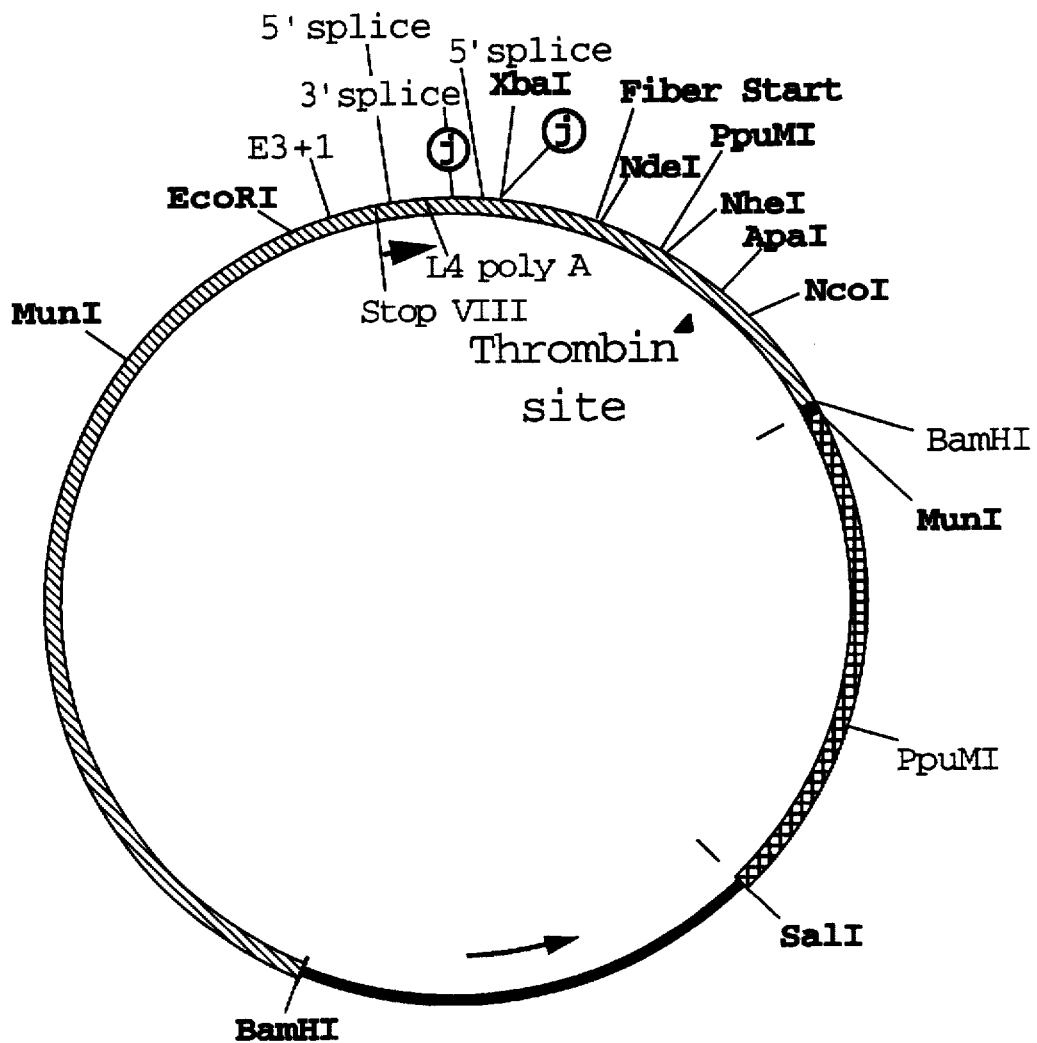
FIG. 15 is a partial restriction map of the adenoviral transfer vector pGBS 59–100(F5*)Apa.

Other vectors comprising the thrombin cleavage site of SEQ ID NO:40 at different positions within the fiber molecule also can be constructed by manipulating p193(F5*). For instance, the 7326 base pair vector p193(F5*)Apa depicted in FIG. 14 can be constructed by linearizing p193(F5*) at the Apa I site, and inserting a sequence constructed by annealing 5' and 3' oligonucleotides to generate a vector that comprises the sequence CTAAATCTAA-GACTAGGACAGGGCCGAGGAGTTCCCAGAGGGAG TCTTGGAAGGGGCCCTCTT [SEQ ID NO:45] (wherein the single underlined sequence comprises a Apa I site, and the double underlined sequence comprises a modified Apa I site), which codes for the amino acid sequence Leu Asn Leu Arg Leu Gly Gln Gly Arg Gly Val Pro Arg Gly Ser Leu Gly Arg Gly Pro Leu [SEQ ID NO:46]. The 5' oligonucleotide used to construct this sequence comprises GAGGAGTTC-CCAGAGGGAGTCTTGGAAGGGGCC [SEQ ID NO:47]. The 3' oligonucleotide used to construct this sequence comprises CCTTCCAAGACTCCCTCTGGGAACTC-CTCGGCC [SEQ ID NO:48]. The mutated fiber sequence then can be moved into a pGBS 59–100 vector by subcloning the NdeI-SalI fragment of p193(F5*)Apa to generate the 15,421 base pair vector pGBS 59–100(F5*)Apa depicted in FIG. 15.

Figure 16:
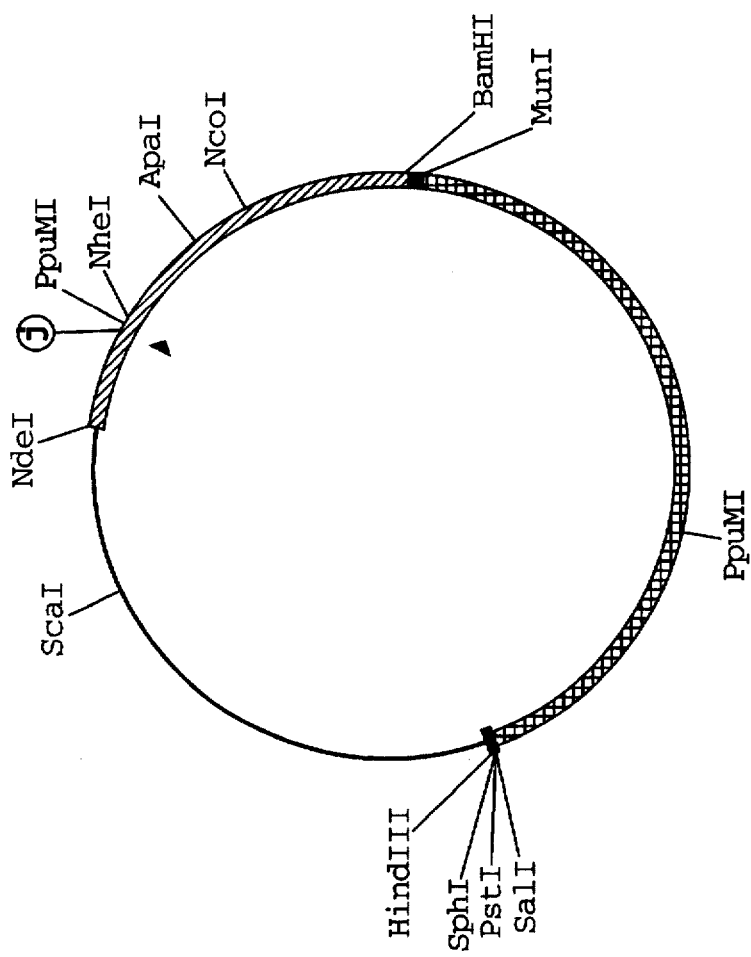
FIG. 16 is a partial restriction map of the adenoviral transfer vector p193(F5*)Ppu.
Figure 17:
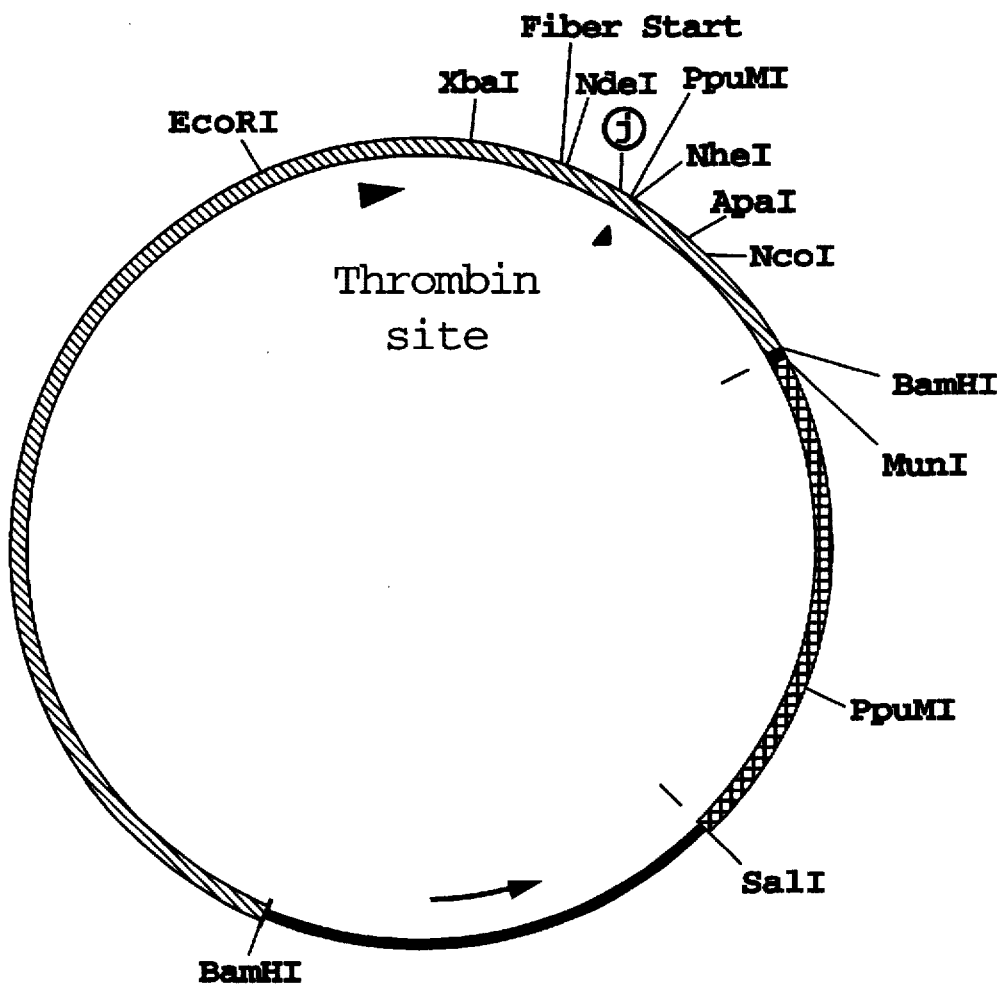
FIG. 17 is a partial restriction map of the adenoviral transfer vector pGBS 59–100(F5*)Ppu.

Similarly, the 7326 base pair vector p193(F5*)Ppu depicted in FIG. 16 can be constructed by linearizing p193(F5*) at the Ppu MI site, and inserting a sequence constructed by annealing 5' and 3' oligonucleotides to generate a vector that comprises the sequence ACCCA AGGACGAGGAGTTCCCAGAGGGAGTCTTGGAAG AGGACCCCTC [SEQ ID NO:49] (wherein the single underlined sequence comprises a Ppu MI site, and the double underlined sequence comprises a modified Ppu MI site), which codes for the amino acid sequence Thr Gln Gly Arg Gly Val Pro Arg Gly Ser Leu Gly Arg Gly Pro Leu [SEQ ID NO:50]. The 5' oligonucleotide used to construct this sequence comprises GACGAGGAGTTCCCAGAGG-GAGTCTTGGAAGAG [SEQ ID NO:51]. The 3' oligonucleotide used to construct this sequence comprises GTC-CTCTTCCAAGACTCCCTCTGGGAACTCCTC [SEQ ID NO:52]. The mutated fiber sequence then can be moved into a pGBS 59–100 vector by subcloning the NdeI-SalI fragment of p193(F5*)Ppu to generate the 15,421 base pair vector pGBS 59–100(F5*)Ppu depicted in FIG. 17.

Figure 18:
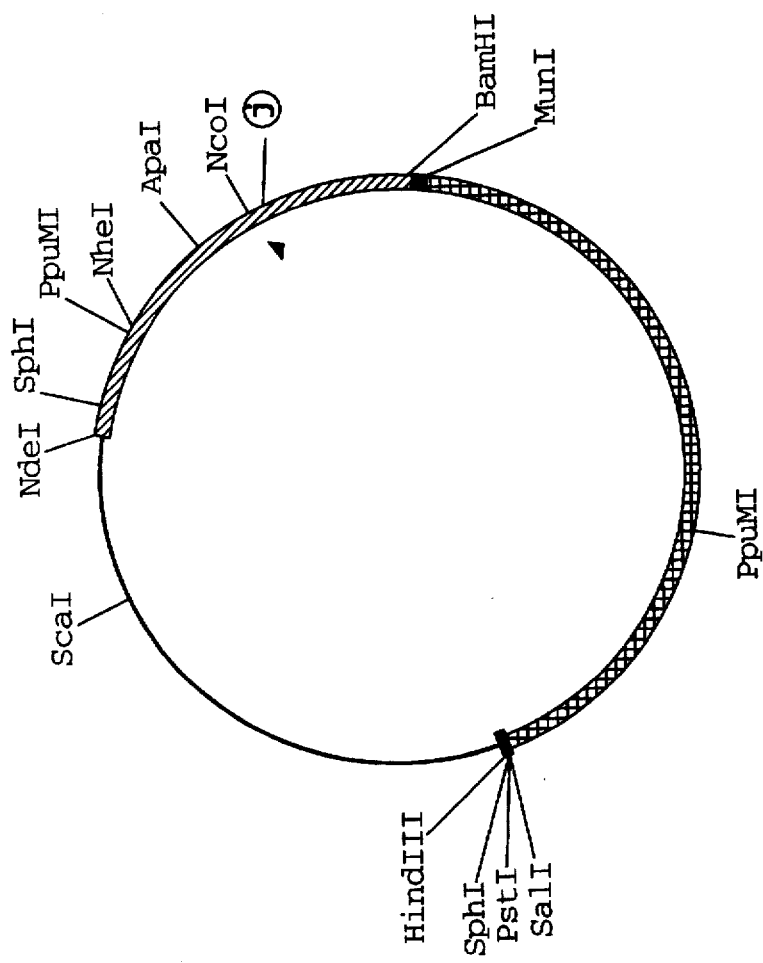
FIG. 18 is a partial restriction map of the adenoviral transfer vector p193(F5*)Nco.
Figure 19:
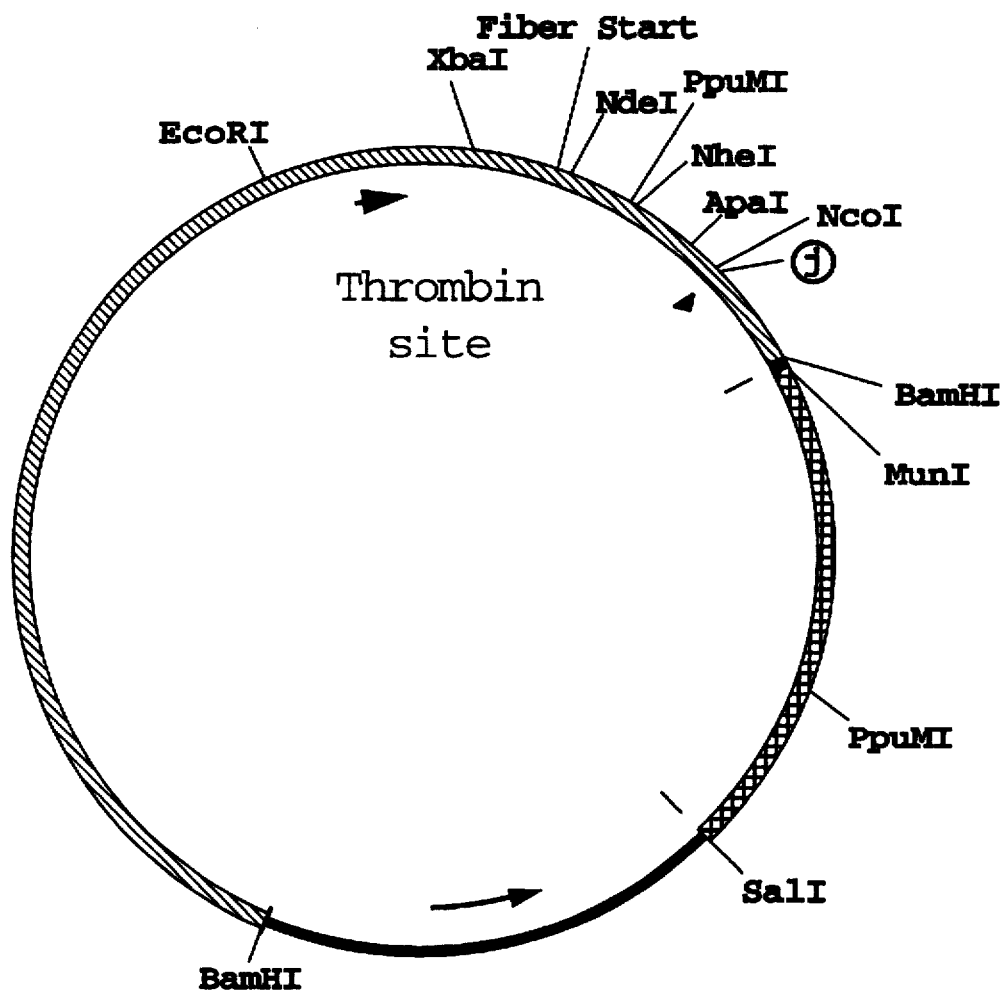
FIG. 19 is a partial restriction map of the adenoviral transfer vector pGBS 59–100(F5*)Nco.

Also, the 7332 base pair vector p193(F5*)Nco depicted in FIG. 18 can be constructed by linearizing p193(F5*) at the Nco I site, and inserting a sequence constructed by annealing 5' and 3' oligonucleotides to generate a vector that comprises the sequence ATTGG CCATGGCCGAGGAGTTCCCAGAGGGAGTCTTGGAA GGGGACATGGCCTA [SEQ ID NO:53] (wherein the single underlined sequence comprises a Nco I site, and the double underlined sequence comprises a modified Nco I site), which codes for the amino acid sequence Ile Gly His Gly Arg Gly Val Pro Arg Gly Ser Leu Gly Arg Gly His Gly Leu [SEQ ID NO:54]. The 5' oligonucleotide used to construct this sequence comprises CATGGCCGAGGAGTTC-CCAGAGGGAGTCTTGG AAGGGGA [SEQ ID NO:55]. The 3' oligonucleotide used to construct this sequence comprises CATGTCCCCTTCCAAGACTCCCT CTGG-GAACTCCTCGGC [SEQ ID NO:56]. The mutated fiber sequence then can be moved into a pGBS 59–100 vector by subcloning the NdeI-SalI fragment of p193(F5*)Nco to generate the 15,148 base pair vector pGBS 59–100(F5*)Nco depicted in FIG. 19.

Figure 20:
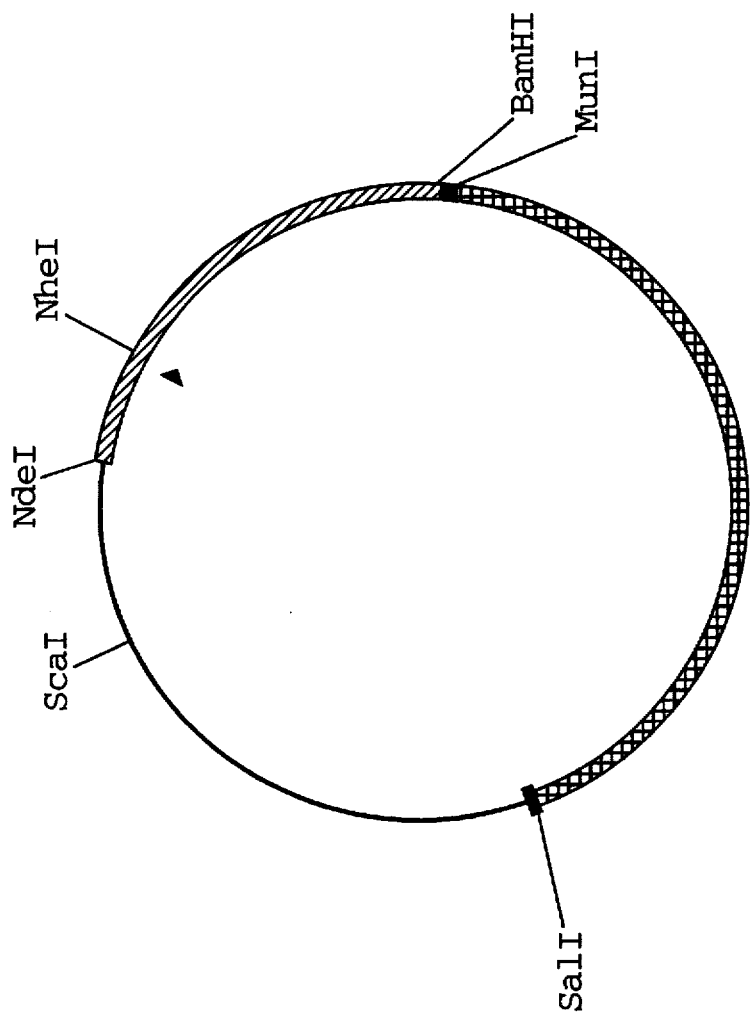
FIG. 20 is a partial restriction map of the adenoviral transfer vector p193(F5*)Try.

The fiber protein of adenovirus also can be truncated by incorporating a trypsin cleavage site into the vector. In particular, since Ad5 is resistant to trypsin treatment, sequences encoding multiple lysines can be subcloned in between the 7 and 8 repeat units in the fiber shaft. The high charge should keep the lysines exposed and available to the trypsin, and result in removal of the fiber protein from the virus. For instance, the 7326 base pair vector p193(F5*)Try depicted in FIG. 20 can be constructed by linearizing p193(F5*) at the Nhe I site, and inserting a sequence constructed by annealing 5' and 3' oligonucleotides to generate a vector that comprises the sequence GAAGGAAA GCTAGGCAAAAA GAAAAAGGGTAAGAAAAA-GAAAGGGAAGCTAGCC [SEQ ID NO:57] (wherein the single underlined sequence comprises a Nhe I site, and the double underlined sequence comprises a modified Nhe I site), which codes for the amino acid sequence Glu Gly Lys Leu Gly Lys Lys Lys Lys Gly Lys Lys Lys Lys Gly Lys Leu Ala [SEQ ID NO:58]. The 5' oligonucleotide used to construct this sequence comprises CTAGGCAAAAA-GAAAAAGGGTAAGAAAAAGAAAGGGAAG [SEQ ID NO:59]. The 3' oligonucleotide used to construct this sequence comprises CTAGCTTCCCTTTCTTTTTCTTAC-CCTTTTTCTTTTTGC [SEQ ID NO:60]. The mutated fiber sequence then can be moved into a pGBS 59–100 vector by subcloning the NdeI-SalI fragment of p193(F5*)Try into the pGBS 59–100 vector.

All references cited herein or cited in co-pending U.S. patent application Ser. No. 08/303,162, U.S. Pat. No. 5,559, 099 are hereby incorporated by reference to the same extent as if each reference were individually and specifically indicated to be incorporated by reference and were set forth in its entirety herein.

While this invention has been described with emphasis upon preferred embodiments, it will be obvious to those of ordinary skill in the art that the preferred embodiments can be varied. It is intended that the invention may be practiced otherwise than as specifically described herein. Accordingly, this invention includes all modifications encompassed within the spirit and scope of the appended claims.

What is claimed is:

1. A method of introducing an adenovirus into a cell in vitro, said cell comprising a particular cell surface binding site, which method comprises:
   (a) contacting said adenovirus with a bispecific molecule comprising (i) a first component that selectively binds a binding domain of the penton base protein of said adenovirus, and (ii) a second component that selectively binds said particular cell surface binding site, to form a complex of said adenovirus and said bispecific molecule, and
   (b) contacting said cell with said complex such that cell entry of said adenovirus is effected.

2. The method of claim 1, wherein said adenovirus comprises a passenger gene.

3. The method of claim 1, wherein said cell that comprises said particular cell surface binding site is a cell that wild-type adenovirus does not enter.

4. The method of claim 1, wherein said cell that comprises said particular cell surface binding site is a cell that wild-type adenovirus does enter.

5. The method of claim 1, wherein said bispecific molecule is a bispecific antibody comprising (a) a first antibody that selectively binds said binding domain, and (b) a second antibody that selectively binds said particular cell surface binding site.

6. The method of claim 1, which further comprises abrogating the binding of the fiber protein of said adenovirus to any cell surface molecule to which adenovirus can bind to effect cell entry of said adenovirus.

7. The method of claim 5, wherein said penton base protein is a wild-type adenovirus penton base protein.

8. The method of claim 5, wherein said penton base protein is a chimeric adenovirus penton base protein that comprises a binding domain that binds to a particular molecule which wild-type adenovirus penton base protein does not bind, and wherein said binding domain comprises an epitope for said first antibody.

9. The method of claim 5, wherein said penton base protein is a chimeric adenovirus penton base protein that comprises a binding domain that binds to a particular molecule which wild-type adenovirus penton base protein does bind, and wherein said binding domain comprises an epitope for said first antibody.

10. The method of claim 6, wherein said fiber protein is a wild-type adenovirus fiber protein, and binding of said fiber protein is abrogated by contacting said adenovirus with an antibody that selectively binds an epitope of said wild-type adenovirus fiber protein.

11. The method of claim 6, wherein said fiber protein is a chimeric adenovirus fiber protein that comprises a protease cleavage site, and binding of said fiber protein is abrogated by cleaving said fiber protein at said cleavage site.

12. The method of claim 6, wherein said fiber protein is a chimeric adenovirus fiber protein and binding of said fiber protein is abrogated by contacting said adenovirus with an antibody that selectively binds an epitope of said chimeric adenovirus fiber protein.

13. The method of claim 6, wherein said fiber protein is a chimeric adenovirus fiber protein that is unable to bind to a cell to which wild-type adenovirus fiber protein can bind.

14. The method of claim 8, wherein said epitope comprises a sequence selected from the group consisting of SEQ ID NO:25 and SEQ ID NO:31.

15. The method of claim 13, wherein said chimeric adenovirus fiber protein comprises an adenovirus fiber protein that is of a different adenoviral serotype than the remainder of said adenovirus.

16. A method of introducing an adenovirus into a cell in vitro, said cell comprising a particular cell surface binding site, which method comprises:
   (a) abrogating the binding of the fiber protein of said adenovirus to any cell surface molecule to which the fiber protein of said adenovirus can bind to effect cell entry of said adenovirus, and
   (b) contacting said cell with said adenovirus such that the penton base protein of said adenovirus binds said particular cell surface binding site and cell entry of said adenovirus is effected.

17. The method of claim 16, wherein said adenovirus comprises a passenger gene.

18. The method of claim 16, wherein said penton base protein is a wild-type adenovirus penton base protein.

19. The method of claim 16, wherein said penton base protein is a chimeric adenovirus penton base protein that comprises a binding domain that differs from the binding domain of a wild-type adenovirus penton base protein and that binds said particular cell surface binding site.

20. The method of claim 16, wherein said fiber protein is a wild-type adenovirus fiber protein, and binding of said fiber protein is abrogated by contacting said adenovirus with an antibody that selectively binds an epitope of said wild-type adenovirus fiber protein.

21. The method of claim 16, wherein said fiber protein is a chimeric adenovirus fiber protein that comprises a protease cleavage site, and binding of said fiber protein is abrogated by cleaving said fiber protein at said cleavage site.

22. The method of claim 16, wherein said fiber protein is a chimeric adenovirus fiber protein and binding of said fiber protein is abrogated by contacting said adenovirus with an antibody that selectively binds an epitope of said chimeric adenovirus fiber protein.

23. The method of claim 16, wherein said fiber protein is a chimeric adenovirus fiber protein that is unable to bind to a cell to which wild-type adenovirus fiber protein can bind.

24. The method of claim 19, wherein said cell surface binding site is one that wild-type adenovirus does not bind.

25. The method of claim 19, wherein said cell surface binding site is one that wild-type adenovirus does bind.

26. The method of claim 23, wherein said chimeric adenovirus fiber protein comprises an adenovirus fiber protein that is of a different adenoviral serotype than the remainder of said adenovirus.

27. The method of claim 24, wherein said binding domain comprises a sequence selected from the group consisting of SEQ ID NO:3, SEQ ID NO:32, SEQ ID NO:33, SEQ ID NO:34, SEQ ID NO:35, and SEQ ID NO:36.

28. The method of claim 25, wherein said binding domain comprises the sequence of SEQ ID NO:18.

29. A chimeric adenovirus penton base protein comprising a binding domain that differs from the binding domain of a wild-type adenovirus penton base protein.

30. The chimeric adenovirus penton base protein of claim 29, wherein said binding domain binds a molecule which wild-type adenovirus penton base protein does not bind.

31. The chimeric adenovirus penton base protein of claim 29, wherein said binding domain binds a molecule which wild-type penton base does bind.

32. The chimeric adenovirus penton base protein of claim 29, wherein said binding domain comprises the sequence of SEQ ID NO:18.

33. A vector comprising the chimeric adenovirus penton base protein of claim 29.

34. The chimeric adenovirus penton base protein of claim 30, wherein said binding domain comprises a sequence selected from the group consisting of SEQ ID NO:32, SEQ ID NO:33, SEQ ID NO:34, SEQ ID NO:35, and SEQ ID NO:36.

35. The chimeric adenovirus penton base protein of claim 30, wherein said binding domain comprises an epitope for an antibody.

36. A vector comprising the chimeric adenovirus penton base protein of claim 30.

37. A vector comprising the chimeric adenovirus penton base protein of claim 31.

38. The vector of claim 33, wherein said vector is a recombinant adenovirus.

39. The vector of claim 33, wherein said adenovirus further comprises a chimeric adenovirus fiber protein that is unable to bind to a cell to which wild-type adenovirus fiber protein can bind.

40. The vector of claim 33, wherein said vector is selected from the group consisting of p193(F5*)Nhe, pGBS 59–100 (F5*)Nhe, p193(F5*)Apa, pGBS 59–100(F5*)Apa, p193 (F5*)Ppu, PGBS 59–100(F5*)Ppu, p193(F5*)Nco, PGBS 59–100(F5*)Nco, p193(F5*)Try, and pGBS 59–100(F5*)Try.

41. The chimeric adenovirus penton base protein of claim 35, wherein said epitope comprises a sequence selected from the group consisting of SEQ ID NO:25 and SEQ ID NO:31.

42. The vector of claim 36, wherein said vector is a recombinant adenovirus.

43. The vector of claim 37, wherein said vector is a recombinant adenovirus.

44. The vector of claim 38, wherein said vector further comprises a passenger gene.

45. A method of introducing an adenovirus into a cell in vitro, said cell comprising a particular cell surface binding site, which method comprises:

(a) abrogating the binding of the fiber protein of said adenovirus to any cell surface molecule to which the fiber protein of said adenovirus can bind to effect cell entry of said adenovirus, and (b) contacting said cell with the vector of claim 38 such that the penton base protein of said adenovirus binds said particular cell surface binding site and cell entry of said adenovirus is effected.

46. A method of introducing an adenovirus into a cell in vitro, said cell comprising a particular cell surface binding site, which method comprises:

(a) contacting the vector of claim 38 with a bispecific molecule comprising (i) a first component that selectively binds a binding domain of the penton base protein of said adenovirus, and (ii) a second component that selectively binds said particular cell surface binding site, to form a complex of said adenovirus and said bispecific molecule, and (b) contacting said cell with said complex such that cell entry of said adenovirus is effected.

47. The vector of claim 39, wherein said chimeric adenovirus fiber protein comprises an adenovirus fiber protein that is of a different adenoviral serotype than the remainder of said recombinant adenovirus.

48. The vector of claim 42, wherein said vector further comprises a passenger gene.

49. The vector of claim 43, wherein said vector further comprises a passenger gene.

50. A vector comprising a chimeric adenovirus penton base protein that comprises a binding domain that differs from the binding domain of a wild-type adenovirus penton base protein, wherein said adenovirus further comprises a chimeric adenovirus fiber protein that comprises a protease cleavage site.

51. The vector of claim 50, wherein said vector comprises a sequence selected from the group consisting of SEQ ID NO:41, SEQ ID NO:43, SEQ ID NO:45, SEQ ID NO:49, SEQ ID NO:53, and SEQ ID NO:57.

52. The vector of claim 50, wherein said vector comprises a sequence selected from the group consisting of SEQ ID NO:8, SEQ ID NO:40, SEQ ID NO:42, SEQ ID NO:46, SEQ ID NO:50, SEQ ID NO:54, and SEQ ID NO:58.

* * * * *

UNITED STATES PATENT AND TRADEMARK OFFICE
CERTIFICATE OF CORRECTION

PATENT NO. : 5,712,136
DATED : January 27, 1998
INVENTOR(S) : Thomas J. Wickham; Imre Kovesdi; Petrus W. Roelvink; Douglas E. Brough; Duncan L. McVey and Joseph T. Bruder It is certified that errors appear in the above-identified patent and that said Letters Patent is hereby corrected as shown below:

ON THE TITLE PAGE:

Inventors:
Line 4: "Otney" should read --Olney--.

In Column 6, line 43: "arian" should read --avian--.
In Column 7, line 23: "arian" should read --avian--.
In Column 26, line 58: "unique I" should read --unique Spe I--.
In Column 28, line 64: "Ad5" should read --[Ad5--.
In Column 30, line 10: "$\beta_4$" should read --$\alpha_4$--.

Signed and Sealed this

Twenty-sixth Day of May, 1998

Attest:

BRUCE LEHMAN

Attesting Officer

Commissioner of Patents and Trademarks